United States Patent
Robbins et al.

(10) Patent No.: US 11,286,278 B2
(45) Date of Patent: Mar. 29, 2022

(54) DPEP-1 BINDING AGENTS AND METHODS OF USE

(71) Applicant: Arch Biopartners, Inc., Toronto (CA)

(72) Inventors: Stephen Mark Robbins, Calgary (CA); Donna Lorraine Senger, Calgary (CA); Daniel Abraham Muruve, Calgary (CA); Saurav Roy Choudhury, Calgary (CA); Jennifer Joy Rahn, Calgary (CA); Arthur Wing Sze Lau, Calgary (CA); Justin MacDonald, Cochrane (CA); Liane Babes, Calgary (CA); Paul Kubes, Calgary (CA)

(73) Assignee: Arch BioPartners, Inc., Toronto (CA)

( * ) Notice: Subject to any disclaimer, the term of this patent is extended or adjusted under 35 U.S.C. 154(b) by 0 days.

(21) Appl. No.: 16/700,901

(22) Filed: Dec. 2, 2019

(65) Prior Publication Data

US 2020/0223888 A1 Jul. 16, 2020

Related U.S. Application Data

(60) Provisional application No. 62/773,733, filed on Nov. 30, 2018.

(51) Int. Cl.
| | | |
|---|---|---|
| *C07K 7/08* | (2006.01) | |
| *A61P 35/04* | (2006.01) | |
| *C07K 7/06* | (2006.01) | |
| *A61P 13/12* | (2006.01) | |
| *A61K 38/00* | (2006.01) | |

(52) U.S. Cl.
CPC .............. *C07K 7/08* (2013.01); *A61P 13/12* (2018.01); *A61P 35/04* (2018.01); *C07K 7/06* (2013.01); *A61K 38/00* (2013.01)

(58) Field of Classification Search
CPC .......... A61K 38/00; A61P 13/12; A61P 35/00; A61P 35/04; C07K 14/81; C07K 2319/21; C07K 7/06; C07K 7/08; C12N 9/485
See application file for complete search history.

(56) References Cited

U.S. PATENT DOCUMENTS

| | | | | |
|---|---|---|---|---|
| 8,258,256 | B2 * | 9/2012 | Denmeade | C07K 7/08 530/300 |
| 10,493,127 | B2 * | 12/2019 | Robbins | A61K 38/55 |
| 2012/0207742 | A1 * | 8/2012 | Jacky | C07K 14/33 424/94.67 |
| 2013/0035256 | A1 * | 2/2013 | Gjoni | C07K 14/705 506/9 |
| 2019/0225673 | A1 * | 7/2019 | Kruse | A61P 31/20 |
| 2019/0307798 | A1 * | 10/2019 | Kruse | A61P 1/16 |

FOREIGN PATENT DOCUMENTS

| | | |
|---|---|---|
| WO | WO 2015/120536 | 8/2015 |
| WO | WO 2017/025802 | 2/2017 |

OTHER PUBLICATIONS

International Search Report for PCT/IB2019/001289, dated Apr. 9, 2020.

\* cited by examiner

*Primary Examiner* — Marcela M Cordero Garcia
(74) *Attorney, Agent, or Firm* — King & Spalding

(57) ABSTRACT

Pharmaceutical compositions and methods of their use are provided for reducing inflammation in a subject, blocking leukocyte recruitment, inhibiting tumor metastasis, treating sepsis and preventing/reducing acute kidney injury.

12 Claims, 54 Drawing Sheets
Specification includes a Sequence Listing.

DAPI  DPEP-1  ZO-1  Overlay

Isotype Control (20X)  DPEP-1 (20X)  DPEP-1 (40X)

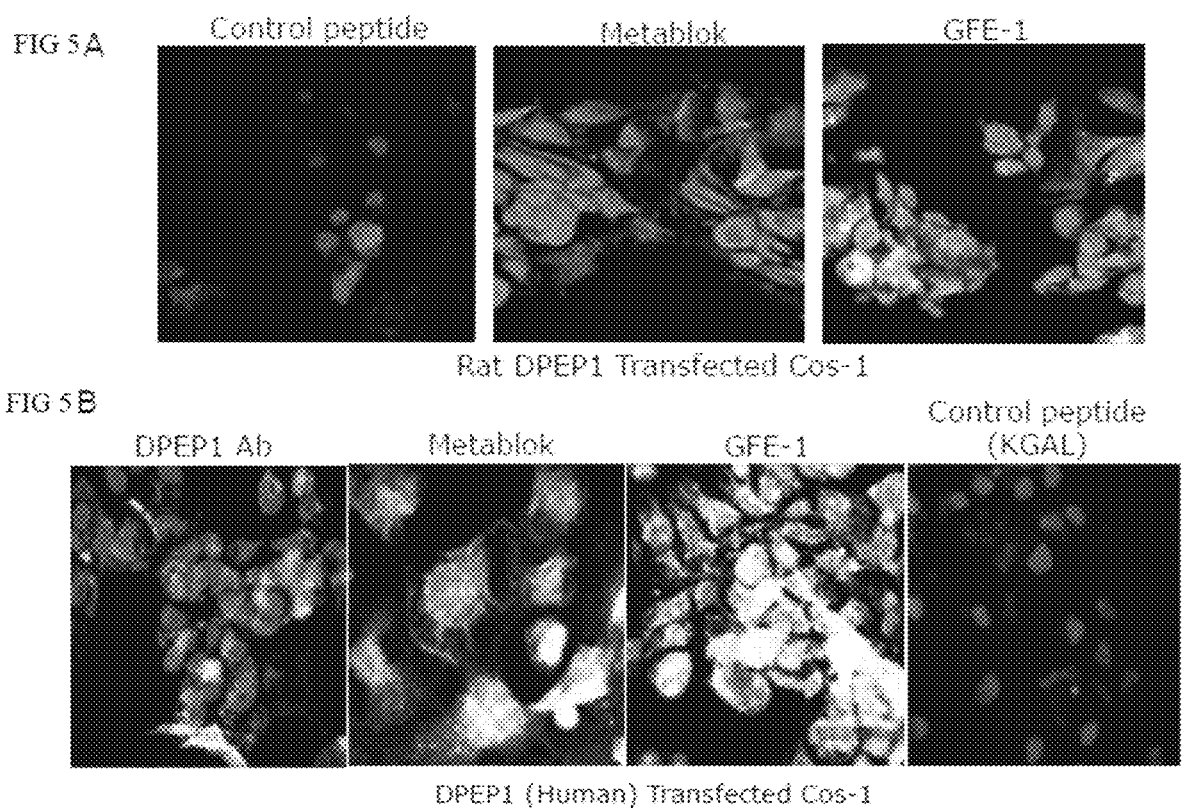

55 kDa

Pulled down with neutravidin agarose beads and Western blot

A

| Peptide | % Bound to HEK DPEP1 |
|---|---|
| LSALT | 17.8 ± 1.9 |
| GG-LSALT | 19.6 ± 0.1 |
| GGG-LSALT | 28.4 ± 2.5 |
| GGGG-LSALT | 20.4 ± 1.6 |
| GG-LSALT-NH | 37.8 ± 8.0 |
| GGG-LSALT-NH | 42.6 ± 8.8 |
| GGGG-LSALT-NH | 31.5 ± 6.8 |

FIG. 16A

```
LSALT    LSALTPSPSWLKYKAL
Pos 1    ASALTPSPSWLKYKAL
Pos 2    LAALTPSPSWLKYKAL
Pos 4    LSAATPSPSWLKYKAL
Pos 5    LSALAPSPSWLKYKAL
Pos 6    LSALTASPSWLKYKAL
Pos 7    LSALTPAPSWLKYKAL
Pos 8    LSALTPSASWLKYKAL
Pos 9    LSALTPSPAWLKYKAL
Pos 10   LSALTPSPSALKYKAL
Pos 11   LSALTPSPSWAKYKAL
Pos 12   LSALTPSPSWLAYKAL
Pos 13   LSALTPSPSWLKAKAL
Pos 14   LSALTPSPSWLKYAAL
Pos 16   LSALTPSPSWLKYKAA
```

FIG. 17A

| Peptide Sequence | Peptide Fragment | Fresh Citrate Plasma Normalized Area | | | | |
|---|---|---|---|---|---|---|
| | | Incubation Time at 37°C (min) | | | | |
| | | 0 | 10 | 20 | 60 | 120 |
| LSALTPSPSWLKYKAL (LSALT peptide) | -- | 22870000 | 20260000 | 10914000 | 3270000 | 135730 |
| SALTPSPSWLKYKAL | A | 5330 | 388000 | 546000 | 839000 | 288000 |
| ALTPSPSWLKYKAL | B | 0 | 55600 | 58600 | 111000 | 38800 |
| LTPSPSWLKYKAL | C | 0 | 91500 | 166000 | 367000 | 160000 |
| TPSPSWLKYKAL | D | 0 | 341070 | 196310 | 1002000 | 691000 |
| SPSWLKYKAL | E | 0 | 18400 | 33200 | 83900 | 61200 |
| TPSPSWLKYK | F | 0 | 0 | 0 | 557 | 0 |
| SWLKYKAL | G | 0 | 16340 | 85300 | 788000 | 1913000 |
| | | Fresh K$_2$EDTA Plasma Normalized Area | | | | |
| Peptide Sequence | Peptide Fragment | Incubation Time at 37°C (min) | | | | |
| | | 0 | 10 | 20 | 60 | 120 |
| LSALTPSPSWLKYKAL (LSALT peptide) | -- | 17700000 | 54900 | 5070 | 0 | 0 |
| SALTPSPSWLKYKAL | A | 1130000 | 267000 | 1180 | 0 | 0 |
| ALTPSPSWLKYKAL | B | 37000 | 18400 | 0 | 0 | 0 |
| LTPSPSWLKYKAL | C | 21100 | 119000 | 0 | 0 | 0 |
| TPSPSWLKYKAL | D | 57100 | 1235440 | 104703 | 0 | 0 |
| SPSWLKYKAL | E | 0 | 17500 | 199 | 0 | 0 |
| TPSPSWLKYK | F | 0 | 67700 | 7750 | 0 | 0 |
| SWLKYKAL | G | 0 | 244 | 0 | 0 | 0 |

| Peptide | % Bound to HEK DPEP1 |
|---|---|
| LSALT | 15.3 |
| Fragment A | 8.7 |
| Fragment B | 19.4 |
| Fragment C | 11.7 |
| Fragment D | 10.8 |
| Fragment E | 13.7 |
| Fragment F | 13.4 |
| Fragment G | 21.8 |

N=6-10 fields/group; **: p=0.0034

FIG. 19A

| | | BLAST tentative IDs |
|---|---|---|
| KHMHWHPPALNT | 3 (6.25%) | Neogenin |
| KHMHWHPPALNT | | |
| KHMHWHPPALNT | | |
| KPSVPLYPPYTP | | |
| KSLSRHDHIHHH | 17 + 1 (37.5%) | NKD1 |
| KSLSRHDHIHHH | | |
| KSLSRHDHIHHH | | |
| KSLSRHDHIHHH | | |
| KSLSRHDHIHHH | | |
| KSLSRHDHIHHH | | |
| KSLSRHDHIHHH | | |
| KSLSRHDHIHHH | | |
| KSLSRHDHIHHH | | |
| KSLSRHDHIHHH | | |
| KSLSRHDHIHHH | | |
| KSLSRHDHIHHH | | |
| KSLSRHDHIHHH | | |
| KSLSRHDHIHHH | | |
| KSLSRHDHIHHH | | |
| KSLSRHDHIHHQ | | |
| KSPVNHHHHYHX | | |
| KSVRRHHHIHHH | | |
| KYLRRHHHIHHH | | |
| NFSQPPSKHTRS | | |
| NHVHRMHATPAH | | |
| NHVHRMHATPAY | 11 +2 (27.1%) | Semaphorin 7A |
| NHVHRMHATPAY | | |
| NHVHRMHATPAY | | |
| NHVHRMHATPAY | | |
| NHVHRMHATPAY | | |
| NHVHRMHATPAY | | |
| NHVHRMHATPAY | | |
| NHVHRMHATPAY | | |
| NHVHRMHATPAY | | |
| NHVHRMHATPAY | | |
| NHVHRMHATPAY | | |
| NHVHRQHPTPAH | | |
| QSPVNHHHHYHH | | |
| QSPVNHHYHYHI | 3 +1 (8.3%) | GRIP1 |
| QSPVNHHYHYHI | | |
| QSPVNHHYHYHI | | |
| -SLHKHHHHQRH | | |
| STHHRHYHDTLA | 4 (8.3%) | ?? |
| STHHRHYHDTLA | | |
| STHHRHYHDTLA | | |
| STHHRHYHDTLA | | |

KHMHWHPPALNT

KSLSRHDHIHHH

NHVHRMHATPAY

QSPVNHHHHYHH

STHHRHYHDTLA

```
                                Exon2
NP_001121613.1  DPEP1  ------------MWSGMWLW----------------------------------------
NP_071750.1     DPEP2  MQPSGIEGPGTFGRWPL----LSLLLLLLLLLLQPVTCAYTTPGPPRALTTLGAPRAHTMPGT
sp|Q9H4B8|DPEP3_HUMAN  MQPTGREGSRALSRRYLRRLLLLLLLLLLLLLRQPVTRAETTPGAPRALSTLGSPSLFTTPGV
                                                                                  .
                                        Exon3
NP_001121613.1  ---------PLVAVCTADFFRDEAERIMRDSPVIDGHNDLPWQLLDMFNNRLQDERANLT
NP_071750.1     YAPS------TTLSSPSTQGLQEQARALMRDFFPLVDGHNDLPLVLRQVYQKGLQDV--NLR
sp|Q9H4B8|DPEP3_HUMAN  PSALTTPGLTTPGTPKTLDLRGRAQALMRSFPLVDGHNDLPQVLRQRYKNVLQDV--NLR
                                         ***  ****: **  :::      *** ***
                             Exon4
NP_001121613.1  TLAGTHTN--LRAGPVGGQFWSVVTPCDTQNKDAVRRTLEQMDVVHRMCRMYPETFLYV
NP_071750.1     NFSYGQTSLDRLRDGLVGAQFMSAYVPCQTQDRDALRLTLEQIDLIRRMCASYSELELVT
sp|Q9H4B8|DPEP3_HUMAN  NFSHGQTSLDRLRDGLVGAQFWSASVSCQSQDOTAVRLALEQIDLIHRMCASYSELELVT
                         *     :  **: * *.**: :      ::: ::: .*  :****: :***:***:
                       Exon5                                     Exon6
NP_001121613.1  TSSAGIRQAFREGKVASLIGVEGGHSIDSSLGVLRALYQLGMRYLTLTHSCNTPWADNWL
NP_071750.1     -SAKAL---NDTQKLACLIGVEGECHSLDNSLSILRTFYMLGVRYLTLTHTCNTPWAESSA
sp|Q9H4B8|DPEP3_HUMAN  -SAEGL---NSSQKLACLIGVEGGHSLDSSLSVLRSFYVLGVRYLTLTFTCSTPWAESST
                        **       *    * ****  **:*.** ::* :: :*::*******:.*.*****:*:
                                         Exon7
NP_001121613.1  VDTGDSEPQSQGLSPFGQRVVKELNRLGVLIDLAHVSATMKATLQLSRAPVIFSHSSAY
NP_071750.1     KGVHSFYNNISGLTDFGEKVVAEMNRLGMMVDLSHVSDAVARRALEVSQAPVIFSHSAAR
sp|Q9H4B8|DPEP3_HUMAN  KFRHHMYTNVSGLTSFGEKVVEELNRLGMMIDLSYASDTLIRRVLEVSQAPVIFSHSAAR
                          :    ..** .**::*  *:****::**::.: :: :  *::**********:::
                                      Exon8
NP_001121613.1  SVCASRRNVPDDVLRLVKQTDSLVMVNFYNNYISCTNKANLSQVADHLDHIKEVAGARAV
NP_071750.1     GVCNSARNVPDDILQLLKKNGGVMVSLSMGVIQCNPSANVSTVADHFDHIKAVIGSKFI
sp|Q9H4B8|DPEP3_HUMAN  AVCDNLLNVPDDHILQLLKKNGGIVMVTLSMGVLQCNLLANVSTVADHFDHIRAVIGSEFI
                         **   ****:: *:::::  :** **:*::*: :**..*******:***:* *::: :
                          Exon10                                   Exon11
NP_001121613.1  GFGGDFDGVFRVPEGLEDVSKYPDLIAELLRRNWTEAEVKGALADNLLRVFEAVEQAS--
NP_071750.1     GIGGDYDGAQKPPQGLEDVSTYPVLIEELLSRGWSEEELQGGVLRGNLLRVFRQVQEE
sp|Q9H4B8|DPEP3_HUMAN  GIGGNYDGTGRFPQGLEDVSTYPVLIEELLSRSWSEEELQGGVLRGNLLRVFRQVEKVREE
                       *:**::**:    :*****.**.*:***.*..*:***.**.:*.***** :*:.
```

FIG 20B

NP_001121613.1       NLTALEEPPLDQLGGSRTHYGYSRGASSLH          RHWGLLL        AS
NP_071750.1          NKWQSPLEDKFPDEQLSSSHSDLSRLRQRQSLTSGQELTEIPIHWTAKLPAKWSVSESS
sp|Q9H4B8|DPEP3_HUMAN SRAQSPVEAEFPYGQLSTSHSHLVPQNGHQ------ATHLEVTKQPTNRVPWRRSNAS
                       . *:*  :*  .**. *   *.  ::.                   :*

NP_001121613.1       LAPLVLCLSLL---
NP_071750.1          PHMAPVLAVVATFPVLIWL-
sp|Q9H4B8|DPEP3_HUMAN PYLVPGLVAAATIPTFQWLC
                       :  :  :

Exon2
AAH03492.1           ----------------------MVIIWWFWSLLA-------------
NP_001288133.1       LTGLKGHWV-----LGHGLSVFLLVLLGPSQPLIWTQTKPGFSGASTSSIPRALT
AAH51148.1           PAGLEGPRALGLRPLGHRLSLL--GVLLVPSLWVTCTLTTPSPSSAPTTPEASNATT
                                                             :

Exon3
AAH03492.1           ------------ICASDSFRDQAVAIMRTTPVIDGHNDLPWQLLNLFNNQLLRPDADLNK
NP_001288133.1       KPDISSIPTTPGNPNFPDLRDRARALMQEFPLIDGHNDMPLVLRQFYQNGLQ--DANLRN
AAH51148.1           APGIPNDTATSGVTSDPRLREQALALMRDPPLVDGHNDLPLLLRELFQNLQ-- DVNLRN
                                         : : :**:* :  *::*:* *****:*  *   .::*:

AAH03492.1                      Exon4
                     LAQTHTHSELKAGFVGGQFWSAYMPCDTQNKDAVKRILEQMDVIHRMCQLYPETFMCVT
NP_001288133.1       FTHGQTSLDRLKDGLVGAQFWSAYVPCQTQDRDALRLTLEQIDLIRRICASYSELELVTS
AAH51148.1           FTRGQTNLDRLRDGLVGAQFWSAYIPCQTQDRDAVRLALEQIDLIRRMCSAYPELELVTS
                       : *  . . * *.:.::*:  ***:

Exon5                              Exon6
AAH03492.1           NSSDIQAFRRGKVASLIGVEGGHLIDSSLGVLRTLYHLGMRYLTLTHNCNTRWADNWLV
NP_001288133.1       VK---ALNSTQKLACLIGVEGGHSLDNSLAVLRSPYLLGVRYLTLTHTCNTRWAETSSK
AAH51148.1           AD----GLNNTQKLACLIGVEGGHSLDTSLAVLRSPYELGVRYLTLTPTCSTRRWAESATK
                          .::* *::::*** :*. *: *. * :***** * *.:.**:::  :

FIG. 20C

Legend:
- Signal peptide
- Predicted/potential LSALT binding motif (by reverse biopanning)
- Propeptide (removed from mature form)
- GPI-anchor amidated serine
- Disulfide bond, interchain

```
                        Exon7
AAH03492.1      DRGDDEAESHGLSPFGKRLLNEMNRLGVMIDLSHVSVATMKDALQISRAPVIFSHSSAYS
NP_001288133.1  GVHAFYSSVTGLTSFGEKVVAEMNRLGMMVDLSHVSDAAARRALEVSQAPVIFSHSAARA
AAH51148.1      FRHHFYTNISGLTSFGEKVVEEMNRLGMMIDLSHASDTLVKQTLEVSQAPVIFSHSAARS
                 *::   ::*::***:: ***:******.:::*** *:: : ***.:***:*********

Exon8                                 Exon9
AAH03492.1      LCPHRRNVPDDVLQLVKNTSSLVMVNFFSNFVSCSDSATLPQVADHLDHIKKVAGAGAVG
NP_001288133.1  VCPNARNLPDDLLQLLKKNGGIVMVTFSVGVLPCNPLANVSTVADHFDHIRSVIGSEFIG
AAH51148.1      VCDNLLNIPDDILQLLKKNGGIVMVTLSMGVLQCSLFANVSTVADHFDHIRTVIGSEFIG
                :* :  *:***:**::*:*..:***.:*..*. *. :::**:******:***:.:.. :*

Exon10                                            Exon11
AAH03492.1      LGGDYDGVTMLPVGLEDVSKYPDLIAELLRRNWTETEVRGLLADDVLRVFSEVEQVS
NP_001288133.1  IGGDYDGTKQFPQGLEDVSTYPVLIEELLRRGWNEQELQGILRGNLLRVFRQVEQVRDKS
AAH51148.1      IGGSYDGSRFPQGLEDVSTYPVLIEFLLSRGMDERELQGVLRGNLLRVFRQVEQVREKS
                :** ***.  :* *****.** **.*** *. :  *:: ::*.::****..*****

AAH03492.1      MQSPEEVPITLKELDGSRTYYGYQAHSIHLKTGALVASLASLLFRLHLL----------
NP_001288133.1  KWQSPLEDMIPEEQLDSAHSALRPQKQHPEKNQPETP--EYHILKFSHSKQSPHIVPSL
AAH51148.1      LGQSPVEVKFPERQQSNTHSHLLPQPQEDQHQDTHLKVTKLPNILQRAQAPPHPLPGL
                  ***      :     .   :      ::  :*::  .   :*

AAH03492.1      ----------
NP_001288133.1  ATVATLLGLTV
AAH51148.1      MATLTSLAIILWLCCSGHRRAV

Murine Melanoma Cells

Murine melanoma cells

Murine sarcoma cells

Breast Cancer Liver Metastasis

Human melanoma 70W Lung metastasis

Human osteosarcoma 143B Lung metastasis

Human osteosarcoma 143B Lung metastasis

Murine melanoma B16-F10 lung metastasis

Control

LSALT

Murine breast cancer E0771.LMB lung metastasis

DPEP-1 BINDING AGENTS AND METHODS OF USE

CROSS REFERENCE TO RELATED APPLICATION

This application claims priority to U.S. Provisional Patent Application No. 62/773,733, filed on Nov. 30, 2018, which is incorporated herein in its entirety.

SEQUENCE LISTING

The instant application contains a Sequence Listing which has been filed electronically in ASCII format and is hereby incorporated by reference in its entirety.

FIELD

Disclosed herein are DPEP-1 binding compositions(e.g., peptides) and pharmaceutical compositions containing the same. Also disclosed are methods for using and manufacturing such peptides and pharmaceutical compositions, as well as methods for screening for DPEP-1 binding compositions.

BACKGROUND

Inflammation is a host defense reaction to harmful stimuli. Acute inflammation is characterized by redness, heat, swelling, and pain. The primary objectives of inflammation are to localize and eradicate the irritant and promote repair of the surrounding tissue. In most instances, inflammation is a necessary and beneficial process.

The inflammatory response involves three major stages: first, dilation of arterioles to increase blood flow; second, microvascular structural changes and escape of plasma proteins from the bloodstream; and third, leukocyte transmigration through endothelium and accumulation at the site of injury. Leukocyte transendothelial migration (TEM) is a key step in their recruitment to sites of inflammation, injury, and immune reactions. The emigration of neutrophils to sites of inflammation is thought to require intercellular adhesion.

Inflammation can be acute or chronic. Failure to resolve the harmful stimuli prompting acute inflammation can lead to chronic inflammation, and some stimuli are likely to prompt immediate chronic inflammation. In some instances, inflammation results in secondary or chronic damage. Inflammation in a tumor microenvironment has also been implicated in cancer acceleration and tumor metastasis (Wu et al., Cell Cycle. 2009 Oct 15;8(20):3267-73, Geng et al., PLoS One. 2013;8(1):e54959). The presence of pro-inflammatory molecules enables malignant cancer cells to adhere to the endothelial wall, leading to metastasis. Pro-inflammatory cytokines induce proliferation and aggregation of cancer cells, triggering other cancer cells to secrete more cytokines, resulting in a positive feedback loop. The role of adhesion molecules in acute and chronic inflammation is an area of study necessary for development of methods to control inflammation by modulating or blocking leukocyte adhesion to the endothelium.

Anti-inflammatory agents function as blockers, suppressors, or modulators of the inflammatory response. Tissue-specific control of inflammation is sometimes desirable to modulate inflammation in one tissue while maintaining the response in other tissues. Anti-inflammatory agents are used to treat various acute and chronic conditions. Most people have no trouble taking these agents, however some people develop side-effects which can be serious. In some groups, these medicines are prescribed with caution and only where there are no alternatives and at the lowest doses and durations necessary.

Recognition of non-self-molecular patterns by pattern recognition receptors is a cornerstone of innate immunity. Study of the innate immune system has also revealed the existence of dinucleotide receptors for sensory and signaling that activate inflammatory responses (Cai et al., 2014). The dinucleotide receptor STING is used to induce type I IFNs (Ishikawa 2009). These systems are pervasive in mammals and other animals. If there are dinucleotide receptors, there are likely dipeptide receptors that function in a similar manner. Pro-inflammatory dipeptide receptor cellular signaling systems provide another therapeutic approach to modulate inflammation and treat acute and chronic inflammation-mediated diseases.

Variations of the sequence of a natural protein may be characterized as neutral mutations (mutations that do not lead to altered structure or function of the protein), structural mutations (mutations that lead to altered structure of the protein, but not necessarily altered function), or functional mutations (mutations that lead to loss or gain of function of the protein). Such variations may result in differences within a population and/or result in diseases, and therefore would provide useful information for evolutionary analysis, and medical analysis of the root cause of the disease. Further, it would allow more accurate evolutionary analysis by identifying homologous and analogous mutations to both structure and function. Understanding which mutations are neutral, structural, or functional will allow for more accurate diagnostics and aid in the design of more effective treatments.

There remains a need for additional therapeutic compounds for reducing or blocking inflammation as current therapeutics, in particular because many of the current approaches cannot adequately treat some of the more extreme cases of inflammation. What is therefore needed are new compositions to function as blockers, suppressors, or modulators of the inflammatory response. What is also needed are novel targets and methods of modulating inflammation via these targets.

SUMMARY

Disclosed herein are DPEP-1 binding compositions (e.g., peptides) as well as pharmaceutical compositions comprising the same. Also disclosed are methods of using and making such DPEP-1 compositions, as well as methods for screening for screening for DPEP-1 binding compositions.

In a first aspect, a composition is disclosed comprising an effective amount of a DPEP-1 binding peptide, wherein the DPEP-1 binding peptide comprises (i) an amino acid sequence comprising LSALT and (ii) one more glycine residues at the N-terminus and/or C-terminus.

In one embodiment, the peptide comprises two or more glycine residues at the N-terminus.

In one embodiment, the peptide comprises three more glycine residues at the N-terminus.

In a particular embodiment, the amino acid sequence in (i) comprises

LSALTPSPSWLKYKAL. (SEQ ID NO: 1)

In a particular embodiment, the DPEP-1 binding peptide is selected from the group consisting of GLSALTPSPSWLKYKAL (SEQ ID NO:2), GGLSALTPSPSWLKYKAL (SEQ ID NO:3), GGGLSALTPSPSWLKYKAL (SEQ ID NO:4) and GGGGLSALTPSPSWLKYKAL (SEQ ID NO:4).

In an alternate embodiment, the DPEP-1 binding peptide has 1, 2, 3, 4, or 5 amino acid residues removed from the N-terminus and/or C-terminus of the LSALT peptide sequence.

In a particular embodiment, the DPEP-1 binding peptidecomprises the amino acid sequence LTPSPSWLKYKAL (SEQ ID NO:5).

In a particular embodiment, the composition further comprises a pharmaceutically acceptable carrier.

In a second aspect, a DPEP-1 binding peptide is disclosed herein comprising an amino acid sequence comprising KHMHWHPPALNT (SEQ ID NO:6, "neogenin-mimetic peptide")In one embodiment, the amino acid sequence further comprises one or more additional amino acid residues at the N- or C-terminus.

In a third aspect, disclosed herein is a DPEP-1 binding inhibiting peptide comprising an amino acid sequence comprising IPKXPXXXP (SEQ ID NO:7) motif.

In one embodiment, the amino acid sequence further comprises one or more additional amino acid residues at the N- or C-terminus.

In a fourth aspect, disclosed herein is a DPEP-1 binding inhibiting peptide comprising an amino acid sequence comprising HIPKSPIQIPII (SEQ ID NO:8)

In one embodiment, the amino acid sequence further comprises one or more additional amino acid residues at the N- or C-terminus.

Optionally, the DPEP-1 binding peptides may have one or more modifications. In one embodiment, the one or more peptide modifications are selected from the group consisting of internal modifications, N-terminal modifications or C-terminal modifications.

In one embodiment, the DPEP-1 binding peptide comprises one or D-amino acids, modified amino acids, amino acid analogs or combinations thereof.

In one embodiment, the DPEP-1 binding peptide comprises one or more amino acid analogs selected from the group consisting of β-alanine, norvaline, norleucine, 4-aminobutyric acid, orithine, hydroxyproline, sarcosine, citrulline, cysteic acid, cyclohexylalanine, 2-aminoisobutyric acid, 6-aminohexanoic acid, t-butylglycine, phenylglycine, o-phosphoserine, N-acetyl serine, N-formylmethionine, 3-methylhistidine In certain embodiments, the DPEP-1 peptide is modified by methylation, amidation, acetylation, acetylation, prenylation, pegylation or combinations thereof.

In a fifth aspect, a method is disclosed for reducing inflammation in vivo, comprising (i) administering a composition disclosed herein to a cell, thereby reducing inflammation.

In one embodiment, inflammation is characterized by a profile of inflammatory markers selected from IL-12, IP-10, IL-1β, IL-5, GM-CSF, IFNγ, or IL-1α. In a particular embodiment, the method results in modification in the level of one or more of the inflammatory markers.

In a sixth aspect, a method is disclosed for treating a disease or disorder in a subject in need thereof, comprising (i) administering a composition disclosed herein to the subject, thereby treating the disease or disorder.

In one embodiment, the disease or disorder is associated with leukocyte recruitment, inflammation or a combination thereof.

In a particular embodiment, the disease or disorder is acute kidney injury.

In a particular embodiment, the disease or disorder is sepsis.

In a particular embodiment, the disease or disorder is tumor metastasis.

In one embodiment, the disease or disorder is a ischemia-reperfusion injury-related disorder. In a particular embodiment, the subject in need thereof is an organ donor or organ recipient.

In one embodiment, the method further comprises identifying the subject in need of treatment by performing a diagnostic test.

In a seventh aspect, disclosed herein is a method for screening for compositions (e.g., peptides) that bind to DPEP-1, comprising: (a) screening a library of test compounds (e.g., peptides) for their ability to bind to DPEP-1 and (b) selecting compounds that show selective binding affinity for DPEP-1.

In one embodiment, the method further comprises (c) testing compounds that show selecting binding affinity for DPEP-1 to identify compounds with for inflammation-reducing activity in vivo, and (d) selecting compounds that show inflammation-reducing activity in vivo.

In an eight embodiment, disclosed herein is a kit comprising a composition disclosed herein. In one embodiment, the kit further comprises a pharmaceutically acceptable carrier.

These and other objects and features of the invention will become more fully apparent when the following detailed description of the invention is read in conjunction with the accompanying drawings.

BRIEF DESCRIPTION OF THE DRAWINGS

FIG. 12A and FIG. 12B demonstrate[[s]] leukocyte recruitment to the kidney in response to ischemia-reperfusion injury (IRI).

FIG. 13A and B represent the imaging data from FIG. 12A and B in graphical form.

FIG. 15B is a graphical representation of peptide binding data in FIG. 15A. FIG. 15C provides a graph that demonstrates LSALT modified with glycine spacers can inhibit endotoxemia induced kidney inflammation. Inflammation in the kidney was induced by intravenous injection of LPS (O111:B4, 5 mg/kg) into volume depleted LysM$^{gfp/gfp}$ mice. Mice were pretreated with either control peptide (Scram. LSALT) or tri-glycine LSALT (G2) 5 min. prior to LPS treatment. Kidneys were assessed for inflammation 4 hours post LPS treatment. Inflammation was quantified by manual counting of monocyte adhesion in single microscopy fields (n=3-6 fields/group; *: p=0.02).

FIGS. 16 A-B shows that alanine substitutions in LSALT affect binding affinity. FIG. 16A provides a table of how LSALT was modified at each amino acid position with an alanine substitution to determine which amino acid residues affect binding to DPEP1.

FIGS. 17 A-C show LSALT metabolized in blood can still bind to DPEP1. FIG. 17A demonstrates that LSALT peptide is metabolized in whole blood into smaller fragments in whole blood. LSALT peptide (50 μg/mL) was incubated in whole human blood (citrate or K2 EDTA treated) for various timepoints up to 120 min. Plasma was separated for each sample and phosphoric acid added to stabilize the peptide at each timepoint. Samples were assessed for LSALT and its' metabolites using LC/MS. LSALT metabolites were identified using PEAKS X and database searches against LSALT and the human proteome.

FIGS. 19A-C shows novel DPEP-1 binding peptides. Using commercially available recombinant human DPEP1 (Creative Biomart, His tagged) attached to nickel-coated agarose beads, hDPEP1 was biopanned using PhD 12 phage display library. FIG. 19A shows 48 plaques that were sequenced with several candidate hits including neogenin-mimetic peptides. FIG. 19B provides images of phage hits tested for DPEP1 binding. Using DPEP1 and DPEP2 transfected Cos 1 cells, the phage hits were backscreened for binding specificity. KHMHWHPPALNT showed the brightest binding to DPEP1 transfected cells. FIG. 19C demonstrates inhibition of neogenin-mimetic peptides prevents adhesion of neutrophils. Functional activity of neogenin-mimetic peptide was tested using a static neutrophil adhesion assay to recombinant hDPEP1, Cos Functional activity was tested using a static neutrophil adhesion assay to recombinant hDPEP1, Cos 1 transfected cells, and LPS activated endothelial cells (HLMVEC) (FIG. 19C). Both synthetically generated peptides of the neogenin-mimetic peptide phage hit sequence (NeoH) and peptides with the exact neogenin-mimetic sequence sequence (NeoEx) were able to inhibit neutrophil adhesion in all three systems. Additionally, anti neogenin antibody was also able to inhibit neutrophil adhesion to endothelial cells.

FIGS. 20A-E identifies the sequence that LSALT is bound to. FIG. 20A shows the reoccurring IPK motif in plaques sequenced after biopanning. LSALT peptide was fixed to a agarose beads and the PhD 12 phage display library was used to biopan against it. The motif IPKxPxxxP was found in 9 of the 29 sequenced plaques. FIG. 20B-D shows the IPK motif in human and mouse DPEP1. Peptide alignment analysis demonstrated that the IPK motif is present in only human and mouse DPEP1 but not in DPEP2 or DPEP3. FIG. 20E provides a graph demonstrating IPK inhibition prevents neutrophil adhesion. One of the IPK phage hits (HIPKSPIQIPII) was able to inhibit neutrophil adhesion in LPS stimulated human endothelial cells. The IPK peptide may interfere with DPEP1-mediated leukocyte adhesion by binding to the neutrophil ligand that interacts with DPEP1.

FIG. 21A demonstrates human melanoma cells (70 W) bind specifically to DPEP1. COS-1 cells were either vehicle treated (control) or transfected with DPEP1, DPEP2, or DPEP3. Human melanoma cells were co-cultured with transfected cells and quantified. FIG. 21B-C shows LSALT inhibits binding of murine cancer cells to DPEP1. COS-1 cells were either vehicle transfected (control) or DPEP1 transfected and co-cultured with either murine melanoma cells (B16-F10) or murine breast cancer cells (E0771.LMB) in the absence or presence of LSALT (50 μM). Murine cancer cells bound to transfected COS-1 cells were quantified after co-culture.

FIGS. 23 A-I demonstrates LSALT reduces tumor burden in livers and lungs of animals injected with metastatic cancer cells.

FIGS. 24 A-C demonstrates that human melanoma cells bind to human DPEP1.

DETAILED DESCRIPTION

I. Definitions

Figure 1A:
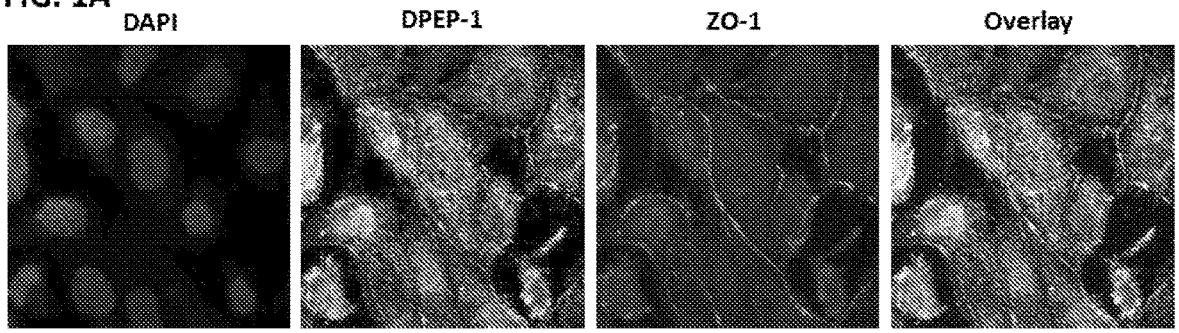
FIG. 1A provides representative photomicrographs of renal tubular epithelial cells (TEC) isolated and cultured from human kidney nephrectomies and labeled with DPEP-1 and ZO-1 (a TEC surface marker).

Where a term is provided in the singular, the inventors also contemplate aspects of the invention described by the plural of that term. As used in this specification and in the appended claims, the singular forms "a", "an" and "the" include plural references unless the context clearly dictates otherwise, e.g., "a peptide" includes a plurality of peptides. Thus, for example, a reference to "a method" includes one or more methods, and/or steps of the type described herein and/or which will become apparent to those persons skilled in the art upon reading this disclosure.

The term "administer", "administering" or "administered" means the act of giving an agent or therapeutic treatment to a physiological system (e.g., a subject or in vivo, in vitro, or ex vivo cells, tissues, and organs).

The term "affinity", as used herein, refers to the strength of the sum total of noncovalent interactions between a single binding site of a molecule and its binding partner. Unless indicated otherwise, as used herein, "binding affinity" refers to intrinsic binding affinity which reflects a 1:1 interaction between members of a binding pair. The affinity of a molecule X for its partner Y can generally be represented by the dissociation constant (Kd). Affinity can be measured by common methods known in the art.

The term "amino acid" refers to naturally occurring amino acids, as well as non-naturally occurring or non-standard amino acids such as amino acid analogs, synthetic amino acids, and amino acid mimetics. These amino acids may be in the L- or D-(isomeric) configuration, or may include both dextrorotary forms. Amino acids that have been incorporated into peptides are termed "residues". Amino acids may be referred to herein by either the commonly known three letter symbols or by the one-letter symbols recommended by the IUPAC-IUB Biochemical Nomenclature Commission. The following amino acid definitions are used throughout the specification: Alanine: Ala (A) Arginine: Arg (R) Asparagine: Asn (N) Aspartic acid: Asp (D) Cysteine: Cys (C) Glutamine: Gln (O) Glutamic acid: Glu (E) Glycine: Gly (G) Histidine: H is (H) Isoleucine: Ile (I) Leucine: Leu (L) Lysine: Lys (K) Methionine: Met (M) Phenylalanine: Phe (F) Proline: Pro (P) Serine: Ser (S) Threonine: Thr (T) Tryptophan: Trp (W) Tyrosine: Tyr (Y) Valine: Val (V).

The term "binding agent", as used herein, refers to a ligand (e.g., a peptide) that forms a complex with a receptor. The ligand may be selective or non-selective. The ligand may be an agonist (partial or full), antagonist (i.e., blocks the action of an agonist), an inverse agonist (i.e., exerts the opposite action of an agonist) or an allosteric modulator. Antagonists may be competitive (i.e., bind at the same site as the agonist) or non-competitive antagonists (i.e., binding permanently at the same site as the agonist or binding at an allosteric site—a site other than the active site).

The term "diagnosed", "diagnostic" or "diagnosed" means identifying the presence or nature of a pathologic condition. Diagnostic methods include observations and assays, and differ in their sensitivity and specificity. The "sensitivity" of a diagnostic observation or assay is the percentage of diseased individuals who test positive (percent of "true positives"). Diseased individuals not detected by the observation or assay are "false negatives." Subjects who are not diseased and who test negative in the observation or assay are termed "true negatives." The "specificity" of a diagnostic observation or assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

As used herein, the term "effective amount" refers to the amount of a therapy (e.g. a prophylactic or therapeutic agent) which is sufficient to effect beneficial or desired results, including clinical results. An effective amount can be administered in one or more administrations.

As used herein, the term "inflammatory disease" refers to diseases (treatable or preventable with compounds described herein) including, but not limited to, a. leukocyte recruitment, adhesion or activation and other disorders that involve neutrophils, monocytes, lymphocytes or macrophages, b. diseases involving the pathological production of inflammatory cytokines (e.g. TNF-α, interleukin (IL)-1β, IL-2, IL-6) c. activation of nuclear factors that promote transcription of genes encoding inflammatory cytokines. Examples of these nuclear transcription factors include but are not restricted to: nuclear factor-κB (NFκB), activated protein-1 (AP-1), nuclear factor of activated T cells (NFAT).

The term "ischemia reperfusion injury", as used herein, refers to the damage caused first by restriction of the blood supply to a tissue (ischemia) followed by a resupply of blood (reperfusion) and the attendant generation of free radicals, inflammation and cell death resulting in organ injury and dysfunction. In transplantation scenarios, ischemia reperfusion injury negatively affects allograft function.

The term "isolated", as used herein, refers to a material is removed from its original environment (e.g., the natural environment, if it is naturally occurring). For example, a naturally-occurring peptide present in a living animal is not isolated, but the same polynucleotide peptide, separated from some or all of the coexisting materials in the natural system, is isolated.

The term "pharmaceutically acceptable carrier" refers to any such carriers known to those skilled in the art to be suitable for the particular mode of administration. For example, the term "pharmaceutically acceptable carrier" includes any and all solvents, dispersion media, coatings, antibacterial and antifungal agents, isotonic and absorption delaying agents and the like, that may be used as a media for a pharmaceutically acceptable substance. In addition, the active materials can also be mixed with other active materials that do not impair the desired action, or with materials that supplement the desired action, or have another action.

The term "pharmaceutically acceptable salt" as used herein refers to salts which are known to be non-toxic and are commonly used in the pharmaceutical literature. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenylsubstituted alkanoic acids, hydroxyalkanoic and hydroxyalkandioic acids, aromatic acids, aliphatic and aromatic sulfonic acids, may also be used. Such pharmaceutically acceptable salts include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, beta-hydroxybutyrate, chloride, cinnamate, citrate, formate, fumarate, glycolate, heptanoate, lactate, maleate, hydroxymaleate, malonate, mesylate, nitrate, oxalate, phthalate, phosphate, monohydrogenphosphate, dihydrogenphosphate, metaphosphate, pyrophosphate, propionate, phenylpropionate, salicylate, succinate, sulfate, bisulfate, pyrosulfate, sulfite, bisulfate, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like.

The term "prevent" or the equivalent, e.g., "prevention" or "preventing", refers to reducing the occurrence of the disorder or condition in the treated sample relative to an untreated control sample, or delaying the onset or reducing the severity of one or more symptoms of the disorder or condition relative to the untreated control sample. As used herein, preventing ischemia-reperfusion injury includes preventing oxidative damage or preventing mitochondrial permeability transitioning, thereby preventing or ameliorating the harmful effects of the loss and subsequent restoration of blood flow to an effected organ. Preventing does not mean that a subject never develops the condition later in life—only that the probability of occurrence is reduced.

The terms "reducing," "reduce," or "reduction" in the context of a disease or condition herein refers to a decrease in the cause, symptoms, or effects of a disease or condition. Therefore, in the disclosed methods, "reducing" can refer to a 10%, 20%, 30%, 40%, 50%, 60%, 70%, 80%, 90%, or 100% decrease, or any value or range there between, in the amount of injury due to reperfusion.

The term "subject" or "patient" or synonym thereto, as used herein includes all members of the animal kingdom, especially mammals, including human. The subject or patient is suitably a human.

The term "transplantation" is meant a surgical procedure by which a cell, tissue or organ is transferred from a donor subject to a recipient subject or from one part of the body to another in the same subject. The "donor subject" or "donor" is the subject who gives blood, cells, tissues, or an organ for another subject by blood transfusion or an organ transplant. The donor subject is a human or another mammal. The "recipient subject" or "recipient" is the subject who receives blood, cells, tissues, or an organ from another subject by blood transfusion or an organ transplant.

As used herein, the terms "treat", "treatment" and "treating" refer to the prevention, reduction or amelioration of the progression, severity, and/or duration of at least one pathology and/or symptom of any condition or disease. The term "treatment" or "treating" refers to any administration of a compound disclosed herein and includes (i) inhibiting the disease, or the disease state in an individual that is experiencing or displaying the pathology or symptomatology of the disease, or the disease state (i.e., arresting further development of the pathology and/or symptomatology) or (ii) ameliorating the disease in an individual that is experiencing or displaying the pathology or symptomatology of the disease, or the disease state (i.e., reversing the pathology and/or symptomatology). The term "controlling" includes preventing, treating, eradicating, ameliorating or otherwise reducing the severity of symptoms of the disease, or the disease state.

As is relates to cancer, the terms "treat", "treatment" and "treating" refer to the reduction or amelioration of the progression, severity, and/or duration of cancer, particularly a solid tumor, or one or more symptoms thereof that results from the administration of one or more therapies (e.g., one or more prophylactic and/or therapeutic agents). In exemplary embodiments, treatment of a solid tumor refers to one or more of (i) reducing the number of cancer cells; (ii) increasing tumor cell apoptosis; (iii) reducing tumor size; (iv) reducing tumor volume; (v) inhibiting, retarding, slowing to some extent, and preferably stopping cancer cell infiltration into peripheral organs; (vi) inhibiting (e.g., slowing to some extent and preferably stopping) tumor metastasis; (vii) inhibiting tumor growth; (viii) preventing or delaying occurrence and/or recurrence of a tumor; (ix) reduction of a cancer marker that is associated with the presence of cancer; and/or (ix) relieving to some extent one or more of the symptoms associated with the cancer. "Treatment" can also mean prolonging survival as compared to expected survival if not receiving treatment. Standard methods can be used to measure the magnitude of this effect, such as in vitro assays with purified enzyme, cell-based assays, animal models, or human testing. For example, an immunohistochemical analysis of a cancer tumor of the patient may show a significant increase in tumor cell apoptosis when the composition disclosed herein is administered to the patient. When referring to a type of cancer that normally manifests as a solid tumor, a "clinically detectable" tumor is one that is detectable on the basis of tumor mass; e.g., by procedures such as CAT scan, MR imaging, X-ray, ultrasound or palpation, and/or which is detectable because of the expression of one or more cancer-specific antigens in a sample obtainable from a patient.

II. DPEP-1

DPEP-1, also known as renal dipeptidase, microsomal dipeptidase, or dehydropeptidase-1 and currently classified as EC 3.4.13.19 (previously EC 3.4.13.11), is a plasma membrane glycosyl phosphatidylinositol-anchored glycoprotein (Keynan et al., in Hooper (Ed.) Zinc Metalloproteases in Health and Disease Taylor and Francis, London pages 285-309 (1996), which is incorporated herein by reference). This zinc metalloprotease, which is expressed mainly in lung and kidney brush border, is involved in vivo in renal metabolism of glutathione and in pulmonary metabolism of peptidyl leukotrienes. In addition, DPEP-1 is the only known example of a mammalian beta-lactamase and is also involved in the metabolism of glutathione and its conjugates, as well as leukotriene D4. DPEP-1 forms a disulfide-linked homodimer, with the molecular weight of the monomer ranging from about 48 to 59 kDa depending on the species of origin (Keynan et al., Biochem. 35:12511-12517 (1996), which is herein incorporated by reference; see, also, Example IVB).

Dipeptidase expression has been detected in several tissues although it is expressed mainly in lung and kidney. There have been reports of low levels of DPEP-1 activity in total extracts from liver, spleen, small intestine and brain, while others have found no detectable activity in these organs. In the mouse, four distinct DPEP-1 mRNAs are present, and they are differentially expressed in several organs (Habib et al., J. Biol. Chem. 271:16273-16280 (1996)). Organ-specific differences in the nature and extent of pig DPEP-1 N-linked glycosylation also have been reported (Hooper et al., Biochem. J. 324:151-157 (1997)).

In the kidney, DPEP-1 expression is restricted to epithelial cells in the brush border region of the proximal tubules and the endothelial cells of the peritubular capillaries. In the lung, DPEP-1 expression has been detected in many cell types including endothelial cells as well as epithelial cells of the conducting airways, alveolar ducts, capillaries, and the basement membrane of alveoli and terminal bronchioles (Habib et al., supra, 1996); Inamura et al., Prostaglandins Leukotrienes and Essential Fatty Acids 50:85-92 (1994)). DPEP-1 expression also has been observed on endothelial cells of submucosal microvessels in the human trachea (Yamaya et al., Resp. Physiol. 111:101-109 (1998)). The level of DPEP-1 activity is highest in lung (Hirota et al., Eur. J. Biochem. 160:521-525 (1986); Habib et al., Proc. Natl. Acad. Sci. USA 95:4859-4863 (1998)). This expression pattern correlates with the strong lung homing of molecules such as GFE-1.

While not to be bound by a particular theory, it is believed that the DPEP-1 receptor functions as a leukocyte adhesion molecule or a tumor cell adhesion molecule expressed on vascular endothelium, or other parenchymal cells such as the kidney tubular epithelium (Choudhury et al. 2019, Cell 178, 1205-1221). Adhesion molecules are involved in the recruitment process, which are surface bound glycoprotein molecules expressed on leukocytes and/or endothelial cells. A key step in leukocyte recruitment is firm adhesion of leukocytes on the surface of the endothelium, which positions the leukocyte to migrate into the vessel wall through a sequence of adhesion and activation events to exerts its effects on the inflamed site. DPEP-1 could also function as a peptide detection system during organ injury or infection. One such peptide detection system is the so-called pattern recognition receptors (PRR) to detect key molecular signatures of invading pathogens, i.e., pathogen-associated molecular patterns (PAMPS), or endogenous damage-associated molecular patterns (DAMPs) thereby triggering the innate immune system (Janeway, C, et al., Annu. Rev. Immunol, 20 (2002), pp. 197-216). Examples of PRR are (toll-like receptors) TLRs, which detect bacterial or viral products such as LPS, (TLR4) or peptidoglycans (TLR2) (Bell, J. K. et al., Trends Immunol, 24 (2003), pp. 528-533).

TLRs are transmembrane receptors that recognize pathogen-associated molecular patterns (PAMPs) through leucine-rich repeats (LRRs) in their extracellular domains that are implicated in ligand binding and auto-regulation (Kawai et al, Cell Death Differ. 13, 816-825, 2006). TLRs recognize microbial structures in the earliest phase of the host defense response and induce the expression of many immune and inflammatory genes, the products of which are tailored to drive the immune mechanisms necessary for eliminating the invading pathogen. TLRs have also been implicated in the recognition of damage-associated molecular patterns (DAMPs) and are becoming increasingly recognized as regulators of tumor-promoting inflammation and promoters of tumor survival signals. Other activators of such cellular pathways may provide effective therapeutic targets to treat pathogen and damage-associated cellular inflammation.

As used herein, the terms "dipeptidase", and "membrane dipeptidase" are synonymous with "DPEP-1" and refers to the enzyme currently classified as EC 3.4.13.19 (previously EC 3.4.13.11) and also known as renal or microsomal dipeptidase or dehydropeptidase-1.

The term "selectively inhibits", as used herein in reference to a DPEP-1 enzymatic activity, means that the binding agent decreases DPEP-1 activity in a manner that is selective for the DPEP-1 enzyme as compared to related but different enzymes such as other proteases. Thus, an DPEP-1 binding agent is distinct from a non-specific inhibitor of, for example, zinc metalloproteases. Thus, a DPEP-1 binding agent can selectively decrease DPEP-1 activity while having little or no effect on the activity of, for example, dipeptidyl peptidase IV. In one embodiment, the binding agent is a competitive inhibitor to prevent binding to DPEP-1.

The term "selectively binds", as used herein in reference to a DPEP-1 binding agent, means that the binding agent decreases DPEP-1-mediated leukocyte recruitment in a manner that is selective for the DPEP-1 receptor as compared to related but different receptors. DPEP-1 binding agent also refers to decreasing DPEP-1-mediated leukocyte recruitment where the DPEP-1 acts as an adhesion molecule for leukocytes or tumor cells independent of its enzymatic activity. Thus, an DPEP-1 binding agent can selectively decrease DPEP-1-mediated leukocyte recruitment while having little or no effect on the activity of, for example, dipeptidyl peptidase IV. In one embodiment, the binding agent is a competitive or non-competitive inhibitor to prevent binding to DPEP-1.

In one embodiment, the DPEP-1 binding agent disclosed herein is an antagonist of the DPEP reception, i.e., blocks or dampens a biological response by binding to and blocking the receptor so as to disrupt the interaction and inhibit the function of an agonist or inverse agonist. In a particular embodiment, the DPEP-1 binding agent is a competitive antagonist, i.e., competes with an agonist for the active site. In another particular embodiment, the DPEP-1 binding agent is a non-competitive antagonist, i.e., binds at a site other than the active site.

The term specific binding, as used herein, includes both low and high affinity specific binding. Specific binding can be exhibited, for example, by a low affinity DPEP-1-binding molecule having a Kd for membrane dipeptidase of about $10^{-4}$ M to about $10^{-7}$ M. Specific binding also can be exhibited by a high affinity DPEP-1-binding molecule, for example, a DPEP-1-binding molecule having a Kd for membrane dipeptidase of at least about $10^{-7}$ M, at least about $10^{-8}$ M, at least about $10^{-9}$ M, at least about $10^{-10}$ M, or at least about $10^{-11}$ M or $10^{-12}$ M or greater. A DPEP-1-binding peptide including an LSALT peptide, where $X_1$ and $X_2$ each is 1 to 10 independently selected amino acids, can have, for example, a Kd for membrane dipeptidase of about $2\times10^{-5}$ M to 10 M, for example, a Kd of about $10^{-6}$ to $10^{-7}$ M. Both low and high affinity DPEP-1-binding molecules that selectively bind to lung or kidney endothelium can be useful in the methods described herein.

III. DPEP-1 Binding Compositions

Binding or blocking DPEP-1 has utility for reducing inflammation-mediated diseases in lung and kidney, for example, during sepsis or acute kidney injury. Binding to or blocking DPEP-1 also has utility for reducing tumor metastasis. Disclosed herein are compositions that bind to or block DPEP-1, including, but not limited to, peptides.

A. DPEP-1 Binding Peptides

Disclosed herein are peptides that bind to DPEP-1. Variants and modified embodiments of these binding peptides that are capable of being used in these methods are also provided. In one embodiment, the peptides modulate the activity of DPEP-1 and more particularly, inhibit the activity of DPEP-1 either competitively or non-competitively.

Using an unbiased combinatorial phage in vivo biopanning approach, a specific peptide-displaying-phage was isolated that localized to the liver and lungs of animals treated with a pro-inflammatory stimulus and blocks leukocyte recruitment. This phage and its corresponding displayed peptide (N-LSALTPSPSWLKYKAL called LSALT or Metablok,)(SEQ ID NO:1) were also found to dramatically reduce tumor burden in the livers or lungs of animals injected with a tumor cell line. LSALT is capable of binding to DPEP-1 and reducing the inflammatory profile of a tissue thereby providing several therapeutically useful actions. The peptide also reduced neutrophil recruitment to the liver in a mouse model of sepsis. The LSALT peptide (called LSALT or Metablok; SEQ ID NO:1), as well as variants and modified versions thereof are described in U.S. Pat. No. 9,464,114.

In some embodiments, the DPEP-1 binding peptide contains one or more modifications to increase protease resistance, serum stability and/or bioavailability. In some embodiments, the modification is selected from pegylation, acetylation, glycosylation, biotinylation, prenylation or substitution with D-amino acid and/or un-natural amino acid, and/or cyclization of the peptide.

In certain embodiments, the DPEP-1 binding peptide contains one or more L-amino acids, D-amino acids, and/or non-standard amino acids.

In various embodiments, the DEP-1 binding peptide further comprises one or more amino acid residues or analogues at the C-terminus, the N-terminus or both the C-terminus and the N-terminus. Preferably the activity bearing sequence of the peptide is not appreciably impacted by the addition of these additional amino acid(s).

In another embodiment, the DEP-1 binding peptide further comprises 1, 2, 3, 4, or 5 amino acid residues at the N-terminus of the peptide sequence.

In various embodiments, the peptide is selected from X-peptide, XX-peptide, XXX-peptide, XXXX-peptide, or XXXXX-peptide where X is any naturally-occurring amino acid or where X is an unconventional amino acid or amino acid analog as described herein and known to those of skill in the art.

In another embodiment, the DPEP-1 binding peptide further comprises 1, 2, 3, 4, or 5 amino acid residues at the C-terminus of the LSALTPSPSWLKYKAL(SEQ ID NO:1) sequence and is selected from peptide-X, peptide-XX, peptide-XXX, peptide-XXXX, or peptide-XXXXX where X is any naturally-occurring amino acid or where X is an unconventional amino acid or amino acid analog as described herein and known to those of skill in the art.

In one embodiment, the DPEP-1 binding peptide further comprises 1, 2, 3, 4, or 5 amino acid residues at the N-terminus and C-terminus of the peptide and is selected from X-peptide-X, X-peptide-XX, X-peptide-XXX, X-peptide-XXXX, X-peptide-XXXXX, XX-peptide-X, XX-peptide-XX, XX-peptide-XXX, XX-peptide-XXXX, XX-peptide-XXXXX, XXX-peptide-X, XXX-peptide-XX, XXX-peptide-XXX, XXX-peptide-XXXX, XXX-peptide-XXXXX, XXXX-peptide-X, XXXX-peptide-XX, XXXX-peptide-XXX, XXXX-peptide-XXXX, XXXX-peptide-XXXXX, XXXXX-peptide-X, XXXXX-peptide-XX, XXXXX-peptide-XXX, XXXXX-peptide-XXXX, or XXXXX-peptide-XXXXX, where X is any naturally-occurring amino acid or where X is an unconventional amino acid or amino acid analog as described herein and known to those of skill in the art.

Disclosed herein are compositions comprising an effective amount of a DPEP-1 binding peptide, wherein the DPEP-1 binding peptide can be an LSALT peptide or derivative or fragment thereof.

In one embodiment, the DPEP-1 binding peptide comprises the amino acid sequence LSALTPSPSWLKYKAL (SEQ ID NO:1). In one embodiment, the peptide comprises an additional 1, 2, 3, 4, or 5 amino acid residues at the N-terminus and/or C-terminus of the peptide sequence. In a specific embodiment, the peptide comprises an additional 1, 2, 3, 4, or 5 amino acid residues at the N-terminus. In one embodiment, the peptide comprises additional glycine residues at the N-terminus of the LSALT peptide (SEQ ID NO:1). In another embodiment, at least one glycine residue is at the N-terminus of the LSALT peptide. In another embodiment, at least two glycine residues are at the N-terminus of the LSALT peptide. In a further embodiment, at least three glycine residues are at the N-terminus of the LSALT peptide. In a particular embodiment, the peptide is selected from GLSALTPSPSWLKYKAL (SEQ ID NO:2), GGLSALTPSPSWLKYKAL (SEQ ID NO:3), or GGGL-SALTPSPSWLKYKAL (SEQ ID NO:4). In a specific embodiment, the peptide is GGGLSALTPSPSWLKYKAL (SEQ ID NO:4).

In a further embodiment, the peptide comprises a LSAL-TPSPSWLKYKAL (SEQ ID NO: 1) wherein the peptide is substituted with one or more D-amino or L-amino acids. In another embodiment, the peptide comprises one or more modifications selected from the group consisting of modified amino acids, amino acid analogs or combinations thereof.

In other embodiments, DPEP-1 binding peptides provided herein can 1, 2, 3, 4, or 5 amino acid residues removed from the N-terminus and/or C-terminus of the LSALT peptide sequence. These peptides can have any of the following sequences: SALTPSPSWLKYKAL (SEQ ID NO:9), ALTPSPSWLKYKAL (SEQ ID NO:10), TPSPSWLKYKAL (SEQ ID NO: 11), SPSWLKYKAL (SEQ ID NO:12), TPSPSWLKYK (SEQ ID NO: 13) and/or SWLKYKAL (SEQ ID NO:14).

In a particular embodiment, the DPEP-1 binding peptide has 3 amino acid residues removed from the N-terminus and/or C-terminus of the LSALT peptide sequence. In a particular embodiment, the peptide is LTPSPSWLKYKAL (SEQ ID NO:5).

Compositions are provided comprising an effective amount of a DPEP-1 binding peptide, wherein the DPEP-1 binding peptide comprises a neogenin-mimtec peptide or derivative thereof. In one embodiment the neogenin-mimetic peptide is SEQ ID NO:6. The neogenin-mimetic peptide is similar to a portion of the neogenin protein.

Neogenin is a multifunctional transmembrane receptor belonging to the immunoglobulin superfamily. Neogenin is able to transduce signals elicited by netrin. These neogenin-netrin interactions have been implicated in tissue morphogenesis, angiogenesis, myoblast differentiation and most recently in axon guidance. Neogenin is also a receptor for repulsive guidance molecule, a glycosylphosphatidylinositol-linked protein involved in neuronal differentiation, apoptosis and repulsive axon guidance. Numerous studies have been started to elucidate the in vivo functions of neogenin, and its role in multiple aspects of development and homeostasis. (Wilson & Key, International Journal of Biochemistry and Call Biology, Volume 39, Issue 5, 2007, Pages 874-878).

In a further embodiment, the peptide comprises a substituted neogenin-mimetic peptide (SEQ ID NO:6) wherein the neogenin-mimetic peptide is substituted with one or more D-amino or L-amino acids.

In one embodiment, neogenin-mimetic peptide comprises an amino acid sequence KHMHWHPPALNT (SEQ ID NO:6). In one embodiment, the neogenin-mimetic peptide contains an additional 1, 2, 3, 4, or 5 amino acid residues at the N-terminus and/or C-terminus of the peptide sequence. In another embodiment, the peptide has 1, 2, 3, 4, or 5 amino acid residues removed from the N-terminus and/or C-terminus of the neogenin-mimetic peptide sequence. In a further embodiment, the peptide comprises a substituted neogenin-mimetic peptide (SEQ ID NO:6) wherein the peptide is substituted with one or more D-amino or L-amino acids. In another embodiment, the peptide comprises one or more modifications selected from the group consisting of modified amino acids, amino acid analogs or combinations thereof.

In a particular embodiment, neogenin-mimetic peptide sequence consists essentially of an amino acid sequence KHMHWHPPALNT (SEQ ID NO:6). In one embodiment, the neogenin-mimetic peptide consists essentially of KHMHWHPPALNT and an additional 1, 2, 3, 4, or 5 amino acid residues at the N-terminus and/or C-terminus of the peptide sequence. In another embodiment, the peptide has 1, 2, 3, 4, or 5 amino acid residues removed from the N-terminus and/or C-terminus of the neogenin-mimetic peptide sequence. In a further embodiment, the neogenin-mimetic peptide consists essentially of a substituted neogenin-mimetic peptide (SEQ ID NO:6) wherein the neogenin-mimetic peptide is substituted with one or more D-amino or L-amino acids. In another embodiment, the peptide comprises one or more modifications selected from the group consisting of modified amino acids, amino acid analogs or combinations thereof.

In further aspect, compositions are provided comprising an effective amount of a DPEP-1 binding inhibiting peptide, wherein the DPEP-1 binding peptide contains a IPK peptide or derivative thereof.

In one embodiment, the IPK peptide sequence can be IPKXPXXXP (SEQ ID NO:7), where X is any naturally-occurring amino acid or where X is an unconventional amino acid or amino acid analog as described herein and known to those of skill in the art. In a specific embodiment, the IPK peptide sequence can be HIPKSPIQIPII (SEQ ID NO:8).

In other embodiments, the IPK peptide can contain an additional 1, 2, 3, 4, or 5 amino acid residues at the N-terminus and/or C-terminus of the peptide sequence. In another embodiment, the peptide has 1, 2, 3, 4, or 5 amino acid residues removed from the N-terminus and/or C-terminus of the IPK peptide sequence. In a further embodiment, the peptide comprises a substituted IPK peptide wherein the peptide is substituted with one or more D-amino or L-amino acids. In another embodiment, the peptide comprises one or more modifications selected from the group consisting of modified amino acids, amino acid analogs or combinations thereof.

To identify sequences that LSALT is bound to phage display biopanning against LSALT peptide was conducted as disclosed herein. Two peptides were identified containing the motif IPKXPXXXP. One of the IPK phage hits (HIPKSPIQIPII) was able to inhibit neutrophil adhesion in LPS-stimulated human endothelial cells (FIG. 20). The IPK motif may represent the binding site on DPEP-1 for the neutrophil ligand interaction. The IPK peptide may interfere with DPEP1-mediated leukocyte adhesion by binding to the neutrophil ligand that interacts with DPEP1, thus the IPK peptides disclosed herein are described as DPEP-1 binding inhibiting peptides. In one embodiment, the IPK peptides disclosed herein are non-competitive inhibitors to prevent binding to DPEP-1.

B. Modified Peptides and Peptide Analogs

In various embodiments, the peptide comprises amino acids, including carboxy- and/or amino-terminal amino acids in peptides, or can be modified by PEGylation, methylation, amidation, acetylation, prenylation and/or substitution with other chemical groups that can change the peptide's circulating half-life without adversely affecting its activity. Examples of unconventional or un-natural amino acids include, but are not limited to, citrulline, ornithine, norleucine, norvaline, 4-(E)-butenyl-4(R)-methyl-N-methylthreonine (MeBmt), N-methyl-leucine (MeLeu), aminoisobutyric acid, statine, and N-methyl-alanine (MeAla). Amino acids may participate in a disulfide bond. In certain embodiments, the amino acid has the general structure $H_2N$—C(H)(R)—COOH. In certain embodiments, the amino acid is a naturally-occurring amino acid. In certain embodiments, the amino acid is a synthetic or un-natural amino acid (e.g., α,α-disubstituted amino acids, N-alkyl amino acids); in some embodiments, the amino acid is a D-amino acid; in certain embodiments, the amino acid is an L-amino acid.

C. Rational Design and Structure-Function Analysis of DPEP-1 Binding Peptides

Different techniques give different and complementary information about protein structure. The primary structure is obtained by biochemical methods, either by direct determination of the amino acid sequence from the protein, or from the nucleotide sequence of the corresponding gene or cDNA. The quaternary structure of large proteins or aggregates can also be determined by electron microscopy. To obtain the secondary and tertiary structure, which requires detailed information about the arrangement of atoms within a protein, x-ray crystallography is commonly used. Other structural technologies to assess peptide structure and function include hydrogen-deuterium exchange mass spectrometry, bio-NMR, and cryo-EM.

The first prerequisite for solving the three-dimensional structure of a protein by x-ray crystallography is a well-ordered crystal that will diffract x-rays strongly. The crystallographic method directs a beam of x-rays onto a regular, repeating array of many identical molecules so that the x-rays are diffracted from it in a pattern from which the structure of an individual molecule can be retrieved. Well-ordered crystals of globular protein molecules are large, spherical, or ellipsoidal objects with irregular surfaces, and crystals thereof contain large holes or channels that are formed between the individual molecules. These channels, which usually occupy more than half the volume of the crystal, are filled with disordered solvent molecules. The protein molecules are in contact with each other at only a few small regions. This is one reason why structures of proteins determined by x-ray crystallography are generally the same as those for the proteins in solution X-ray crystallography can be used to screen compounds that are not known ligands of a target biomolecule for their ability to bind the target biomolecule. The method includes obtaining a crystal of a target biomolecule; exposing the target biomolecule crystal to one or more test samples; and obtaining an X-ray crystal diffraction pattern to determine whether a ligand/receptor complex is formed.

The DPEP-1 receptor is exposed to the test peptides by either co-crystallizing a biomolecule in the presence of one or more test samples or soaking the biomolecule crystal in a solution of one or more test samples. In another embodiment, structural information from ligand/receptor complexes are used to design ligands that bind tighter, that bind more specifically, that have better biological activity or that have better safety profile. These may include small molecules or other biotherapeutics such as antibodies.

Peptides described herein can be fully characterized using mass spectrometry, high performance liquid chromatography (HPLC) and amino acid analysis (AAA).

Mass spectrometry is used to obtain distance constraints between amino acid residues of a protein to be used in determining the structure the protein.

While not to be bound by any particular mechanism, it is believed that the peptide structure and any modifications that stabilize the tertiary structure enhance binding to DPEP-1.

In one embodiment, the DPEP-1 binding peptide forms an alpha-helix.

In various embodiments, the DPEP-1 binding peptide comprises a lactam bridge or glycine spacers. Such structures are employed to stabilize the peptide and improve the consistency of binding to DPEP-1.

In various embodiments, the DPEP-1 binding peptide comprises modifications to increase hydrophobicity on the outside of the DPEP-1 binding peptide. Such modifications are employed to increase binding to DPEP-1.

In one embodiment, the DPEP-1 binding peptide binds to the DPEP-1 receptor at an IPK motif on exon 3. An IPK motif is present in both human and mouse DPEP-1, but not DPEP-2 or DPEP-3 from human and mouse.

In one embodiment, a peptide interfering with ligand binding to the DPEP-1 IPK motif is HIPKSPIQIPII.

Unless defined otherwise, the scientific and technological terms and nomenclature used herein have the same meaning as commonly understood by a person of ordinary skill to which this invention pertains. Generally, the procedures of cell cultures, infection, molecular biology methods and the like are common methods used in the art. Such standard techniques can be found in reference manuals such as, for example, Ausubel et al., Current Protocols in Molecular Biology, Wiley Interscience, New York, 2001; and Sambrook et al., Molecular Cloning: A Laboratory Manual, 3rd edition, Cold Spring Harbor Laboratory Press, N.Y., 2001.

While peptides may be effective in eliciting a biological activity in vitro, their effectiveness in vivo might be reduced by the presence of proteases. Serum proteases have specific substrate requirements. The substrate must have both L-amino acids and peptide bonds for cleavage. Furthermore, exopeptidases, which represent the most prominent component of the protease activity in serum, usually act on the first peptide bond of the peptide and require a free N-terminus (Powell et al., Pharm. Res. 10:1268-1273 (1993)). In light of this, it is often advantageous to use modified versions of peptides. The modified peptides retain the structural characteristics of the original L-amino acid peptides that confer the desired biological activity of LSALT but are advantageously not readily susceptible to cleavage by protease and/or exopeptidases.

Systematic substitution of one or more amino acids of a consensus sequence with D-amino acid of the same type (e.g., D-lysine in place of L-lysine) may be used to generate more stable peptides. Thus, a peptide derivative or peptidomimetic disclosed herein may be all L, all D or mixed D, L peptide, in either forward or reverse order. The presence of an N-terminal or C-terminal D-amino acid increases the in vivo stability of a peptide since peptidases cannot utilize a D-amino acid as a substrate (Powell et al., Pharm. Res. 10:1268-1273 (1993)). Reverse-D peptides are peptides containing D-amino acids, arranged in a reverse sequence relative to a peptide containing L-amino acids. Thus, the C-terminal residue of an L-amino acid peptide becomes N-terminal for the D-amino acid peptide, and so forth. Retroinverso D-amino acid peptides retain the same secondary conformation and therefore similar activity, as the L-amino acid peptides, but are more resistant to enzymatic degradation in vitro and in vivo, and thus can have greater therapeutic efficacy than the original peptide (Brady and Dodson, Nature 368:692-693 (1994); Jameson et al., Nature 368:744-746 (1994)). Similarly, a reverse-L peptide may be generated using standard methods where the C-terminus of the parent peptide becomes takes the place of the N-terminus of the reverse-L peptide. It is contemplated that reverse L-peptides of L-amino acid peptides that do not have significant secondary structure (e.g., short peptides) retain the same spacing and conformation of the side chains of the L-amino acid peptide and therefore often have the similar activity as the original L-amino acid peptide. Moreover, a reverse peptide may contain a combination of L- and D-amino acids. The spacing between amino acids and the conformation of the side chains may be retained resulting in similar activity as the original L-amino acid peptide.

In one embodiment, the peptide is chemically modified to confer resistance to peptidases acting on the N-terminal or C-terminal residues of a peptide by adding chemical groups at the peptide termini, such that the modified peptide is no longer a substrate for the peptidase. In one embodiment, one such chemical modification is glycosylation of the peptides at either or both termini. In other embodiments, chemical modifications which enhance serum stability include, but are not limited to, the addition of an N-terminal alkyl group, consisting of a lower alkyl of from one to twenty carbons, such as an acetyl group, and/or the addition of a C-terminal amide or substituted amide group. In particular, the compositions disclosed herein include modified peptides consisting of peptides bearing an N-terminal acetyl group and/or a C-terminal amide group.

In one embodiment, substitution of certain naturally-occurring amino acids for non-naturally amino acids in the peptides confers resistance to proteolysis. Such a substitution can, for instance, confer resistance to proteolysis by exopeptidases acting on the N-terminus without affecting biological activity. Examples of non-naturally-occurring amino acids include α,α-disubstituted amino acids, N-alkyl amino acids, C-α-methyl amino acids, β-amino acids, and β-methyl amino acids. Amino acids analogs useful in the present invention may include, but are not limited to, β-alanine, norvaline, norleucine, 4-aminobutyric acid, orithine, hydroxyproline, sarcosine, citrulline, cysteic acid, cyclohexylalanine, 2-aminoisobutyric acid, 6-aminohexanoic acid, t-butylglycine, phenylglycine, o-phosphoserine, N-acetyl serine, N-formylmethionine, 3-methylhistidine and other unconventional amino acids. Furthermore, the synthesis of peptides with non-naturally-occurring amino acids is known in the art.

Peptide analogs are commonly used in the pharmaceutical industry as non-peptide drugs with properties analogous to those of the template peptide. The non-peptide compounds are termed "peptide mimetics" or peptidomimetics (Fauchere et al., Infect. Immun. 54:283-287 (1986); Evans et al., J. Med. Chem. 30:1229-1239 (1987)). Peptide mimetics that are structurally related to therapeutically useful peptides and may be used to produce an equivalent or enhanced therapeutic or prophylactic effect. Generally, peptidomimetics are structurally similar to the paradigm polypeptide (i.e., a polypeptide that has a biological or pharmacological activity) such as naturally-occurring receptor-binding polypeptides, but have one or more peptide linkages optionally replaced by linkages such as —$CH_2NH$—, —$CH_2S$—, —$CH_2$—, —CH=CH—(cis and trans), —$CH_2SO$—, —CH(OH)$CH_2$—, —COCH$_2$- etc., by methods well known in the art (Spatola, Peptide Backbone Modifications, Vega Data, 1(3):267 (1983); Spatola et al. Life Sci. 38:1243-1249 (1986); Hudson et al. Int. J. Pept. Res. 14:177-185 (1979); and Weinstein. B., 1983, Chemistry and Biochemistry, of Amino Acids, Peptides and Proteins, Weinstein eds, Marcel Dekker, New-York,). Such peptide mimetics may have significant advantages over naturally-occurring polypeptides including more economical production, greater chemical stability, enhanced pharmacological properties (e.g., half-life, absorption, potency, efficiency, etc.), reduced antigenicity and others.

Pharmaceutically acceptable salts retain the desired biological activity of the parent peptide without toxic side effects.

In one embodiment, proteomic and other structural biology methods determine the critical amino acid residues on LSALT peptide or DPEP1 can be used to design novel peptide sequences, peptidomimetics or small molecules that display similar inhibitory and binding properties to DPEP1.

In one embodiment, determining key DPEP1 epitopes that bind LSALT peptide can also be used to develop therapeutic antibodies targeting DPEP1, leukocyte adhesion and cancer metastasis. Examples of such methods include but are not limited to crystallizing DPEP1 bound to LSALT and analysis by X-ray diffraction. In another embodiment, photochemical crosslinking of LSALT bound to DPEP1 followed by protease digestion and mass spectrometry (Ngai et al, J Biol Chem 1994) is used to identify the key LSALT amino acids and DPEP1 domains involved in the interaction. In another embodiment, recombinant DPEP-1 protein is injected into a mammal to immunize the host and generate a library of DPEP1-specific antibodies. In various embodiments, in silico modeling is performed to develop novel pharmaceutical compositions.

IV. Pharmaceutical Formulations and Medicaments

In another aspect, the compounds or agents described herein, as well as variants and modifications thereof, are provided as a pharmaceutical composition for therapeutic use. In one embodiment, the pharmaceutical formulation comprises an isolated peptide includes a sequence listed in Table 1. In another embodiment, the pharmaceutical formulation comprises an isolated peptide contained as an insert in a phage virus, and/or may further comprise 1, 2, 3, 4, 5 additional amino acid residues at the N-terminus and/or C-terminus of the peptide sequence.

Representative delivery regimens include oral, parenteral (including subcutaneous, intramuscular and intravenous injection), rectal, buccal (including sublingual), transdermal, inhalation ocular and intranasal. In one embodiment, delivery of compounds entails subcutaneous injection of a controlled-release injectable formulation. In some embodiments, compounds described herein are useful for subcutaneous, intranasal and inhalation administration.

The selection of the exact dose and composition and the most appropriate delivery regimen will be influenced by, inter alia, the pharmacological properties of the selected peptide, the nature and severity of the condition being treated, and the physical condition and mental acuity of the recipient. Additionally, the route of administration will result in differential amounts of absorbed material. Bioavailabilities for administration of compounds through different routes are particularly variable, with amounts from less than 1% to near 100% being seen. Typically, bioavailability from routes other than intravenous, intraperitoneal or subcutaneous injection are 50% or less.

The pharmaceutical compositions or formulations of the present invention can be formulated with a physiologically acceptable carrier or excipient to prepare a pharmaceutical composition. The carrier and composition can be sterile. The formulation should suit the mode of administration, for example intravenous or subcutaneous administration. Methods of formulating compositions are known in the art (see, e.g., Remington's Pharmaceuticals Sciences, 17th Edition, Mack Publishing Co., (Alfonso R. Gennaro, editor) (1989)).

Suitable pharmaceutically acceptable carriers include, but are not limited to, water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, or others, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents (e.g., lubricants, preservatives, stabilizers, wetting agents, emulsifiers, salts for influencing osmotic pressure, buffers, coloring and/or aromatic substances and the like) which do not deleteriously react with the active compounds or interference with their activity. In a preferred embodiment, a water-soluble carrier suitable for intravenous administration is used.

The composition or medicament, if desired, can also contain minor amounts of wetting or emulsifying agents, or pH buffering agents. The composition can be a liquid solution, suspension, emulsion, sustained release formulation, or powder. The composition can also be formulated as a suppository, with traditional binders and carriers such as triglycerides.

The composition or medicament can be formulated in accordance with the routine procedures as a pharmaceutical composition adapted for administration to human beings. For example, in a preferred embodiment, a composition for intravenous administration typically is a solution in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

In some embodiments, the pharmaceutical composition comprise a liquid carrier such as, but not limited to, water, saline, phosphate buffered saline, Ringer's solution, dextrose solution, serum-containing solutions, Hank's solution, other aqueous physiologically balanced solutions, oils, esters and glycols.

The compounds as described herein can be formulated as neutral or salt forms. As stated above, pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The pharmaceutical formulations of the present invention contain, as the peptide may be mixed with an excipient, diluted by an excipient or enclosed within a carrier, which can be in the form of a capsule, sachet, paper or other container, according to well-known methods and pharmaceutical compositions. The composition may be administered by any route suitable for peptide administration, including parenteral, intravenous, subcutaneous, or intramuscular administration. Typically, the peptide is dissolved or suspended in a sterile injectable solution, at a concentration sufficient to provide the required dose in 0.5 to 2 ml or less. Pharmaceutical compositions of this invention suitable for parenteral administrations comprise one or more compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, solutes which render the formulation isotonic with the blood of the intended recipient or suspending or thickening agents.

Injectable depot forms are made by forming microencapsulated matrices of the drug in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues. The injectable materials can be sterilized for example, by filtration through a bacterial-retaining filter.

The pharmaceutical compositions may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

V. Methods of Treatment

Methods of treatment are contemplated for diseases and conditions associated with inflammation including particularly diseases and conditions where inflammation is caused by ischemia/reperfusion injury to a tissue or organ. Ischemia followed by reperfusion in an organ produces structural and functional abnormalities in the tissue of that organ and others. Neutrophil infiltration, hemorrhage, edema and necrosis are all observed in tissues following an ischemia/reperfusion injury. The DPEP-1 target represents a previously undescribed pathway for inflammation which opens up the opportunity for dipeptidase inhibitors such as those described herein to be used to treat or prevent diseases and conditions mediated by inflammation.

A non-limiting list of common diseases and medical problems that are directly associated with inflammation include: arthritis, kidney failure, lupus, asthma, psoriasis, pancreatitis, allergy, fibrosis, surgical complications, anemia, and fibromyalgia. Other diseases associated with chronic inflammation include cancer, which is caused by chronic inflammation; heart attack where chronic inflammation contributes to coronary atherosclerosis; Alzheimer disease where chronic inflammation destroys brain cells; congestive heart failure where chronic inflammation causes heart muscle wasting; stroke where chronic inflammation promotes thrombo-embolic events; and aortic valve stenosis where chronic inflammation damages heart valves. Arteriosclerosis, osteoporosis, Parkinson's disease, infection (sepsis), inflammatory bowel disease including Crohn's disease and ulcerative colitis as well as multiple sclerosis.

In particular embodiments, the methods described herein are useful for protecting tissues and organs from damage associated with conditions such as, but not limited to sepsis-induced injury, acute organ injury (for example acute kidney injury in the setting of low blood pressure).

In other embodiments, the methods described herein are useful for protecting tissues and organs from damage associated with sepsis-induced conditions such as acute respiratory distress syndrome, encephalopathy, sepsis-induced liver failure, sepsis-induced kidney failure or sepsis-induced heart failure.

In other embodiments, the methods described herein are useful for protecting tissues and organs from damage associated with ischemia-reperfusion injury such as, but not limited to peri-operative procedures, heart failure, liver failure, stroke, myocardial infarct, shock liver, spinal cord injury, brain injury, and the like. These compositions can also be used to prevent or treat ischemia-reperfusion injury in high risk patients.

In other embodiments, the methods are also useful prior to angioplasty or thrombolytic therapy, or after transplantation or reperfusion of an ischemic organ following surgery, angioplasty or thrombolytic therapy.

Other examples of surgical procedures and organs at risk of ischemia reperfusion injury during these procedures include, but are not limited, brain injury during carotid artery surgery, cerebral vascular surgery and surgery of the heart and aorta; brain, spinal cord, intestine and kidney injury; lung injury following thromboembolectomy or the use of cardiopulmonary bypass during lung and heart surgery; heart injury following revascularization (coronary artery bypass graft surgery); intestinal injury following surgery on the mesenteric arteries; and skin injury following harvesting of a skin graft.

Additional surgical procedures for which this method is useful include harvesting donor organs for transplantation. In other embodiments, the methods are also useful for the protection of allograft organs during donor procurement, ex vivo handling and implantation into a transplant recipient. Compositions of the present invention can be administered prior to, during or following harvesting a donor organ which will be transplanted, prior to or during a surgical procedure in which ischemia is expected.

Hence, the invention relates to a method for preventing, limiting, or treating ischemia reperfusion injury in a subject, comprising the steps of identifying a subject that has undergone an ischemic event, or in which an ischemic event is imminent or is at risk for having an ischemic event and administering a therapeutically effective or prophylactically effective amount of the compositions described herein.

In one embodiment, a method is disclosed for extracting an organ from a donor, comprising administering a composition that binds to DPEP-1 disclosed herein to the donor prior to extraction of the organ. Optionally, a method is disclosed for the recipient of a transplant organ, comprising administering a composition that binds to DPEP1 prior to organ implantation. The method may further comprise monitoring the level of one or more inflammatory makers to determine whether the one or more markers is below a designated level prior to extraction, i.e., to determine whether the organ meets a predetermined marker profile.

In a particular embodiment, the organ is selected from the group consisting of consisting of heart, liver, kidney, brain, intestine (large or small), pancreas, lung, stomach, bladder, spleen, ovaries, testes, skeletal muscle and combinations thereof.

In a particular embodiment, the donor is a marginal donor. In one embodiment, the marginal donor is selected from the group consisting of complex living donors, a non-heart beating donor (NHBD) or a deceased cardiac donor.

In a particular embodiment, the complex living donor is of advanced age, e.g., greater than about 60 years old, greater than about 65 years old or greater than about 70 years old.

In another particular embodiment, the complex living donor has one or more risk factors selected from the group consisting of obesity, hypertension, diabetes, nephrolithiasis (kidney stones), transmissible infectious disease (e.g., a viral infection), or combinations thereof.

In one embodiment, the method further comprises storing the organ. Optionally, the level of one or more inflammatory markers may be measured one or more time during storage of the organ.

In another embodiment, the method further comprising (iv) providing the organ to a recipient, e.g., by transplantation. Optionally, the level of one or more inflammatory markers may be measured after the organ is provided, e.g., during the immediate postreperfusion period.

In a particular embodiment, the one or more inflammatory markers are selected from the group consisting of IL-12, IP-10, IL-1β, IL-5, GM-CSF, IFNγ or IL-1α.

Optionally, one or more additional agents (e.g., antioxidant) may be administered to the donor prior to extraction of the organ. One or more additional agents (e.g., antioxidant) may be administered to the recipient prior to implantation of the organ. The one or more additional agents may be administered prior to, contemporaneously therewith or after administration of a composition that binds to DPEP-1. The agent may be, for example, a small molecule, biologic agent or therapeutic gas.

In certain embodiments, the method disclosed herein may result in one of more beneficial effects including, without limitation, improved graft function, reduced graft dysfunction, improve graft survival (including long term survival), reduced graft deterioration, reduced incidence of delayed graft function (DGF) or the like In one embodiment, the method results in an increase in graft survival compared to survival of grafts to which a composition that binds to DPEP-1 is not administered prior to extraction or implantation. Graft survival may be measured, e.g., at six months, one year or three years following transplantation. In a particular embodiment, graft survival is increased by about 5%, about 10%, about 15%, about 20% or about 25% or more.

In one embodiment, a method of preserving an organ is disclosed, comprising exposing a stored organ (i.e., an extracted organ awaiting transplantation) to a composition that binds to DPEP-1 disclosed herein. Optionally, the method further comprising monitoring the level of inflammatory markers one or more times to determine whether they fall below a designated level. In certain embodiments, the organ is stored in an organ transplant solution. In certain embodiments, the organ is stored at temperatures a temperature between about 0° C. and 4° C. In another embodiment, the organ is stored at a temperature of about 37 ° C., i.e., under non-thermic conditions. In certain embodiment, the stored organ is connected to or associated with an organ perfusion system.

In a particular embodiment, the method of preserving the organ disclosed herein permits an increase in the maximum cold ischemia time for the particular organ without impairment, e.g., without an increase in delayed graft function (DGF). In certain embodiments, the increase in between about 5 and about 50%, more particularly, between about 5 and about 25%, or about 5%, about 10%, about 15%, about 20%, about 25% or about 30% or more.

In another embodiment, a method of preventing ischemia-reperfusion related injury in an organ transplant patient is provided, comprising administering a composition that binds to DPEP-1 disclosed herein prior to, simultaneously with or after providing the organ to the patient.

In another embodiment, an organ harvesting kit is disclosed comprising the a composition that binds to DPEP-1 disclosed herein. Optionally, the organ harvesting kit may contain or more additional agents.

While not to be bound by any particular mechanism, the protective effects of the compositions provided herein are mediated through binding at the DPEP-1 target and a direct reduction in DPEP-1-regulated leukocyte recruitment, inflammation and tumor cell adhesion. These effects described herein on inflammation-mediated disease and tumor metastasis occur independent of DPEP-1 dipeptidase activity or its role in regulating tubular transport. Previous studies have required combination of a DPEP-1 antagonists to prolong the half-life of an antibiotic compound to treat bacterial infection. Other studies have used a DPEP-1 antagonist cilastatin to prevent or treat organ damage by preventing the renal tubular uptake of chemotherapeutic agents, or other nephrotoxic agents (Humanes et al., Kidney Intl, 82:652-553 (2012); Koller et al., Biochem Biophys Res Comm 131(2):974-979 (1985)). The direct treatment of DPEP-1 regulated inflammation, inflammation-mediated disease or tumor metastasis by using DPEP-1 antagonists has not previously been identified.

As such, in certain embodiments, the compositions described herein are not used to treat or reduce tissue damage induced directly by toxic compounds such as nephrotoxic compounds or chemotherapeutic agents. In other embodiments, the compositions described herein are not administered in combination with beta-lactam antibiotic compounds. In other embodiments, the compositions described herein are not administered in combination with carbapenem antibiotic compounds.

The invention provides a method to reduce or modulate inflammation comprising administering an effective amount of a composition that binds to DPEP-1 to reduce or modulate inflammation.

In one embodiment, inflammation is characterized by a profile of inflammatory markers selected from IL-12, IP-10, IL-1β, IL-5, GM-CSF, IFNγ, or IL-1α.

In one embodiment, the composition comprises a peptide, peptidomimetic blocking antibody or a small molecule compound.

In one embodiment, the inflammation is associated with an inflammatory disorder is selected from the group consisting of gastritis, gout, gouty arthritis, arthritis, rheumatoid arthritis, inflammatory bowel disease, Crohn's disease, ulcerative colitis, ulcers, chronic bronchitis, asthma, allergy, acute lung injury, pulmonary inflammation, airway hyperresponsiveness, vasculitis, septic shock, inflammatory skin disorders, psoriasis, atopic dermatitis, and eczema.

The invention provides a method to block leukocyte recruitment of a subject comprising administering an effective amount of a composition that binds to DPEP-1 to block leukocyte recruitment.

In one embodiment, the method further comprises identifying a subject in need of treatment by diagnostic test for needing reduction in inflammation. Indications for treatment include, but are not limited to, clinical signs and symptoms in any patient that is at risk for acute kidney injury (preoperatively or before administering intravenous contrast) or in any patient having decreasing urine output or increasing serum creatinine, such as in a patient with a systemic infection or low blood pressure.

The invention provides a method for reducing or preventing tumor metastasis in a subject comprising administering an effective amount of a composition that binds to DPEP-1 thereby reducing or preventing tumor metastasis. In one embodiment, DPEP-1 can acts as an adhesion molecule for leukocytes on tumor cells independent of its enzymatic activity and binding DPEP-1 by a selective DPEP-1 binding agent described herein may reduce or prevent tumor metastasis. In another embodiment, DPEP-1 contributes to inflammation which promotes tumor metastasis and binding of DPEP-1 by selective DPEP-1 binding agents reduces or prevents tumor metastasis.

In certain embodiments, the tumor is selected from those tumors known to cause cancer that have the potential to, or are presently capable, of metastasis. For example, the cancer can be pancreatic cancer, kidney cancer, e.g., renal cell carcinoma (RCC), urogenital cancer, e.g., urothelial carcinomas in urinary bladder, kidney, pelvic and ureter, melanoma, prostate carcinoma, lung carcinomas (non-small cell carcinoma, small cell carcinoma, neuroendocrine carcinoma and carcinoid tumor), breast carcinomas (ductal carcinoma, lobular carcinoma and mixed ductal and lobular carcinoma), thyroid carcinomas (papillary thyroid carcinoma, follicular carcinoma and medullary carcinoma), brain cancers (meningioma, astrocytoma, glioblastoma, cerebellum tumors, medulloblastoma), ovarian carcinomas (serous, mucinous and endometrioid types), cervical cancers (squamous cell carcinoma in situ, invasive squamous cell carcinoma and endocervical adenocarcinoma), uterine endometrial carcinoma (endometrioid, serous and mucinous types), primary peritoneal carcinoma, mesothelioma (pleura and peritoneum), eye cancer (retinoblastoma), muscle (rhabdosarcoma and leiomyosarcoma), lymphomas, esophageal cancer (adenocarcinoma and squamous cell carcinoma), gastric cancers (gastric adenocarcinoma and gastrointestinal stroma tumor), liver cancers (hepatocellular carcinoma and bile duct cancer), small intestinal tumors (small intestinal stromal tumor and carcinoid tumor) colon cancer (adenocarcinoma of the colon, colon high grade dysplasia and colon carcinoid tumor), testicular cancer, skin cancers (melanoma and squamous cell carcinoma) and adrenal carcinoma.

In one embodiment, the method further comprises identifying a subject in need of treatment through diagnostic tests to determine a need for reduction or prevention of tumor metastasis by determining the presence of a DPEP-1-binding molecule on a tumor of a patient.

The invention provides a method for reducing or preventing leukocyte recruitment and inflammation during sepsis in a subject comprising administering an effective amount of a composition that binds to DPEP-1 thereby reducing or preventing the organ complications of sepsis.

In one embodiment, the method further comprises identifying a subject in need of treatment through diagnostic test to determine a need for reduction or prevention of ischemia-reperfusion injury. Indications for treatment include, but are not limited to, clinical signs and symptoms of ischemia-reperfusion injury or undergoing a surgical procedure with a high risk of ischemia-reperfusion injury.

The invention includes a method of treating a symptom of ischemia-reperfusion injury in a patient comprising administering to the patient a pharmaceutically effective amount of a composition that binds to and inhibits DPEP-1.

In one embodiment, the composition is administered until symptoms of ischemia-reperfusion injury are reduced or ameliorated.

In one embodiment, the isolated peptide or variant thereof is administered at a dosage is between about 0.01 mg/kg to 100 mg/kg.

The invention provides a method for reducing or preventing ischemia-reperfusion injury related disorders in a subject comprising administering an effective amount of a composition that binds to DPEP-1 thereby reducing or preventing ischemia-reperfusion injury. In one embodiment, the method reduces or prevents the leukocyte recruitment and inflammation that is associated with ischemia-reperfusion injury.

In one embodiment, the ischemia-reperfusion injury related disorder is associated with ischemic and post-ischemic events in organs and tissues, and the disorder is selected from a group consisting of thrombotic stroke; myocardial infarction; angina pectoris; embolic vascular occlusions; peripheral vascular insufficiency; splanchnic artery occlusion; arterial occlusion by thrombi or embolisms, arterial occlusion by non-occlusive processes such as following low mesenteric flow or sepsis; mesenteric arterial occlusion; mesenteric vein occlusion; ischemia-reperfusion injury to the mesenteric microcirculation; ischemic acute renal failure; ischemia-reperfusion injury to the cerebral tissue; intestinal intussusception; hemodynamic shock; tissue dysfunction; organ failure (including heart failure, liver failure, kidney failure and the like); restenosis; atherosclerosis; thrombosis; platelet aggregation; shock liver; spinal cord injury; brain injury or following conditions selected from a list comprising of procedures such as peri-operative procedures, cardiac surgery; organ surgery; organ transplantation; angiography; cardiopulmonary and cerebral resuscitation.

In one embodiment, the ischemia-reperfusion injury is associated with harvesting donor organs for transplantation.

In one embodiment, the ischemia-reperfusion injury occurs to allograft organs during donor procurement, ex vivo handling or implantation into a transplant recipient.

In various embodiments, the compositions can be administered (i) prior to, during or following harvesting a donor organ which will be transplanted or (ii) prior to or during a surgical procedure in which ischemia is expected.

The invention provides a method for reducing or preventing acute kidney injury in a subject comprising administering an effective amount of a composition that binds to DPEP-1 thereby reducing or preventing acute kidney injury. In one embodiment, the method reduces or prevents the leukocyte recruitment and inflammation that is associated with acute kidney injury.

In one embodiment, the method comprises identifying a subject in need of treatment through diagnostic test to determine a need for reduction or prevention of acute kidney injury.

In one embodiment, the acute kidney injury is a result of sepsis.

In one embodiment, the acute kidney injury is a result of ischemia reperfusion.

In one embodiment, the acute kidney injury is toxin-induced kidney injury.

In one embodiment, the acute kidney injury is contrast-induced kidney injury.

In certain embodiments, the composition may be administered in combination with one or more additional therapeutic agents. Co-administration includes simultaneous administration in separate compositions (also referred to as concurrent administration), administration at different times in separate compositions, or administration in a composition in which both agents are present. Simultaneous administration in separate compositions and administration in a composition in which both agents are present are preferred.

In one embodiment, the at least one additional therapeutic agent is selected from the group consisting of chemotherapeutic or anti-proliferative agents, antiviral, antibiotic, antihistamine, an emollient, systemic phototherapy, psoralen photochemotherapy, laser therapy, hormone replacement therapy, an anti-inflammatory agent, an immunomodulatory or immunosuppressive agent, a neurotrophic factor, an agent for treating cardiovascular disease, an agent for treating diabetes, an agent for treating immunodeficiency disorders, and immune checkpoint inhibitors.

VI. Routes of Administration

A composition that binds to DPEP-1 as described herein may be administered by any appropriate route. In some embodiments, the DPEP-1 binding peptide is administered parenterally. In some embodiments, the parenteral administration is selected from intravenous, intradermal, inhalation, transdermal (topical), intraocular, intramuscular, subcutaneous, intramuscular, and/or transmucosal administration. In some embodiments, an DPEP-1 binding peptide as described herein is administered subcutaneously. As used herein, the term "subcutaneous tissue", is defined as a layer of loose, irregular connective tissue immediately beneath the skin. For example, the subcutaneous administration may be performed by injecting a composition into areas including, but not limited to, thigh region, abdominal region, gluteal region, or scapular region. In some embodiments, a composition that binds to DPEP-1 as described herein is administered intravenously. In other embodiments, a composition that binds to DPEP-1 as described herein is administered by direct administration to a target tissue, such as heart or muscle (e.g., intramuscular), tumor (intratumorally), nervous system (e.g., direct injection into the brain; intraventricularly; intrathecally). Alternatively, a composition that binds to DPEP-1 as described herein (or a composition or medicament containing a DPEP-1 binding peptide as described herein) can be administered by inhalation, parenterally, intradermally, transdermally, or transmucosally (e.g., orally or nasally). More than one route can be used concurrently, if desired.

In some embodiments, a composition that binds to DPEP-1 as described herein is administered orally. In some embodiments, the present invention provides solid dosage forms of DPEP-1 binding peptides as described herein for oral administration including (a) a DPEP-1 binding peptide, (b) at least one pharmaceutically acceptable pH-lowering agent, (c) at least one absorption enhancer effective to promote bioavailability of the DPEP-1 binding peptide, and (d) a protective vehicle. In some embodiments, the solid dosage form is a capsule or tablet.

VII. Dosing

An effective quantity of a composition that binds to DPEP-1 of interest is employed in treatment. The dosage of peptides used in accordance with the invention varies depending on the peptide and the condition being treated. For example, the age, weight, and clinical condition of the recipient patient; and the experience and judgment of the clinician or practitioner administering the therapy are among the factors affecting the selected dosage. Other factors include: the route of administration, the patient, the patient's medical history, the severity of the disease process, and the potency of the particular peptide. The dose should be sufficient to ameliorate symptoms or signs of the disease treated without producing unacceptable toxicity to the patient. In general, an effective amount of the peptide is that which provides either subjective relief of symptoms or an objectively identifiable improvement as noted by the clinician or other qualified observer.

Various embodiments may include differing dosing regimen. In some embodiments, the DPEP-1 binding composition is administered via continuous infusion. In some embodiments, the continuous infusion is intravenous. In other embodiments, the continuous infusion is subcutaneous. Alternatively or additionally, in some embodiments, the composition that binds to DPEP-1 is administered bimonthly, monthly, twice monthly, triweekly, biweekly, weekly, twice weekly, thrice weekly, daily, twice daily, or on another clinically desirable dosing schedule. The dosing regimen for a single subject need not be at a fixed interval, but can be varied over time, depending on the needs of the subject.

In one embodiment, the local dosage is administered at least once a day until a therapeutic result is achieved. The dosage can be administered twice a day, but more or less frequent dosing can be recommended by the clinician. Once a therapeutic result is achieved, the peptide can be tapered or discontinued. Occasionally, side effects warrant discontinuation of therapy. An effective quantity of the peptide of interest is employed in treatment. The dosage of peptides used in accordance with the invention varies depending on the compound and the condition being treated. The age, lean body weight, total weight, body surface area, and clinical condition of the recipient patient; and the experience and judgment of the clinician or practitioner administering the therapy are among the factors affecting the selected dosage. Other factors include the route of administration the patient, the patient's medical history, the severity of the disease process, and the potency of the particular compound. The dose should be sufficient to ameliorate symptoms or signs of the disease treated without producing unacceptable toxicity to the patient.

When employed as pharmaceuticals, the peptides of the present invention are administered in the form of pharmaceutical compositions and these pharmaceutical compositions represent further embodiments of the present invention. These peptides can be administered by a variety of routes including oral, rectal, transdermal, subcutaneous, intravenous, intramuscular, and intranasal, or via intratracheal instillation or aerosol inhalation.

The compositions that bind to DPEP-1 are useful in reducing inflammation or modifying the inflammatory profile of a tissue, e.g., into the liver. The manner of administration will be defined by the application of the compound and can be determined by routine methods of clinical testing to find the optimum dose.

In one embodiment, the dosage is between about 0.01 mg/kg to about 100 mg/kg of active peptide, between about 0.01 mg/kg to about 50 mg/kg, or between about 0.01 mg/kg to about 25 mg/kg.

In other embodiments, the dosage is between about 0.1 mg/kg to about 100 mg/kg, between about 0.1 mg/kg to about 50 mg/kg, between about 0.1 mg/kg to about 25 mg/kg, or between about 0.1 mg/kg to about 10 mg/kg.

In other embodiments, the dosage is between about 0.5 mg/kg to about 100 mg/kg, about 0.5 mg/kg to about 50 mg/kg, about 0.5 mg/kg to about 25 mg/kg, or about 0.5 mg/kg to about 10.0 mg/kg.

In other embodiments, the dosage is between about 1.0 mg/kg to about 25 mg/kg, between about 1.0 mg/kg to about 50 mg/kg, between about 1.0 mg/kg to about 70 mg/kg, between about 1.0 mg/kg to about 100 mg/kg, between about 5.0 mg/kg to about 25 mg/kg, between about 5.0 mg/kg to about 50 mg/kg, between about 5.0 mg/kg to about 70 mg/kg, between about 5.0 mg/kg to about 100 mg/kg, between about 10.0 mg/kg to about 25 mg/kg, between about 10.0 mg/kg to about 50 mg/kg, between about 10.0 mg/kg to about 70 mg/kg, or between about 10.0 mg/kg to about 100 mg/kg.

In another embodiment, the dosage is between about 50 μM and about 500 μM.

It will be understood, however, that the amount of the DPEP-1 binding composition actually administered will be determined by a physician, in the light of the relevant circumstances, including the condition to be treated, the chosen route of administration, the actual compound administered, the age, weight, and response of the individual patient, the severity of the patient's symptoms, and the like.

In various embodiments, compositions described herein, or salts thereof, are administered in amounts between about 0.001 and about 20 mg/kg body weight per day, between about 0.01 and about 10 mg/kg body weight per day, between about 0.1 and about 1000 µg/kg body weight per day, or between about 0.1 to about 100 µg/kg body weight per day. Routes of administration vary. For example, peptides described herein, or salts thereof, are administered in amounts between about 0.1 and about 1000 µg/kg body weight per day, or between about 0.1 to about 100 µg/kg body weight per day, by subcutaneous injection. By way of example, for a 50 kg human female subject, the daily dose of active ingredient is from about 5 to about 5000 µg, or from about 5 to about 5000 µg by subcutaneous injection. Different doses will be needed, depending on the route of administration, the peptide potency, the pharmacokinetic profile and the applicable bioavailability observed, and the active agent and the disease being treated. In an alternate embodiment where the administration is by inhalation, the daily dose is from 1000 to about 20,000 µg, twice daily. In other mammals, such as horses, dogs, and cattle, higher doses may be required. This dosage may be delivered in a conventional pharmaceutical composition by a single administration, by multiple applications, or via controlled release, as needed to achieve the most effective results.

VIII. Kits

In some embodiments, the present invention further provides kits or other articles of manufacture which contain a DPEP-1 binding peptide or pharmaceutical compositions described herein, as well as instructions for its reconstitution (if lyophilized) and/or use. Kits or other articles of manufacture may include a container, a syringe, vial and any other articles, devices or equipment useful in administration (e.g., subcutaneous, by inhalation). Suitable containers include, for example, bottles, vials, syringes (e.g., pre-filled syringes), ampules, cartridges, reservoirs, or lyo-jects. The container may be formed from a variety of materials such as glass or plastic. In some embodiments, the container is a pre-filled syringe. Suitable pre-filled syringes include, but are not limited to, borosilicate glass syringes with baked silicone coating, borosilicate glass syringes with sprayed silicone, or plastic resin syringes without silicone.

Typically, the container may hold formulations and a label on, or associated with, the container that may indicate directions for reconstitution and/or use. For example, the label may indicate that the formulation is reconstituted to concentrations as described above. The label may further indicate that the formulation is useful or intended for, for example, subcutaneous administration. In some embodiments, the container may contain a single dose of a stable formulation containing a DPEP-1 binding peptide. In various embodiments, a single dose of the stable formulation is present in a volume of less than about 15 ml, about 10 ml, about 5.0 ml, about 4.0 ml, about 3.5 ml, about 3.0 ml, about 2.5 ml, about 2.0 ml, about 1.5 ml, about 1.0 ml, or about 0.5 ml. Alternatively, the container holding the formulation may be a multi-use vial, which allows for repeat administrations (e.g., from 2-6 administrations) of the formulation. Kits or other articles of manufacture may further include a second container comprising a suitable diluent (e.g., BWFI, saline, buffered saline). Upon mixing of the diluent and the formulation, the final protein concentration in the reconstituted formulation will generally be at least about 1 mg/ml (e.g., at least about 5 mg/ml, at least about 10 mg/ml, at least about 20 mg/ml, at least about 30 mg/ml, at least about 40 mg/ml, at least about 50 mg/ml, at least about 75 mg/ml, at least about 100 mg/ml). Kits or other articles of manufacture may further include other materials desirable from a commercial and user standpoint, including other buffers, diluents, filters, needles, syringes, and package inserts with instructions for use. In some embodiments, kits or other articles of manufacture may include an instruction for self-administration.

IX. Screening Methods

Disclosed herein is a method for screening for compositions (e.g., peptides) that bind to DPEP-1.

In one embodiment, the method comprises: a) screening a library of test peptides for their ability to bind to DPEP-1 in the tissue; and (b) identifying peptides that show selective binding affinity. In certain embodiments, the identified peptides are subject to one or more additional testing methods.

In one embodiment, the screening method comprises identifying a peptide effective to decrease inflammation in a tissue of a patient comprising: (a) screening a library of test peptides for their ability to bind to DPEP-1 in the tissue; (b) selecting candidate test peptides that show selective binding affinity; (c) testing the candidate peptides for inflammation reducing activity, and (d) selecting a candidate peptide if it decrease inflammation, thereby providing a peptide effective to decrease inflammation.

For those library compounds that show a selective binding affinity to one of the target peptides in the library, e.g., at least a 10-100 fold increase in binding affinity over a random-sequence peptide, the compound is further testing for its ability to reduce inflammation in a tissue, according to methods detailed below. Test compounds that are shown to reduce inflammation in a tissue are then identified as lead compounds for further compound testing and development.

In one embodiment, the tissue is lung tissue or liver tissue.

In one embodiment, a method is provided for identifying a peptide effective to block leukocyte recruitment in the vasculature of a patient.

In one embodiment, the invention provides a method of identifying a peptide effective to reduce inflammation in a tissue of a patient comprising: (a) screening a library of test peptides for their ability to bind to DPEP-1; (b) selecting peptides that show selective binding affinity; (c) testing the peptides for leukocyte recruitment inhibiting activity, and (d) selecting a peptide if it reduces inflammation in a tissue.

In one embodiment, the tissue is lung tissue or liver tissue.

In one embodiment, the method further comprises the steps of (e) further testing the peptide for its ability to block leukocyte recruitment in an animal bearing a solid tumor; and (f) selecting the peptide if it block leukocyte recruitment in step (e).

In one embodiment, the method further comprises the steps of (e) further testing the peptide for its ability to inhibit tumor metastasis in an animal bearing a solid tumor; and (f) selecting the peptide if it inhibits tumor metastasis in step (e).

In one embodiment, the method further comprises the steps of (e) further testing the peptide for its ability to inhibit tumor metastasis to the lungs and liver in an animal bearing a solid tumor known to metastasize the lungs or liver; and (f) selecting the peptide if it inhibits tumor metastasis in step (e).

In one embodiment, the method further comprises the steps of (e) further testing the peptide for its ability to treat sepsis in a patient; and (f) selecting the peptide if it treats sepsis in step (e).

In one embodiment, the method further comprises the steps of (e) further testing the peptide for its ability to treat bacterial sepsis in a patient; and (f) selecting the peptide if it treats sepsis in step (e).

In one embodiment, the method further comprises the steps of (e) further testing the peptide for its ability to treat acute kidney damage in a patient; and (f) selecting the peptide if it treats acute kidney damage in step (e).

In one embodiment, step (a) in the method includes screening a library of test peptides for their ability to bind to DPEP-1.

In one embodiment, the method further comprises identify other secondary targets involved in inflammation including co-factors, co-receptors, circulating factors and accessory proteins by using the LSALT peptide in a protein microarray.

All publications and patent applications mentioned in this specification are herein incorporated by reference to the same extent as if each independent publication or patent application is specifically and individually indicated to be incorporated by reference.

EXAMPLES

Example 1

Characterization of Renal Dipeptidase (DPEP-1) in the Kidney

Figure 1B:
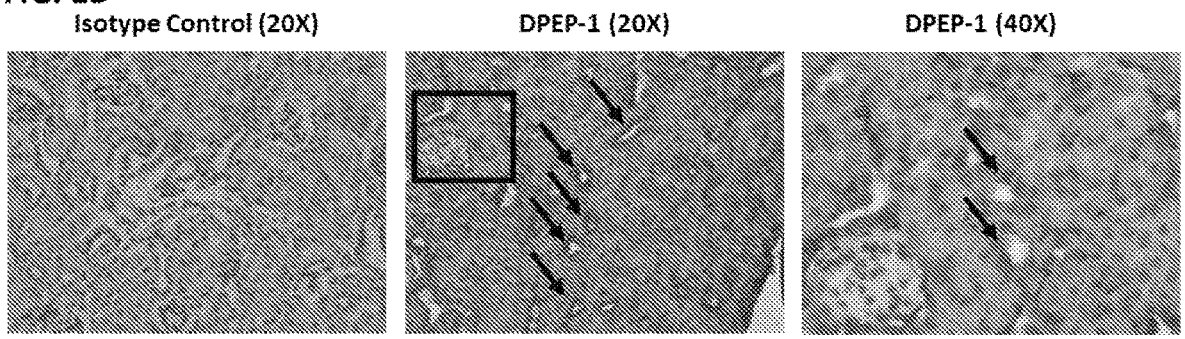
FIG. 1B provides representative photomicrographs of mouse kidney tissue was stained with DPEP-1 antibody and visualized using immunoperoxidase. Arrows indicate tubules that are positive for DPEP-1, as indicated by dark staining.
Figure 1C:
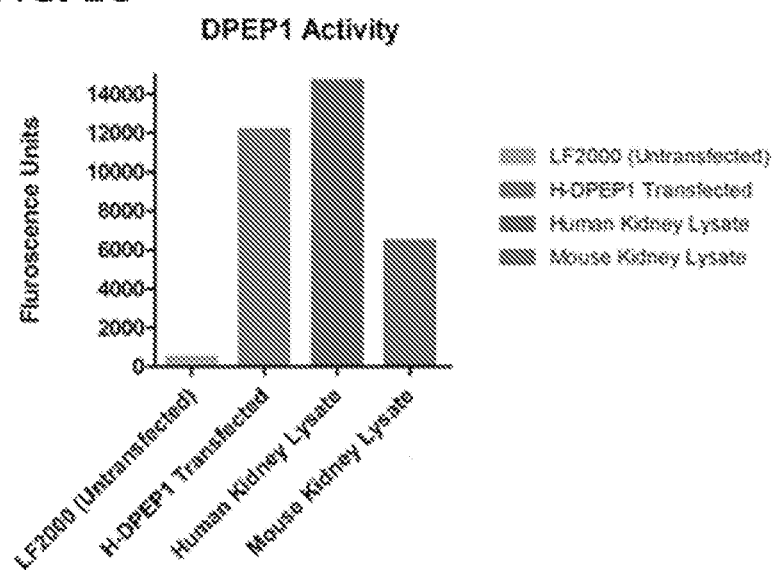
FIG. 1C provides a graph showing DPEP-1 enzymatic activity of total protein lysates prepared from untransfected COS-7 cells, COS-7 cells overexpressing DPEP-1, human kidney tissue, and mouse kidney tissue.

Renal tubular epithelial cells (TEC) were isolated and cultured from human kidney nephrectomies. Cells were then labeled with DPEP-1 and ZO-1 (a TEC surface marker) antibodies and imaged using confocal microscopy. Images were taken at 60× magnification. Representative photomicrographs are shown in FIG. 1A. Mouse kidney tissue was stained with DPEP-1 antibody and visualized using immunoperoxidase. Arrows indicate tubules that are positive for DPEP-1 as indicated by dark brown staining. Representative photomicrographs are shown in FIG. 1B. Total protein lysates were prepared from untransfected COS-7 cells, COS-7 cells overexpressing DPEP-1, human kidney tissue, and mouse kidney tissue. Lysates were then tested for DPEP-1 enzymatic activity by via fluorometric detection of the breakdown of glycine-dehydro-phenylalanine (Gly-D-Phe), a dipeptide substrate for DPEP-1. These results are shown graphically in FIG. 1C Example 2

Endogenous DPEP-1 Activity in Vivo

Figure 2:
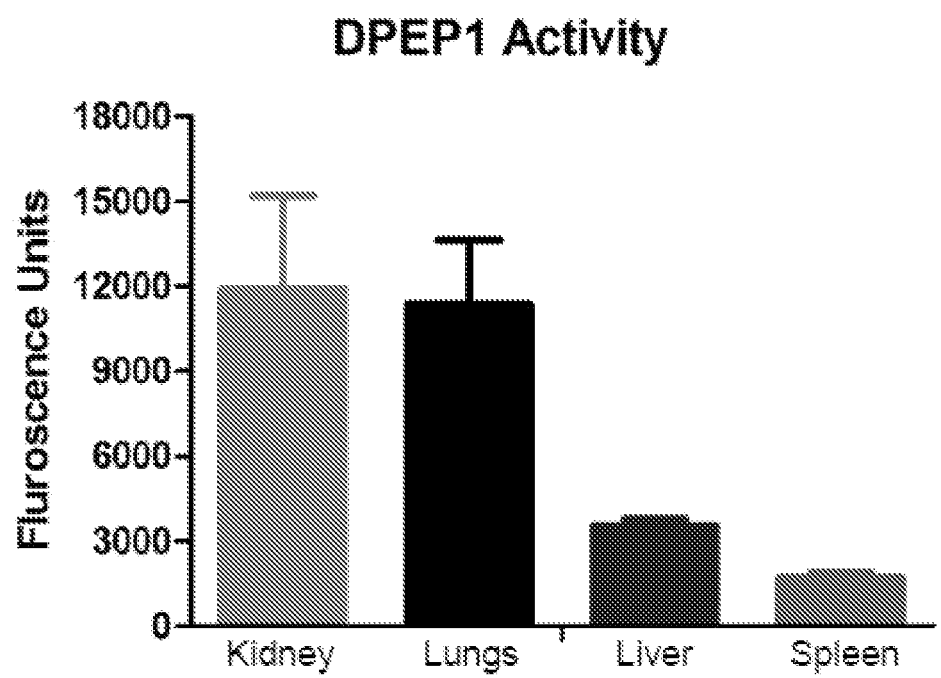
FIG. 2 provides a graph showing DPEP-1 enzymatic activity of total protein lysates isolated from organs (Lungs, Liver, Spleen and Kidney) harvested from 8-10 weeks old C57/BL6 animals.

Organs (Lungs, Liver, Spleen and Kidney) were harvested from 8-10 weeks old C57/BL6 animals (Charles River). Proteins were isolated from tissues using RIPA/Octyl-glucoside in the absence of protease inhibitor cocktails using a tissue homogenizer. 10 µl of the protein lysate from each condition/organ was used to perform DPEP-1 enzyme activity assay. These results are shown graphically in FIG. 2.

Example 3

Lung Eexpression of DPEP-1

Figure 3:
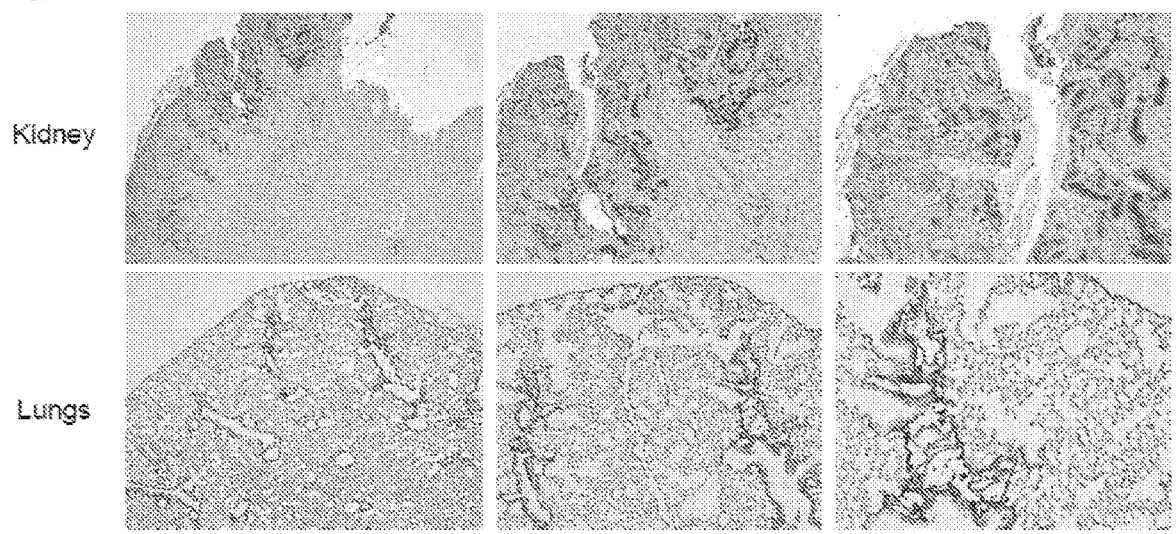
FIG. 3 provides representative photomicrographs of mouse kidney and lung sections stained with a DPEP-1 specific antibody (dark (Abcam)] using the DAB method to assess DPEP-1 expression.

Organs (Lungs, and Kidney) were harvested from 8-10 weeks old C57/BL6 animals (Charles River) and tissues were paraffin embedded for histology. Kidney and lung sections were stained with a DPEP-1 specific antibody (dark (Abcam) using the DAB method to assess DPEP-1 expression. Representative photomicrographs are shown in FIG. 3.

Example 4

Catalytic Activity of DPEP-1 is not Required for Binding in Vitro

Figure 4A:
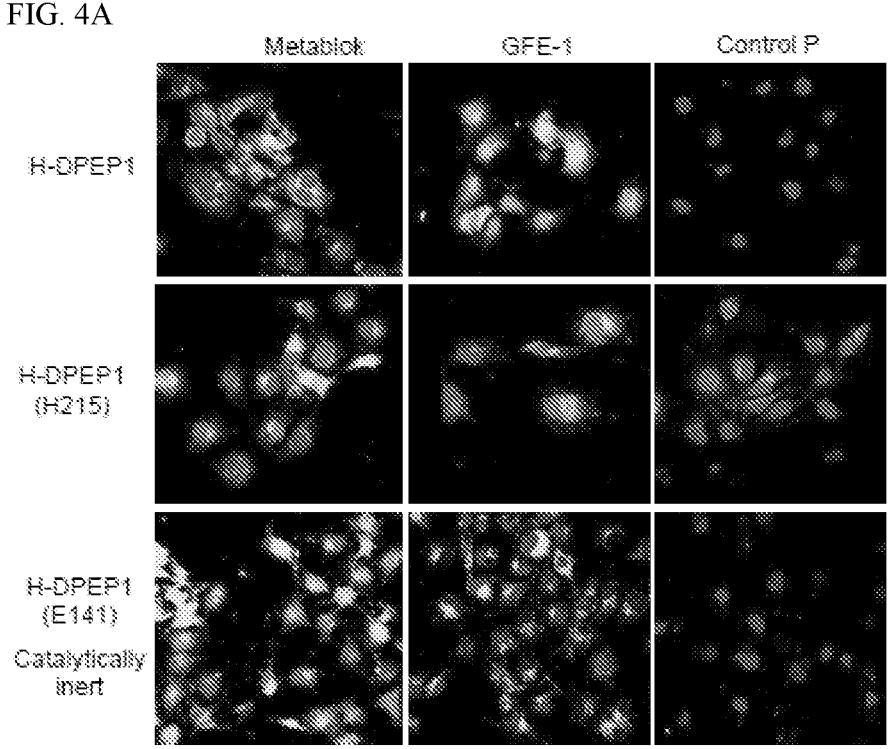
FIG. 4A provides representative photomicrographs of fluorescently labelled peptide binding to Cos1 cells transfected with wildtype human DPEP1, or mutated human DPEP1, as indicated. The LSALT peptide is also referred to as Metablok. GFE-1 is a positive control peptide discovered by Ruoslahti et al., known to bind to DPEP1, thus acting as a positive control. The negative control peptide (Control P) only shows fluorescence of the DAPI nuclear counter stain. The enzymatic activities of each of wild type and mutant (E>D, H>K) DPEP1 constructs in the presence or absence of Cilastatin or Penicillamine are shown graphically in FIG. 4B. A photograph of the western blot for confirming expression of the transfected proteins in the Cos1 cells is shown in FIG. 4C.
Figure 4B:
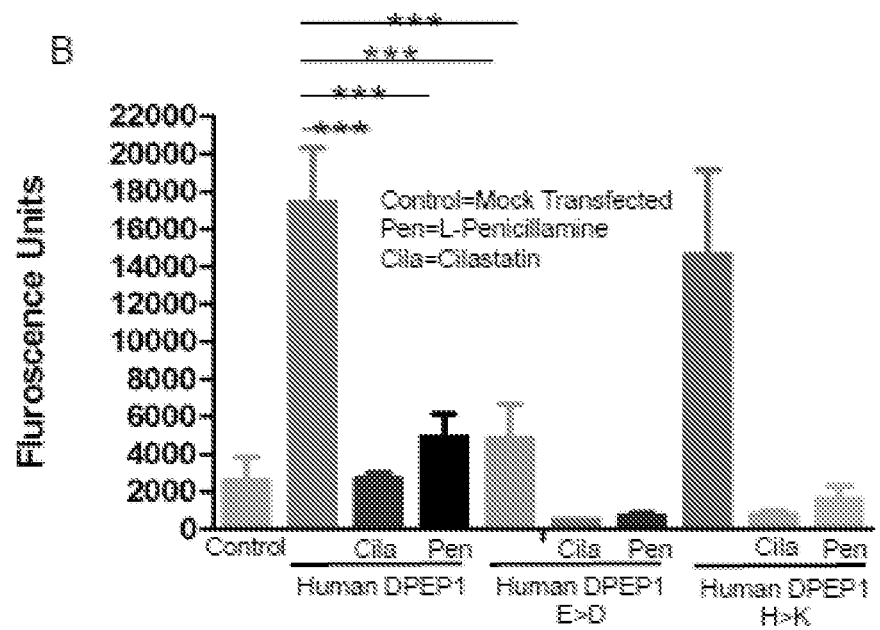
Figure 4C:
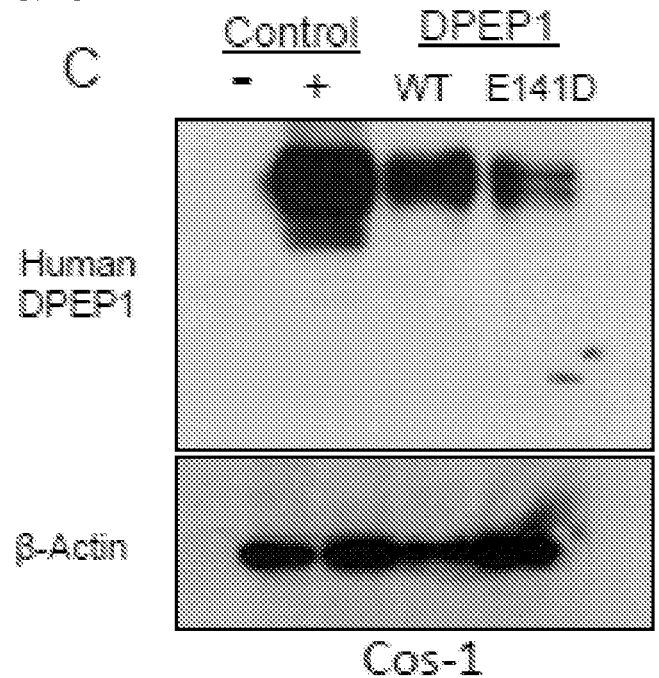

Cos-1 cells were transiently transfected with 3 µg of either the wild type membrane dipeptidase (DPEP-1) catalytically inert mutant (E>D) or mutant contol (H>K) corresponding to the human DPEP-1 gene using lipofectamine 2000 (Invitrogen) reagent. 24 hours after transfection, DPEP-1 expressing cells weer reseeded on 24 well collagen coated (neutralized) plates and allowed to grow for 24 hours at 37° C. 24 hours after seeding, media was removed and cells were washed with PBS. Cells were blocked with FBS/NBSA/Tween in PBS for 30 minutes on ice. Cells were then washed with PBS and incubated with Alexa-488 (green) conjugated LSALT, GFE-1, control peptide or DPEP-1 antibody (1/100) (Sigma) on ice for 30 minutes. After incubation, cells were washed with PBS and stained with DAPI for 4 minutes on ice. Cells were again washed with PBS, fixed using 4% paraformaldehyde and immunofluoresence microscopy was performed to assess binding. Representative photomicrographs of each experimental condition (n=3) are shown in FIG. 4A. Proteins from human DPEP-1 transfected cells were isolated after 48 hours using octyl-glucoside/RIPA in the absence of protease inhibitors. Membrane dipeptidase activity assay and the fluorometric detection of D-Phe was performed exactly as described earlier according to the principles originally established by Heywood and Hooper (1995). These results are shown graphically in FIG. 4B. Values shown are the mean ±s.e.m. from six independent experiments; asterisks (***) indicate P<0.001 as compared with DPEP-1 transfected cells (one-way ANOVA with the Neuman-Keuls post-test)(n=5). Proteins from transfected cells were isolated after 48 hours using octyl-glucoside/RIPA lysis buffer and western blot analysis was performed to assess DPEP-1 expression using DPEP-1 antibody (Sigma). A photograph of the western blot analysis is shown in FIG. 4C.

Example 5

LSALT Binds to Racine and Human DPEP-1

Figure 5C:
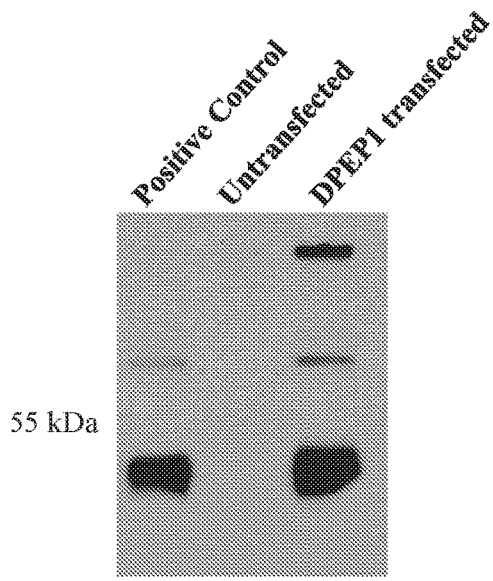
FIG. 5A-D provide representative photomicrographs of fluorescently labelled peptide binding to Cos-1 cells transiently transfected with membrane dipeptidase (DPEP-1) cDNA corresponding to the rat (FIG. 5A), human (FIG. 5B), or dog DPEP-1 (FIG. 5C) gene. The control peptide only shows fluorescence of the DAPI nuclear counterstain A photograph of the western blot confirming DPEP1 expression in transfected Cos1 cells is provided in FIG. 5D. A schematic of the biotin transfer method, in which LSALT peptide is linked to a transferable biotin, allowed to interact with cell bound DPEP1, then transfers the biotin to DPEP1 by activation with UV light. Biotinylated DPEP1 can then be affinity precipitated using neutravidin beads. The proteins on the beads are analysed by western blot for DPEP1, confirming that LSALT (and GFE-1, but not the KGAL control peptide) was indeed able to interact with DPEP1, as provided in FIG. 5E.
Figure 5D:
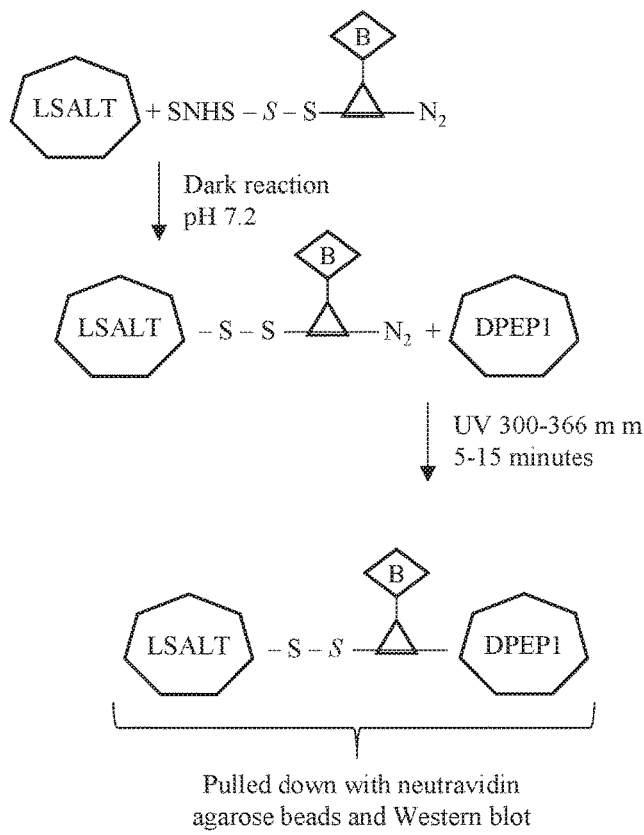
Figure 5D:
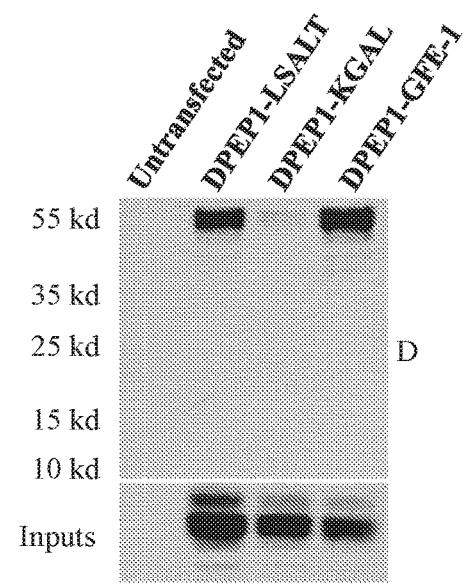
Figure 5E:
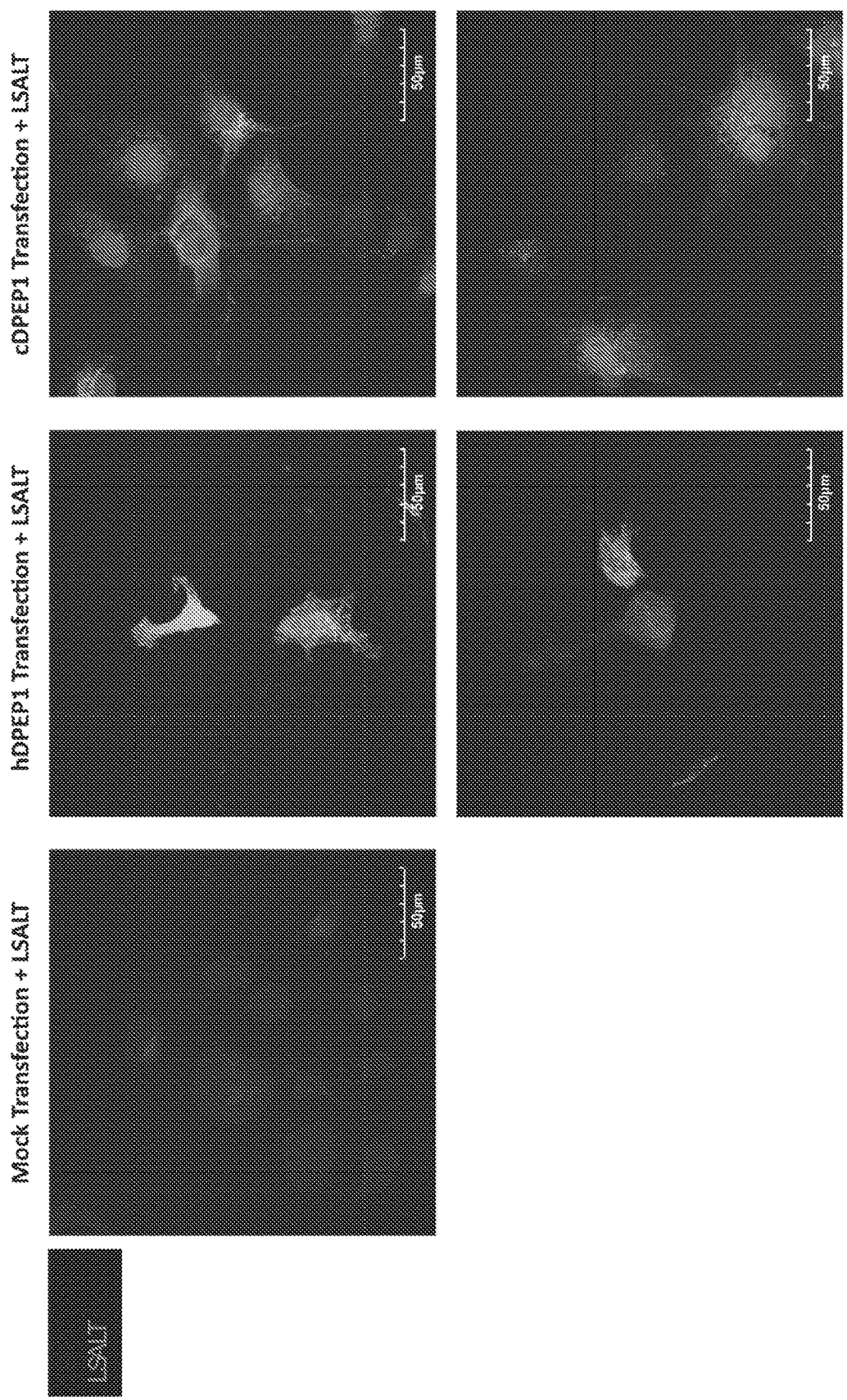

Cos-1 cells were transiently transfected with either 3 or 5 µg of membrane dipeptidase (DPEP-1) cDNA corresponding to the rat (Shown in FIG. 5A), human (Shown in FIG. 5B), or canine (Shown in FIG. 5E) DPEP-1 gene using Lipofectamine 2000 (Invitrogen) reagent in OptiMEM medium. 24 hours after transfection, DPEP-1 expresisng cells were re-seeded on collagen coated (neutralized) wells in 24 well plates and allowed to grow for 24 hours at 37° C. 24 hours after seeding, media was removed and cells were washed with PBS. Cells were blocked with FBS/NBSA/Tween in PBS for 30 minutes on ice. Cells were then washed with PBS and incubated with Alexa-488 (green) conjugated LSALT, GFE-1, control peptide or DPEP-1 antibody (1/100) (Sigma) on ice for 30 minutes. DPEP-1 antibody incubated cells were washed with PBS and incubated with flourescently conjugated anti-rabbit secondary antibody (1/500 in PBS) for 30 minutes on ice. After incubation, cells were washed with PBS and stained with DAPI for 5 minutes on ice. Cells were then washed with PBS and fixed using 4% paraformaldehyde and immunofluorescne microscopy was performed to assess binding. Shown are representative photomicrographs of each experimental condition (n=5). Proteins from human DPEP-1 transfected cells were isolated after 48 hours using octyl-glucoside/RIPA lysis buffer and western blot analysis was performed to assess DPEP-1 expression using a DPEP-1 specific antibody (Sigma). A photograph of the western blot is provided in FIG. 5D. Cos-1 cells were transiently transfected with 3 µg of DPEP-1 encoding the human DPEP-1 gene. Transfected cells were serum starved in OptiMEM medium for 2 hours and treated with methyl-beta-cyclodextrin for 30 minutes. After incubation, cells were washed with PBS and treated with 10 mg/ml biotin transfer peptide (LSALT, GFE-1 or Control Peptide (KGAL)] for 10 minutes. Cells were then washed with PBS and biotin transfer was enabled by UV activation of the aryl azide groups for 15 minutes at 363 nm. Residual fluid was removed and monolayers were lysed either with octyl-glucoside/RIPA or 8M urea. Isolated supernatants were rotated with 50 µl of neutr-avidin agarose beads at 4° C. for 24 hours. Beads were washed with corresponding buffers, boiled in Laemmli buffer and analyzed by western blot using a DPEP-1 specific antibody (Proteintech). A schematic of this procedure and photograph of the resulting western blot are provided in FIG. 5E.

Example 6

LSALT Peptide does not Bind to Human DPEP2 and DPEP3 in Vitro

Figure 6A:
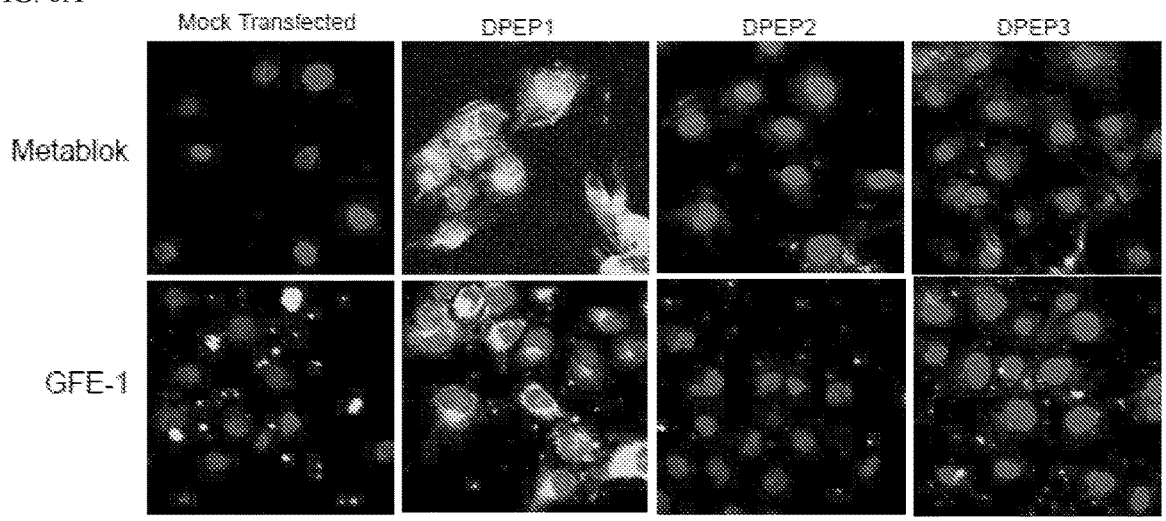
FIG. 6A provides representative photomicrographs of fluorescently labelled Metablok (LSALT) or GFE-1 (positive control peptide) to Cos-1 cells transiently transfected with human DPEP-1, DPEP-2, or DPEP-3 gene. Fluorescent peptide binding is only seen with DPEP1 transfection; all other images show only fluorescence of the DAPI nuclear counterstain. Proteins from DPEP-1, DPEP2 and DPEP3 transfected cells were isolated, and photographs of the western blots confirming protein expression are shown in FIG. 6B.
Figure 6B:
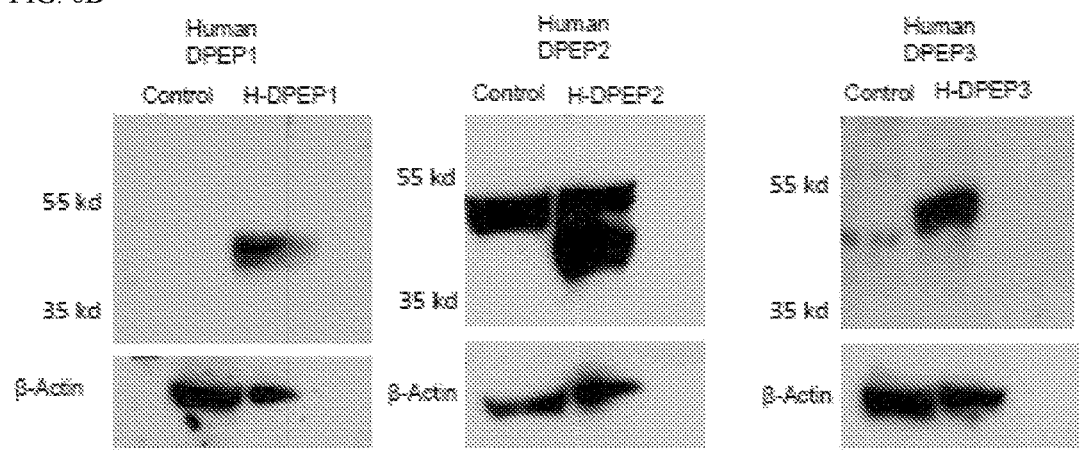

Cos-1 cells were transiently transfected with either 3 µg of human DPEP-1, DPEP2, or DPEP3 gene using Lipofectamine 2000 (Invitrogen) reagent in OptiMEM medium. 24 hours after transfection, DPEP-1, DPEP2, or DPEP3 expressing cells were re-seeded on collagen coated (neutralized) wells in 24 well plates and allowed to grow for 24 hours at 37° C. 24 hours after seeding, media was removed and cells were washed with PBS. Cells were blocked with FBS/NBSA/Tween in PBS for 30 minutes on ice. Cells were then washed with PBS and incubated with LSALT or GFE-1, conjugated with Alexa-488 (green). After incubation, cells were washed with PBS and stained with DAPI for 5 minutes on ice. Cells were then washed with PBS and fixed using 4% paraformaldehyde and immunofluorescence microscopy was performed to assess binding. Representative photomicrographs are shown for each experimental condition (n=3) in FIG. 6A. Proteins from DPEP-1, DPEP2 and DPEP3 transfected cells were isolated after 48 hours using octyl-glucoside/RIPA lysis buffer and western blot analysis was performed to assess DPEP-1, DPEP2 and DPEP3 protein expression using specific antibodies; DPEP-1 antibody (Sigma), DPEP2 (Abcam) and DPEP3 (Santacruz). Blots were stripped and reprobed with an anti-β-actin. Photographs of the western blots are shown in FIG. 6B.

Example 7

Figure 7A:
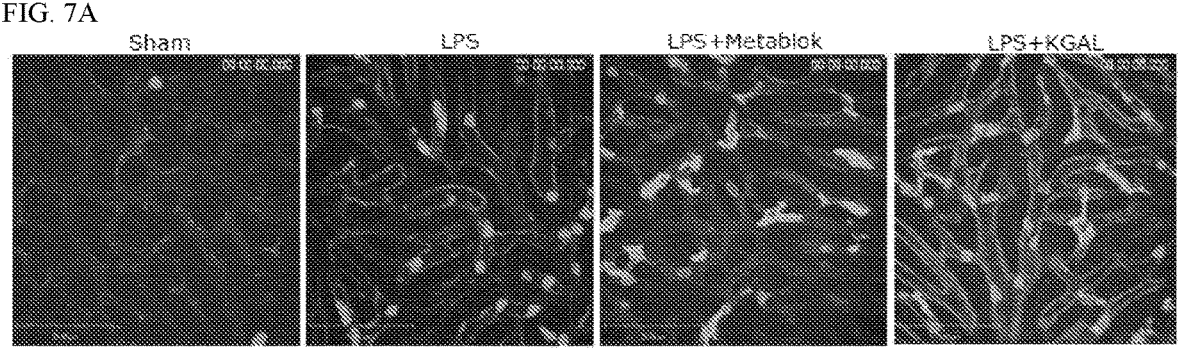
FIG. 7A and B provides an image and graph showing LSALT inhibits neutrophil adhesion in the hepatic sinusoids in the presence of LPS. Metablok is synonymous with the LSALT peptide. KGAL is a control peptide.
Figure 7B:
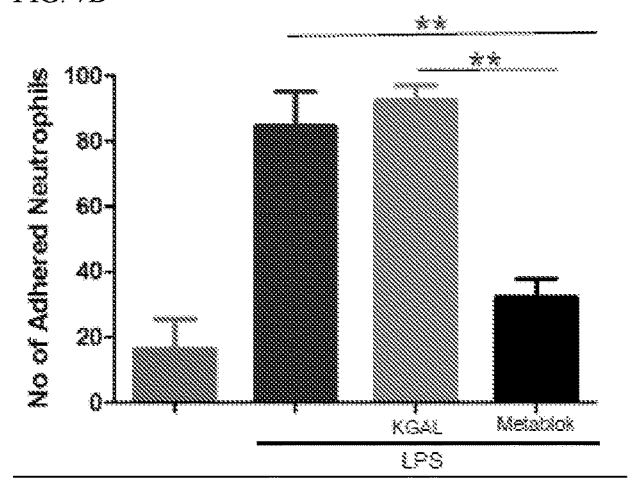

LSALT Inhibits Neutrophil Adhesion in the Hepatic Sinusoids in the Presence of LPS Six to ten week old LysM$^{(gfp)}$ mice were injected with 1 mM dose of LSALT or 1KGAL (control) (intravenous) 5 minutes after the injection of 0.5 mg/kg of lipopolysaccharide (intraperitoneal). After 3 hours, animals were injected with ketamine and xylazine to provide general anesthesia. Fluorescently conjugated F4/80 and PECAM-1 antibodies were then administered via jugular vein cannulation and intravital spinning disk confocal microscopy was performed. The livers were imaged for an hour and the number of neutrophils were counted at different time points. Neutrophils which were stationary for ≥30 seconds in the liver sinusoids were counted as adherent cells. Data are representative of three independent experiments. An unpaired 2-tailed student's t-test was performed comparing LSALT, GFE-1 or control treated group against the LPS treated group (*p<0.05). The results are shown in FIG. 7.

Example 8

Expression of DPEP-1 Enhanced the Binding of LSALT and GFE-1 in COS-7 Cells

Figure 8:
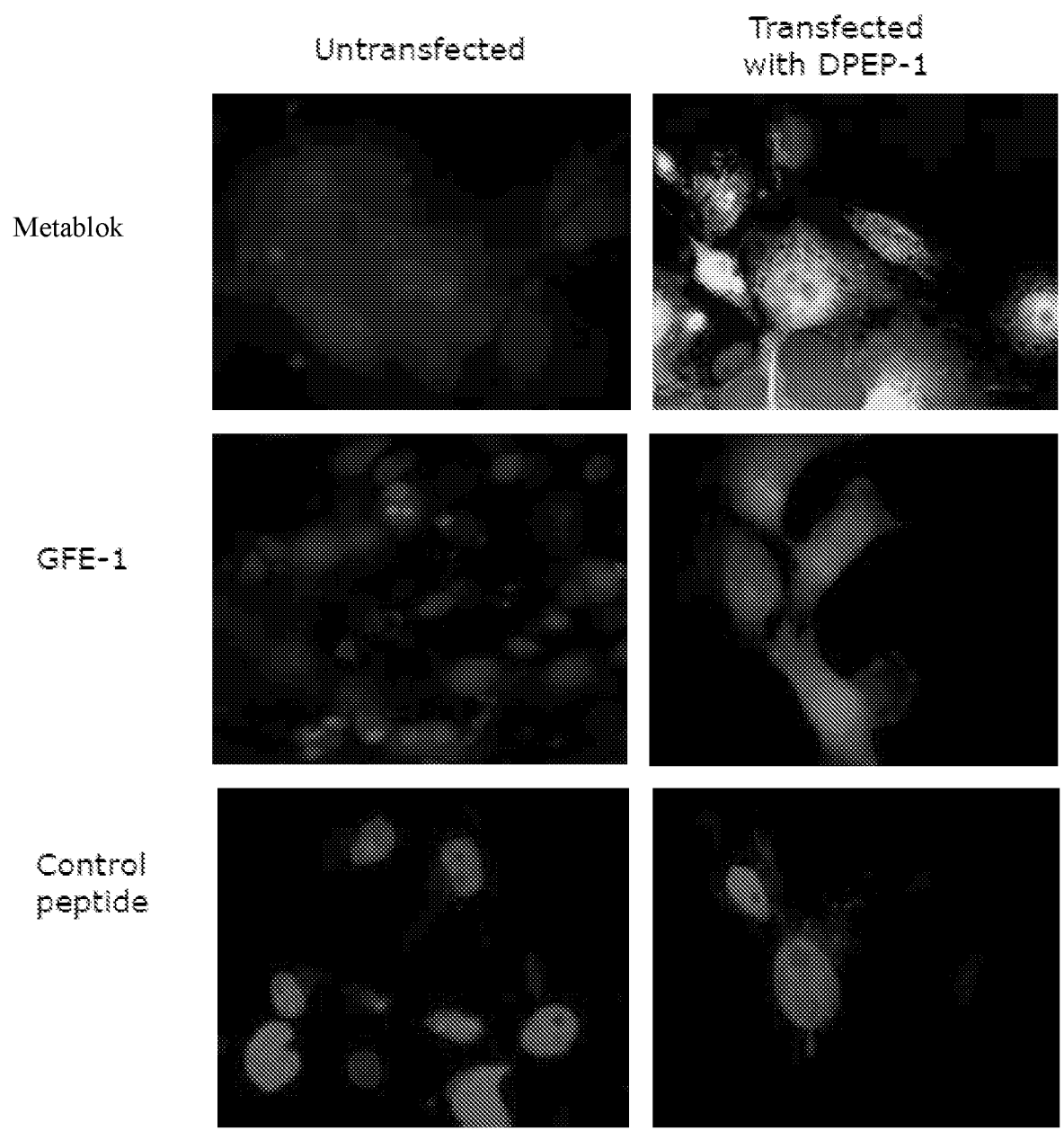
FIG. 8 provides photomicrographs showing expression of DPEP-1 enhanced the binding of fluorescently-labelled LSALT in Cos-7 cells. Metablok is the LSALT peptide. GFE-1 is another DPEP-1 binding peptide used as a positive control.

Cos-7 cells were transiently transfected with 5 µg of renal rat membrane dipeptidase (DPEP-1) plasmid using Lipofectamine 2000 (Invitrogen) reagent. 48 hours after transfection, media was removed, and cells were washed with PBS. Cells were incubated with LSALT or GFE-1 conjugated with Alexa-488 (Green), or control peptide conjugated with Alexa-488 (Green) on ice for 30 minutes. Cells were washed and fixed using 4% paraformaldehyde and immunofluorescence microscopy was performed to assess binding. Shown are representative photomicrographs of each experimental condition (n=2). The results are shown in FIG. 8.

Example 9

Expression of DPEP-1 Enhanced the Binding of LSALT to COS-7 Cells

Figure 9:
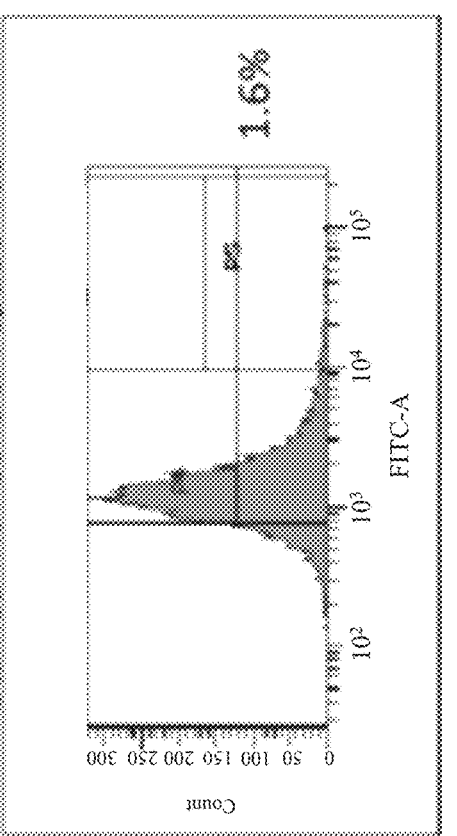
FIG. 9 provides single parameter flow cytometry histograms showing that expression of DPEP-1 enhanced the binding of LSALT to Cos-7 cells.
Figure 9:
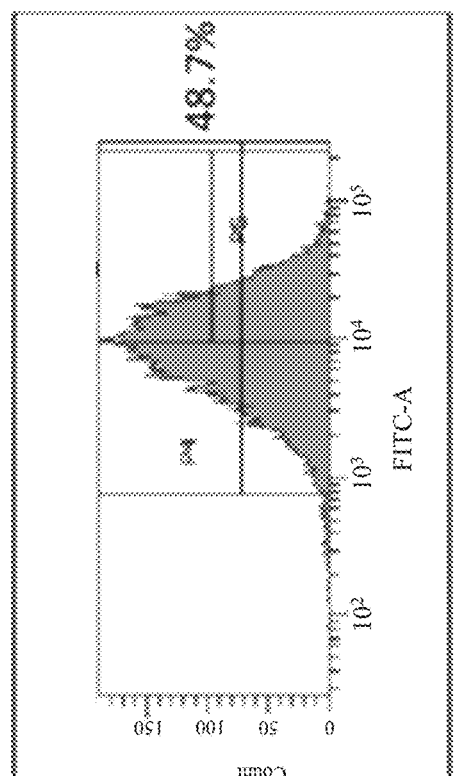
Figure 9:
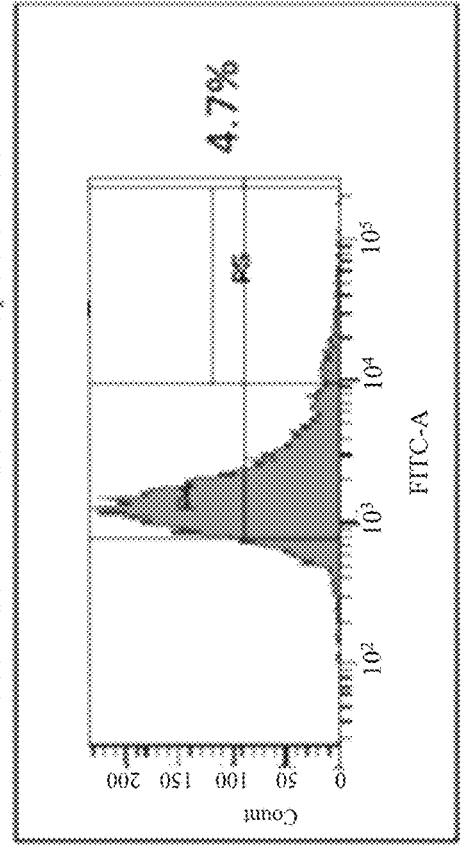
Figure 9:
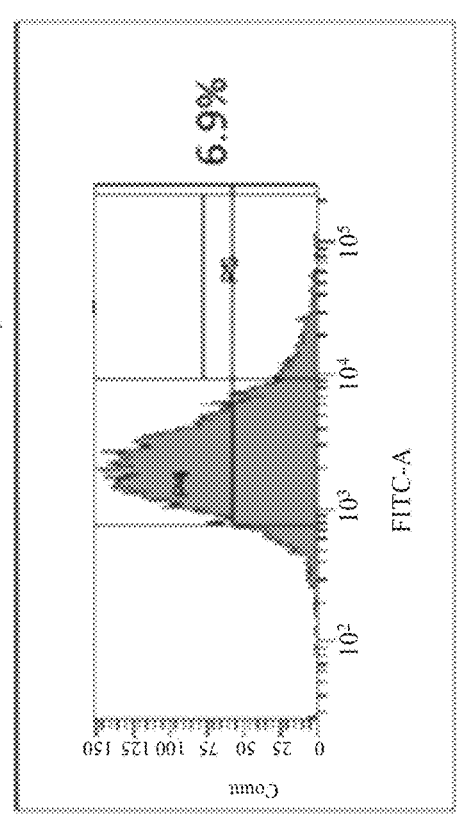

Cos-7 cells were transiently transfected with 5 µg of renal rat membrane dipeptidase (DPEP-1) plasmid using lipofectamine2000 (Invitrogen) reagent. 48 hours after transfection, cells were incubated with LSALT conjugated to Alexa-488 (green) on ice for 30 minutes. Cells were washed and flow cytometry was performed to assess binding. Shown are single parameter histograms for each experimental condition (n=2). The results are shown in FIG. 9.

Example 10

LSALT Does not Inhibit Membrane Dipeptidase (DPEP-1) Enzyme Activity

Figure 10A:
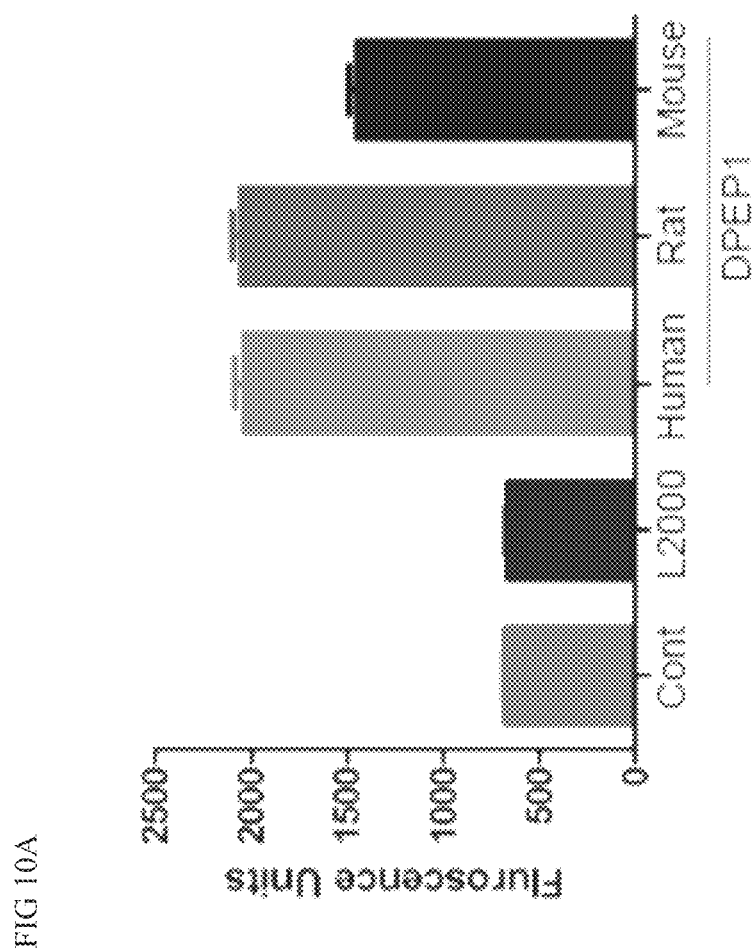
FIG. 10A demonstrates that the enzymatic activity of human, rat or mouse DPEP1 can be measured after Cos1 cells are transfected with each of these genes. L2000 indicates Cos1 cells were mock transfected with only the Lipofectamine 2000 vehicle.
Figure 10B:
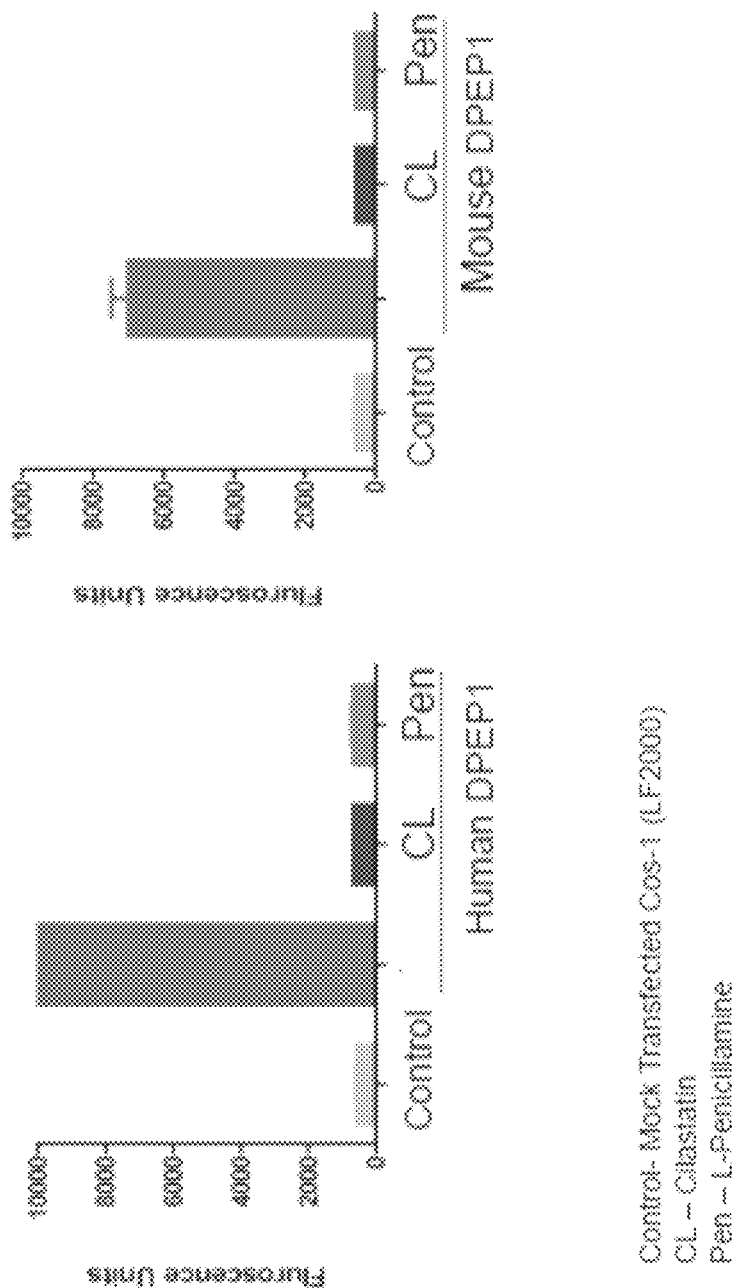
FIG. 10B shows that the enzymatic activity of human or mouse DPEP1 can be inhibited by cilastatin (CL) or penicillamine (Pen).
Figure 10C:
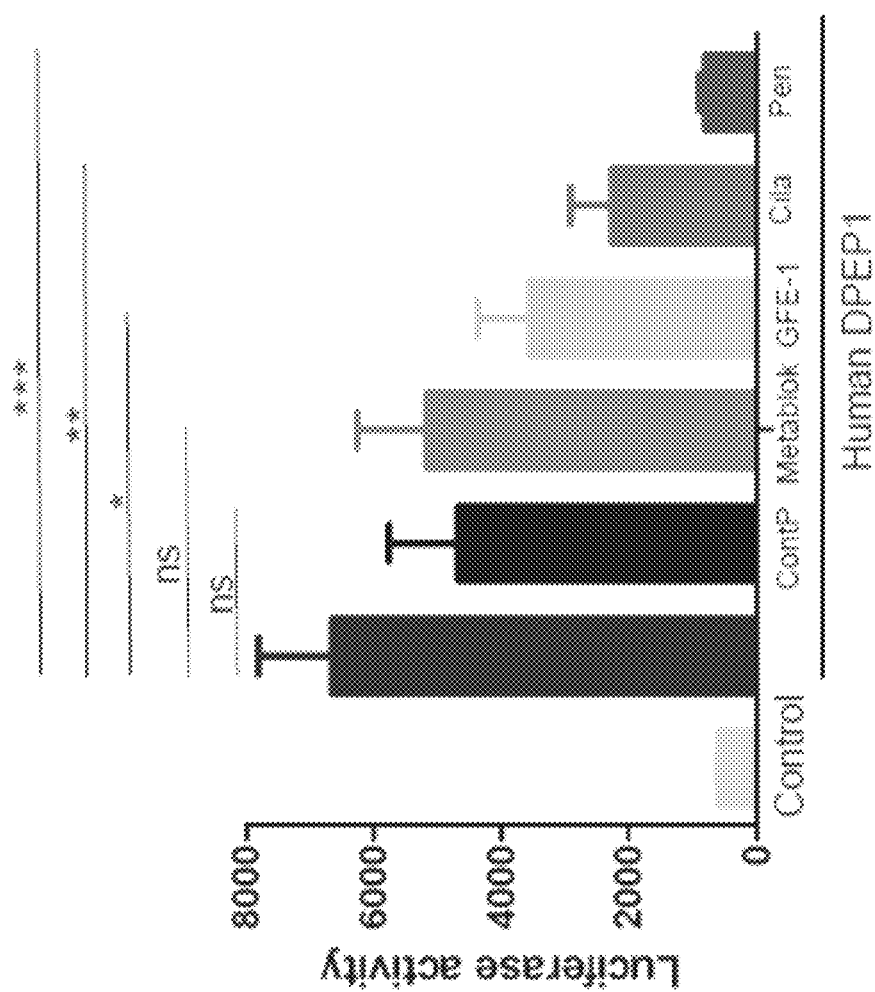
FIG. 10C provides graphs showing that LSALT and GFE-1 do not inhibit membrane dipeptidase enzyme activity. Metablok is the LSALT peptide. GFE-1 is another DPEP-1 binding peptide used as a control.

Cos-1 cells were transiently transfected with 3 µg of human membrane dipeptidase (DPEP-1) plasmid using lipofectamine 2000 (Invitrogen) reagent. 48 hours after transfection, media was removed, and cells were washed with PBS. Proteins were isolated using octylglucoside in the absence of protease inhibitors. Membrane dipeptidase assay and the fluorimetric detection of D-Phe was performed exactly as described by Heywood and Hooper previously. In brief, proteins were first incubated with membrane dipeptidase substrate Gly-D-Phe either in the presence or absence of LSALT or GFE-1 peptide at 37° C. for 3 hours. The fluorescence signal generated from the conversion of D-Phe to 6,69-dihydroxy-(1,19-biphenyl)-3,39-diaceticacid in the presence of D-aminoacidoxidase and peroxidase was measured using a fluorescence plate reader. The results are shown in FIGS. 10A-C.

Example 11

Inhibition of Remal Dipeptidase During Sepsis Reduces Inflammation

Figure 11A:
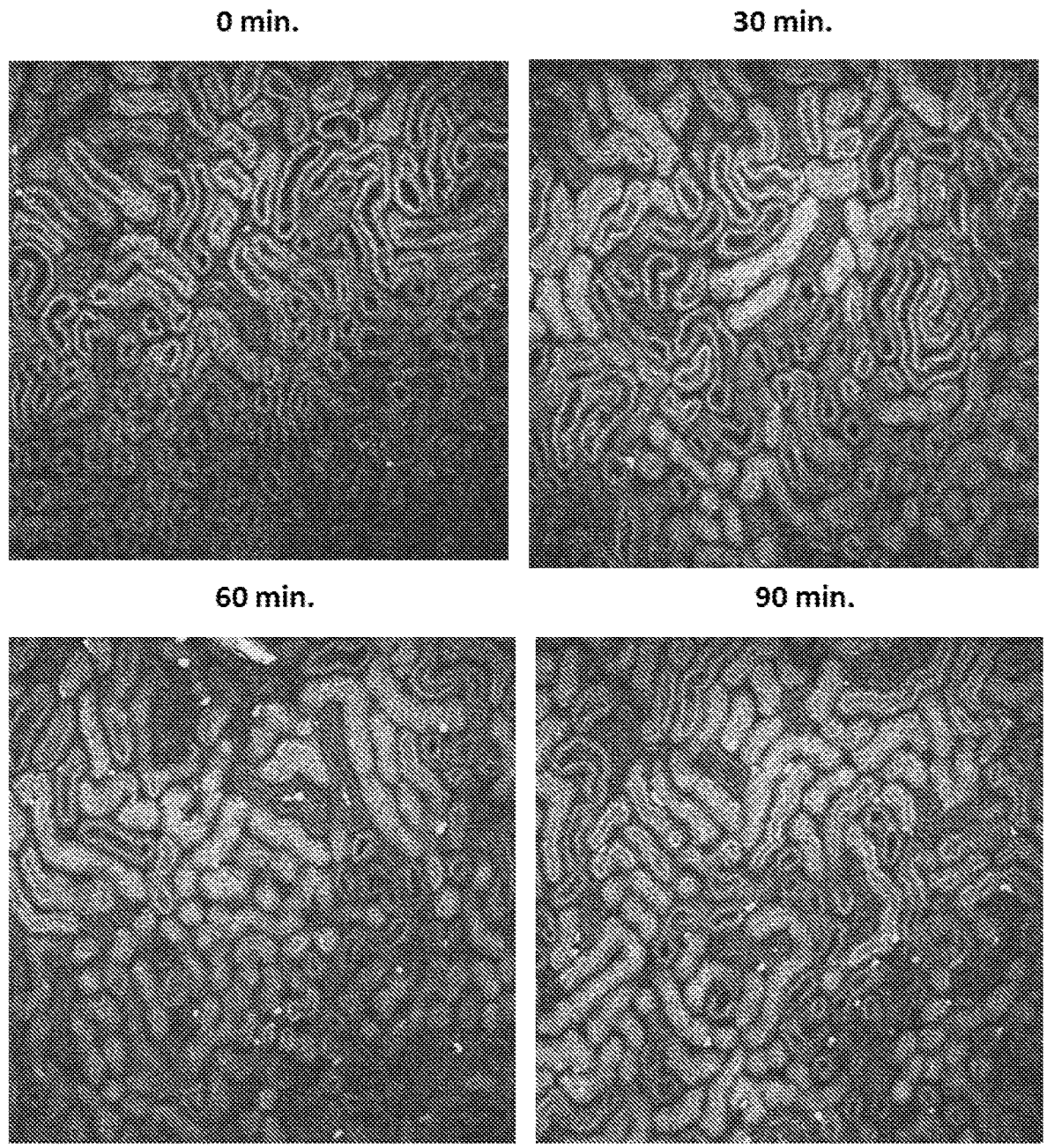
FIG. 11A demonstrates the effect of LPS administration on leukocyte recruitment to the kidney measured by intravital microscopy.
Figure 11B:
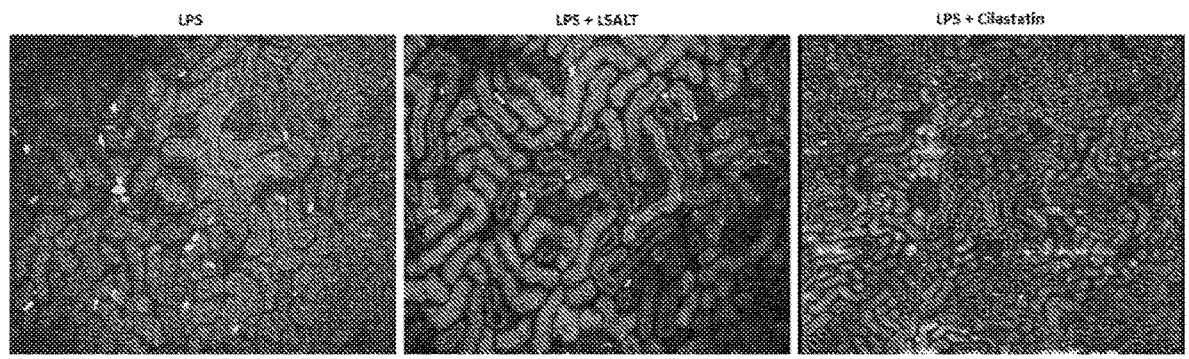
FIG. 11B,C demonstrate the effect of LSALT peptide or cilastatin on neutrophil recruitment to the kidney following an inflammatory dose of systemic LPS. Cilastatin is a dipeptidase-1 inhibitor and used as a control.
Figure 11C:
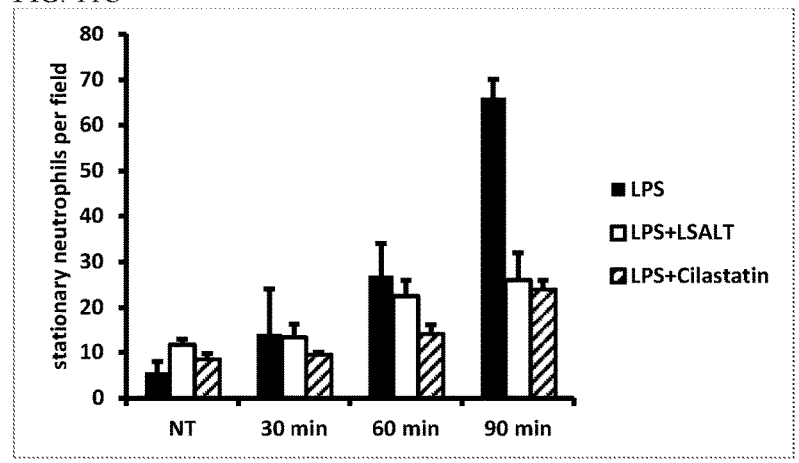

LysM$^{(gfp)}$ mice were subjected to endotoxemia via intravenous injection of lipopolysaccharide (LPS, O111:B4) at a dose of 5 mg/kg. The kidney was imaged using multiphoton microscopy every 30 min. for up to 90 min. Inhibitors of dipeptidase were used intravenously to pretreat mice 10 min. before LPS injection. Photomicrographs are shown in FIG. 11A. FIG. 11B provides photomicrographic images of kidney before (NT) and after LPS (90 min.) with various inhibitors. Adherent neutrophils were seen in interstitial spaces after IRI. Neutrophils were quantified over a 90 min. time course after LPS injection with various DPEP-1 inhibitors. n=2-3/group, *:p<0.05. These results are shown graphically in FIG. 11C.

Example 12

Figure 12A:
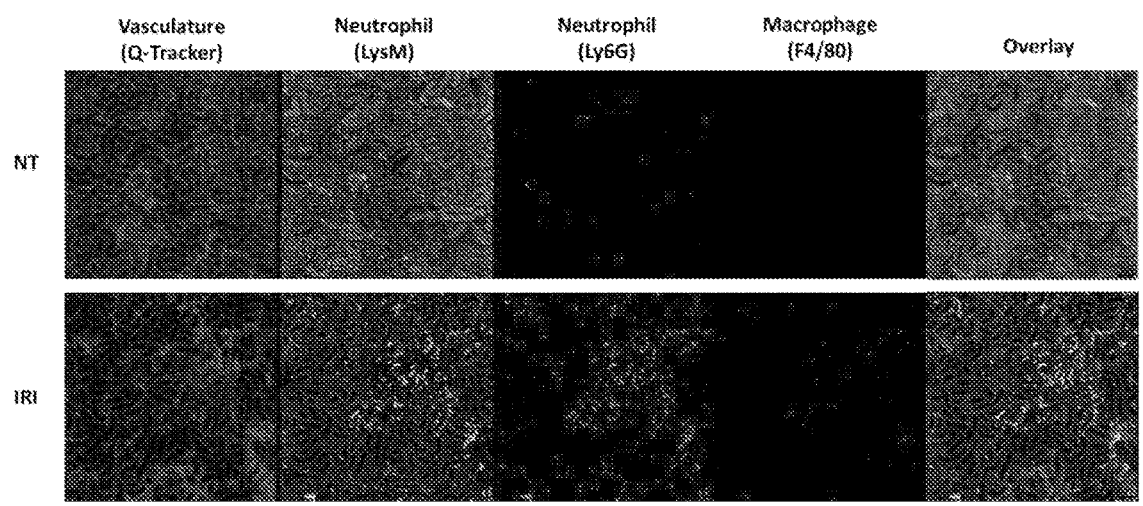
FIGS. 12A, B.
Figure 12B:
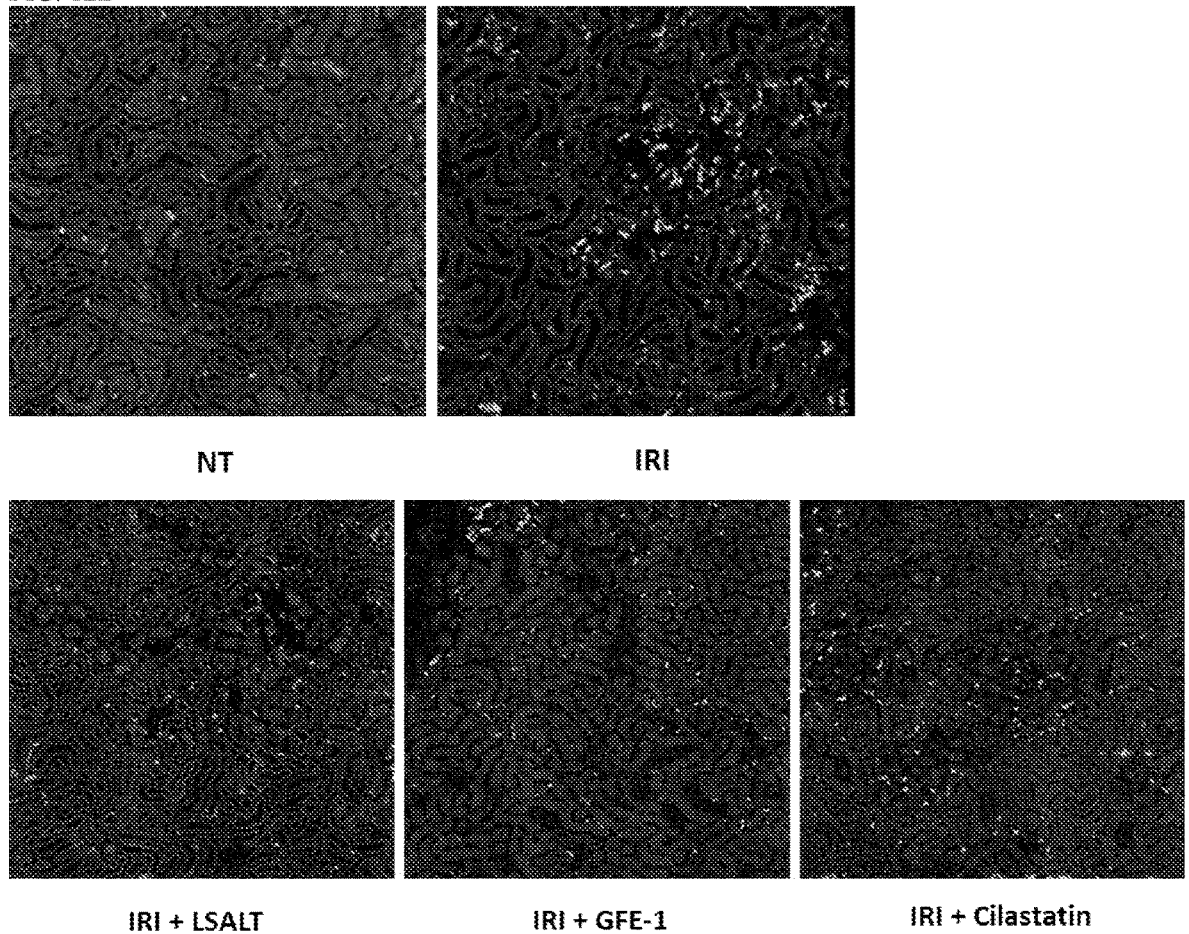
Figure 13A:
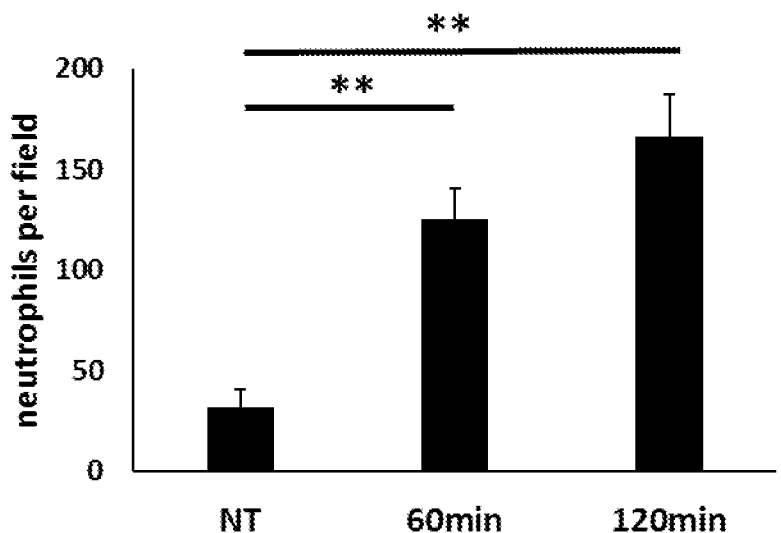
FIGS. 13A, B.
Figure 13B:
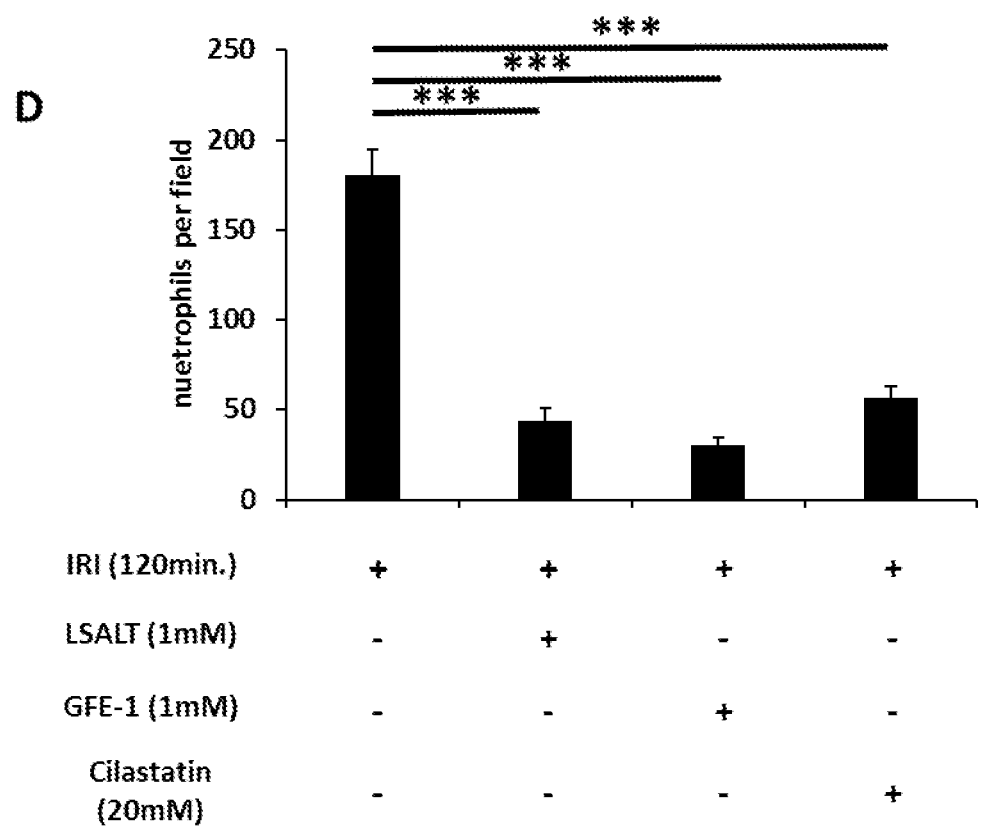

Inhibition of Dipeptidase During Remal Ischemia Reperfusin Injury Reduces Inflammation LysM$^{(gfp)}$ mice were subjected to 30 min. of unilateral renal ischemia at 37° C. via vascular clamp and 120 min. of reperfusion and the affected kidney was imaged using multiphoton microscopy. Representative photomicrographs are shown in FIG. 12A. Inhibitors of dipeptidase were used to pretreat mice 10 min before ischemia. Labeling antibodies were injected intravenously before imaging. Images of kidney before (NT) and after IRI (120 min.) with various inhibitors are provided in FIG. 12B. Adherent neutrophils were seen in interstitial spaces after IRI. Neutrophils were quantified over a 120 min. time course and shown graphically in FIG. 13A (n=3/group, *:p<0.01). Neutrophils were quantified after IRI (120 min.) with various inhibitors and shown graphically in FIG. 13B (n=3-5/group, *: p<0.001).

Example 14

Inhibition of Inflammatory Mediators by DPEP-1 Binding

Figure 14A:
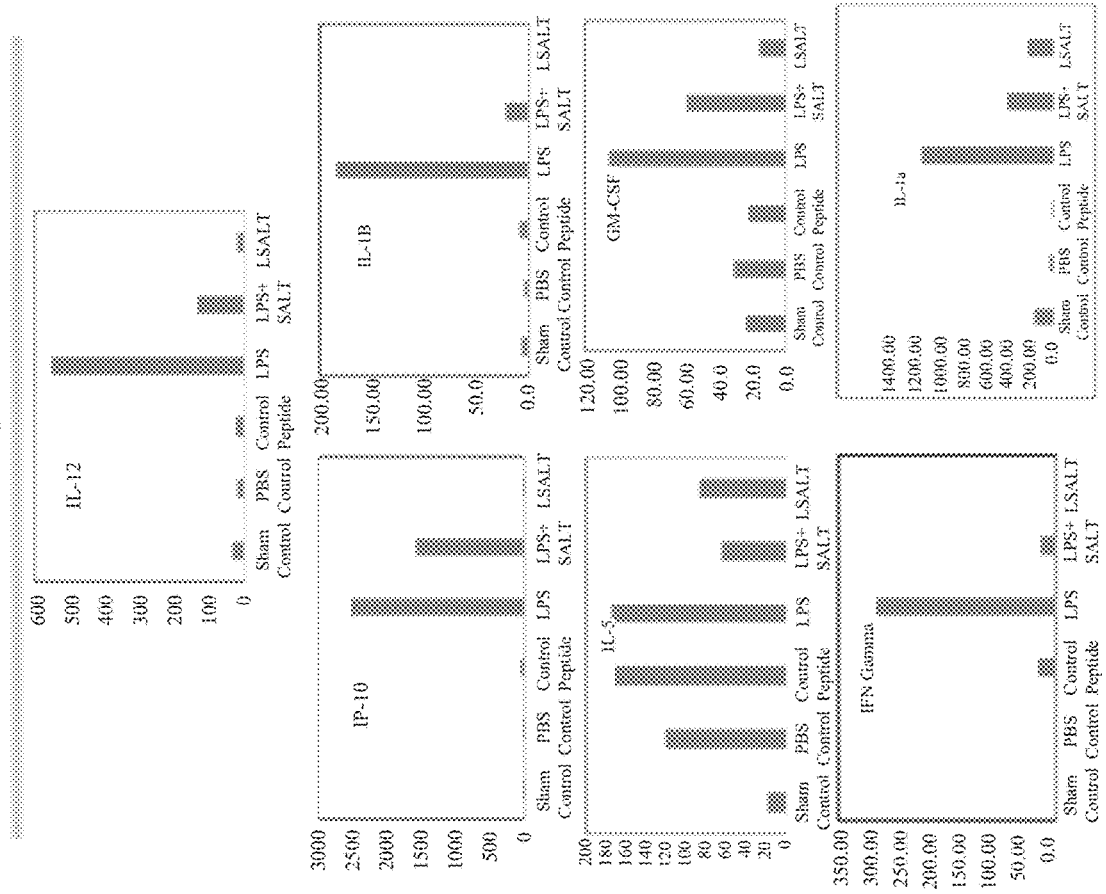
FIG. 14A provides graphs showing the reduction in inflammatory mediators induced by LPS in mice in the presence or absence of LSALT peptide.
Figure 14B:
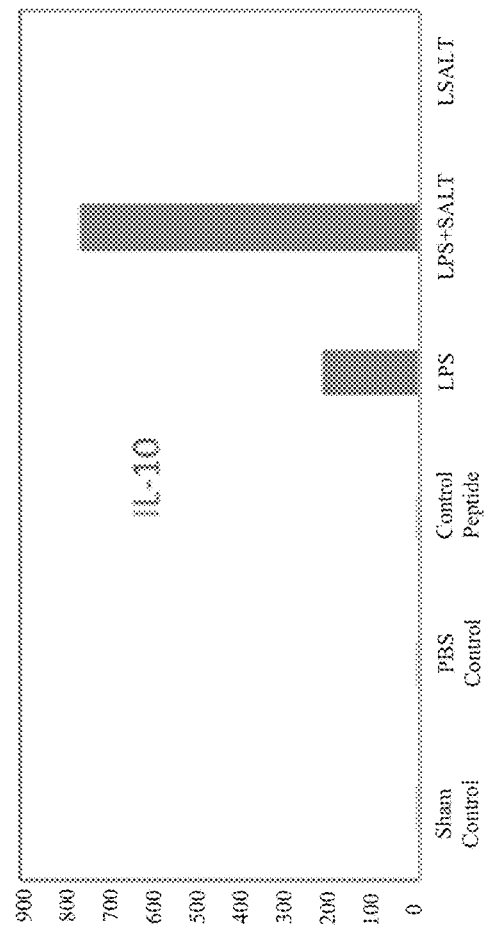
FIG. 14B provides graphs showing the increase in IL-10 induced by LSALT peptide during LPS challenge in mice.
Figure 14B:
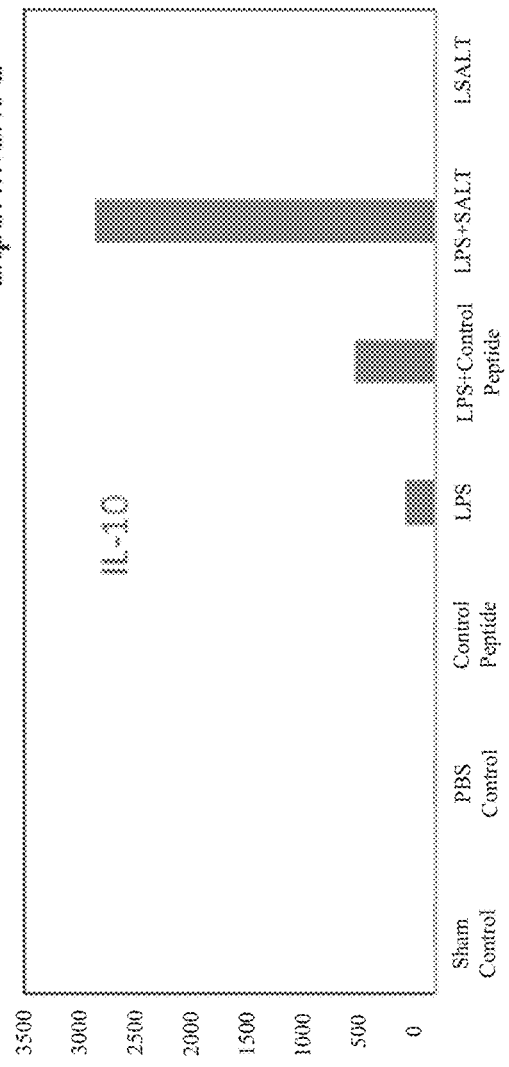

The following experiments were performed to assess if DPEP-1 binding by LSALT peptide had an effect on the level of specific serum cytokines in response to LPS. 6-8 weeks old SCID mice were given an intraperitoneal injection of LPS (0.5 mg/kg) 5 minutes prior to intravenous injection of LSALT peptide or a control peptide. 4 hours following injection of LPS, blood was collected by cardiac puncture and changes in plasma cytokine levels were assessed using Luminex Cytokine Arrays. Bar graphs show the levels of different inflammatory mediators released in the plasma in the presence or absence of LSALT peptide and control peptide. (FIG. 14A) LSALT peptide attenuates the levels of a number of different serum cytokines.

6-8 weeks old SCID mice were given an intraperitoneal injection of LPS (0.5 mg/kg) 5 minutes prior to intravenous injection of LSALT peptide or a control peptide. 4 hours following injection of LPS, blood was collected by cardiac puncture and changes in plasma cytokine levels were assessed using Luminex Cytokine Arrays. Bar graphs show the level of the anti-inflammatory cytokine IL-10 released in the plasma in LSALT peptide or control peptide in two independent experiments. (FIG. 14H and FIG. 14I) LSALT peptide increases the production of the anti-inflammatory mediator IL-10 in response to LPS.

Example 15

Figure 24A:
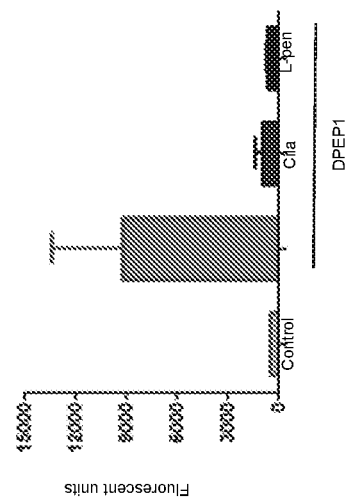
FIG. 24A provides a graph showing quantification of human melanoma cells (70 W) to DPEP1 transfected COS-1 cells. Cos-1 cells were transiently transfected with human DPEP1 using Lipofectamine 2000. GFP expressing 70 W human melanoma cells were seeded on the top of DPEP1 expressing Cos-1 cell monolayer for 4 hours. Cells were then washed and fixed. 70 W melanoma cells adhered to the DPEP1 expressing Cos-1 cell monolayer were counted under 10× magnification using fluorescence microscope. Values shown are from three independent experiments; asterisks (***) indicate P<0.001 as compared with mock transfected cells.

70 W Human Melanoma Cells Bind to DPEP-1 Expressing COS-1 Monolayer in Vitro Cos-1 cells were transfected with 3 µg of human DPEP-1 cDNA. Transfected cells were reseeded 24 hours after on 12 or 24 well places. 48 hours later, 70 W melanoma cells expressing stable GFP-luciferase were harvested using Puck's EDTA and 10×103 cells were seeded on top of the DPEP-1 expressing Cos-1 monolayer. Cells were incubated for 4 hours at 37 C. After incubation cells were vigorously washed two times with PBS. Cells were then fixed using paraformaldehyde (4%). The number 70 W melanoma cells bound/adhered were counted under 10× magnification over 10 different field of views using an inverted fluorescence microscope (FIG. 24A). A unpaired 2-tailed Student's t-test was performed to compare the (FIG. 24A). A unpaired 2-tailed Student's t-test was performed to compare the binding of 70 W melanoma cells to DPEP-1 transfected cells against the control of mock transfected cells. Values shown are from three independent experiments; asterisks (***) indicate P<0.001 as compared with mock transfected cells.

Figure 24B:
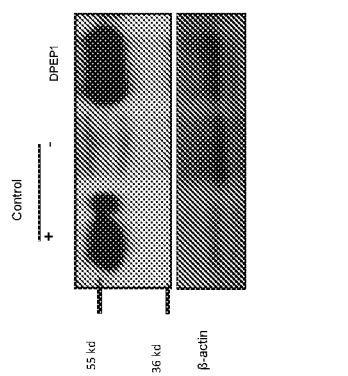
FIG. 24B provides an image of an immunoblot that confirms expression of DPEP1 in transfected COS-1 cells with positive control (DPEP1) for comparison.
Figure 24C:
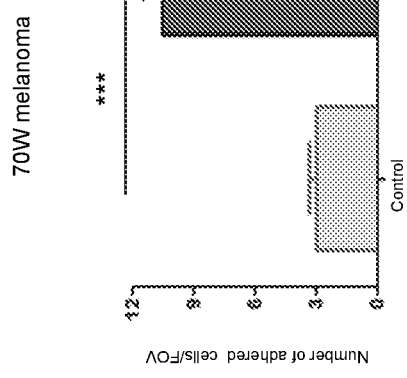
FIG. 24C provides a graph showing quantification of DPEP1 enzymatic activity of transfected COS-1 cells. A fluorometric assay specific for DPEP1 enzyme activity was performed (according to Heywood and Hooper, 1995) as described before. DPEP1 activity confirms the enzymatic activity of human DPEP1 proteins and Cilastatin (Cila) and Penicillamine (L-Pen) inhibited the activity.

Proteins from DPEP-1 transfected cells were isolated after 48 hours using octyl-glucoside/RIPA lysis buffer and western blot analysis was performed to assess DPEP-1 expression using a DPEP-1 specific antibody (Proteintech) (FIG. 24B). Membrane dipeptidase activity assay and the fluorometric detection of D-Phe was performed exactly as described by Heywood and Hooper (1995) (FIG. 24C).

Example 16

LSALT Alanine Substitution Synthetic Peptide Binding to Transfected HEK 293 Cells In the case of known bioactive peptides, rational design of peptide ligands with favorable therapeutic properties can be completed. In such an approach, one makes stepwise changes to a peptide sequence and determines the effect of the substitution upon bioactivity or a predictive biophysical property of the peptide (e.g., solution structure). Hereinafter, these techniques are collectively referred to as "rational design." In one such technique, one makes a series of peptides in which one replaces a single residue at a time with alanine This technique is commonly referred to as an "alanine walk" or an "alanine scan." When two residues (contiguous or spaced apart) are replaced, it is referred to as a "double alanine walk." The resultant amino acid substitutions can be used alone or in combination to result in a new peptide entity with favorable therapeutic properties.

HEK 29 cells were transfected with DPEP1 or DPEP2, two days prior to assay and were plated onto collagen-coated coverslips one day prior. Then fixed 10 min with 3.7% formaldehyde in PBS, washed 3 times in PBS, incubated with Alanine-substituted test peptide at 5 uM each, 1 hr at room temperature, washed twice with PBS gently, incubated with 1/50 Alexa 568-straptavadin in PBS, 1 hr at room temperature, washed twice with PBS gently and added DAPI Mounted with DAKO Fluorescent mounting media and evaluated for binding under fluorescence microscope.

TABLE 1

Binding Activity and Sequences of Alanine Walk

| Peptide Reference | Sequence | SEQ ID NO: |
|---|---|---|
| LSALT | LSALTPSPSWLKYKAL | 1 |
| Pos 1 | ASALTPSPSWLKYKAL | 15 |
| Pos 2 | LAALTPSPSWLKYKAL | 16 |
| Pos 3 | LSAATPSPSWLKYKAL | 17 |
| Pos 4 | LSAATPSPSWLKYKAL | 18 |
| Pos 5 | LSALAPSPSWLKYKAL | 19 |
| Pos 6 | LSALTASPSWLKYKAL | 20 |
| Pos 7 | LSALTPAPSWLKYKAL | 21 |
| Pos 8 | LSALTPSASWLKYKAL | 22 |
| Pos 9 | LSALTPSPAWLKYKAL | 23 |
| Pos 10 | LSALTPSPSALKYKAL | 24 |
| Pos 11 | LSALTPSPSWAKYKAL | 25 |
| Pos 12 | LSALTPSPSWLAYKAL | 26 |
| Pos 13 | LSALTPSPSWLKAKAL | 27 |
| Pos 14 | LSALTPSPSWLKYAAL | 28 |
| Pos 15 | LSALTPSPSWLKYKAL | 29 |
| Pos 16 | LSALTPSPSWLKYKAA | 30 |

Example 17

Circular Dichroism Analysis of LSALT Peptide

The physical and chemical properties of protein therapeutics are critical factors that influence the ease of manufacturing, development and clinical use. The LSALT peptide was evaluated in terms of its solubility, aggregation state and stability using a variety of biophysical methods. The secondary structure of the protein was determined by circular dichroism (CD) spectroscopy: the far-UV spectrum of LSALT in aqueous buffer shows the minima at 222 nm characteristic of a α-helical conformation A CD (circular dichroism) analysis was performed on the LSALT peptide and the various analogs, demonstrating a propensity for the peptide to form an alpha-Helix.

| Reference | Sequence | MW | SEQ ID NO: |
|---|---|---|---|
| Native: | LSALTPSPSWLKYKAL | MW = 1775.12 | 1 |
| Bio-Native: | Bio-LSALTPSPSWLKYKAL | MW = 2001.43 | 31 |
| #A1 | Bio-ASALTPSPSWLKYKAL | MW = 1959.40 | 32 |
| #A2 | Bio-LAALTPSPSWLKYKAL | MW = 1985.40 | 33 |
| #A3 | Bio-LSGLTPSPSWLKYKAL | MW = 1987.40 | 34 |
| #A4 | Bio-LSAATPSPSWLKYKAL | MW = 1959.40 | 35 |

-continued

| Reference | Sequence | MW | SEQ ID NO: |
|---|---|---|---|
| #A5 | Bio-LSALAPSPSWLKYKAL | MW = 1971.40 | 36 |
| #A6 | Bio-LSALTGSPSWLKYKAL | MW = 1961.40 | 37 |
| #A7 | Bio-LSALTPAPSWLKYKAL | MW = 1985.43 | 38 |
| #A8 | Bio-LSALTPSASWLKYKAL | MW = 1961.37 | 39 |
| #A9 | Bio-LSALTPSPAWLKYKAL | MW = 1985.40 | 40 |
| #A10 | Bio-LSALTPSPSALKYKAL | MW = 1886.30 | 41 |
| #A11 | Bio-LSALTPSPSWAKYKAL | MW = 1959.30 | 42 |
| #A12 | Bio-LSALTPSPSWLAYKAL | MW = 1944.30 | 43 |
| #A13 | Bio-LSALTPSPSWLKAKAL | MW = 1909.33 | 44 |
| #A14 | Bio-LSALTPSPSWLKYAAL | MW = 1944.34 | 45 |
| #A15 | Bio-LSALTPSPSWLKYKGL | MW = 1987.40 | 46 |
| #A16 | Bio-LSALTPSPSWLKYKAA | MW = 1959.40 | 47 |
| #A17 | Ac-LSALTPSPSWLKYKAL | MW = 1817.16 | 48 |
| #A18 | Ac-LSALTPSPSWLKYKAL-amide | MW = 1816.15 | 49 |
| #A19 | Bio-LSALTPSPSWLKYKAL-amide | MW = 2000.40 | 50 |

Notably, positions 1, 5, 10 and 12 (these mutants displayed decreased and increased binding to DPEP-1 by immunofluorescence) all cluster on the same face as a putative alpha-helical LSALT and would constitute a contiguous cluster on one side of the helix and argues that those residues would interact with DPEP-1.

In circular dichroism spectroscopy the ellipticity value at 222 nm is a measure of a-helical content. 50% trifluoroethanol is a hydrophobic solvent and induces α-helical structure if the structure can be induced. All of the peptides tested can be induced to adopt α-helical structure. The peptides are random coils in benign conditions (non-denaturing). The buffer conditions were aqueous phosphate, pH 7.0. The native peptide has a free α-amino group and blocking this group with a biotin is a definite advantage for inducible α-helical structure (compare native vs biotin-native).

Similarly having a C-terminal amide group is advantageous for inducible α-helical structure (compare peptides A16/A17 with A18/A19 where % inducible helical structure is ~32% vs 51%). Comparing A1 vs A2 shows that substituting a Ser residue with a Ala residue significantly enhances inducible α-helical structure as expected (A1a is a strong helical forming residue compared to Ser) (J. Peptide Science, 1, 319-329 (1995) for α-helical propensity scale).

| | [θ] Comparison (222 nm) | | | |
|---|---|---|---|---|
| Name | Benign (No TFE) | 50% TFE | Inducible Helical Structure (50% TFE-benign) | % Inducible Helical Structure (Inducible/50% TFE) |
| Native | −48373 | −72298 | 23,925 | 33.1% |
| Biotin- | −47013 | −90148 | 43,134 | 47.8% |

-continued

| | [θ] Comparison (222 nm) | | | |
|---|---|---|---|---|
| Name | Benign (No TFE) | 50% TFE | Inducible Helical Structure (50% TFE-benign) | % Inducible Helical Structure (Inducible/50% TFE) |
| Native | | | | |
| A1 | −82054 | −119807 | 37,752 | 31.5% |
| A2 | −66128 | −117502 | 51,374 | 43.7% |
| A3 | −49714 | −68580 | 18,865 | 27.5% |
| A4 | −60519 | −76916 | 16,397 | 21.3% |
| A5 | −49443 | −79198 | 29,755 | 37.6% |
| A6 | −42491 | −70926 | 28,435 | 40.1% |
| A7 | −49209 | −70198 | 20,988 | 29.9% |
| A8 | −32890 | −42335 | 9,444 | 22.3% |
| A9 | −49453 | −62889 | 13,436 | 21.4% |
| A10 | −26209 | −35792 | 9,583 | 26.8% |
| A11 | −58514 | −80196 | 21,682 | 27.0% |
| A12 | −28292 | −36742 | 8,451 | 23.0% |
| A13 | −49352 | −80841 | 31,488 | 39.0% |
| A14 | −25794 | −39862 | 14,068 | 35.3% |
| A15 | −68717 | −92167 | 23,450 | 25.4% |
| A16 | −25275 | −37070 | 11,796 | 31.8% |
| A17 | −57282 | −74897 | 17,615 | 23.5% |
| A18 | −38340 | −78951 | 40,612 | 51.4% |
| A19 | −75952 | −153947 | 77,996 | 50.7% |

50% TFE is considered 100% Folded for Each Analogue
Benign buffer (100 mM KCl, 50 mM Na$_2$HPO$_4$/NaH$_2$PO$_4$, pH 7.0)

Example 18

Glycine Spacers Enhance Binding of LSALT to DPEP1

Figures 15A, 15B:
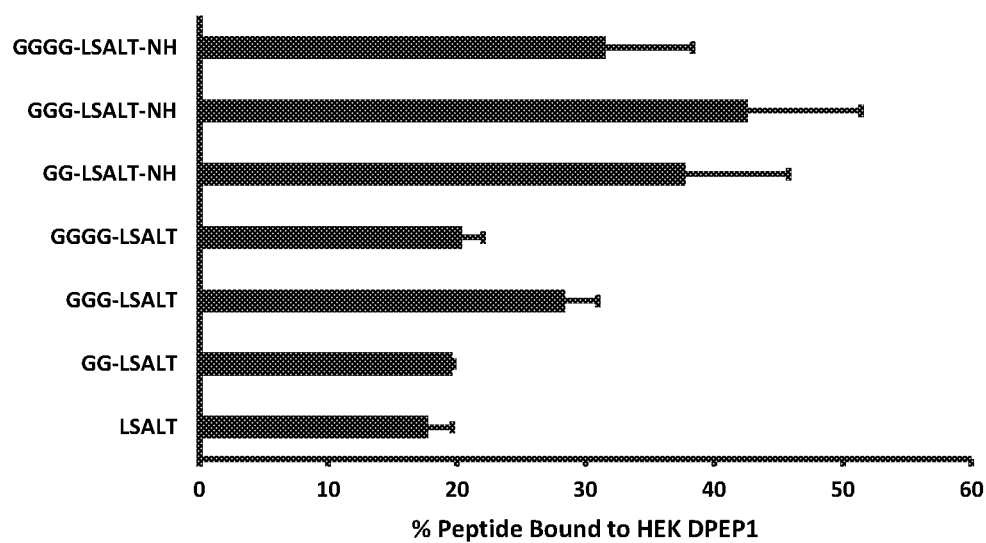
FIGS. 15A-C provides a table and graph showing glycine spacers enhance binding of LSALT to DPEP1. HEK cells stably overexpressing human DPEP1 or human tubular epithelial cells (hTEC) were incubated with biotinylated LSALT peptides (50 μM) with various modifications (glycine linkers and/or amidation) for 1 hour. Peptide was detected via secondary streptavidin fluorescent antibody. Peptide binding was assessed and quantified via flow cytometry. Percentage of peptide binding was compared relative to the negative control. (n=3/group)
Figure 15C:
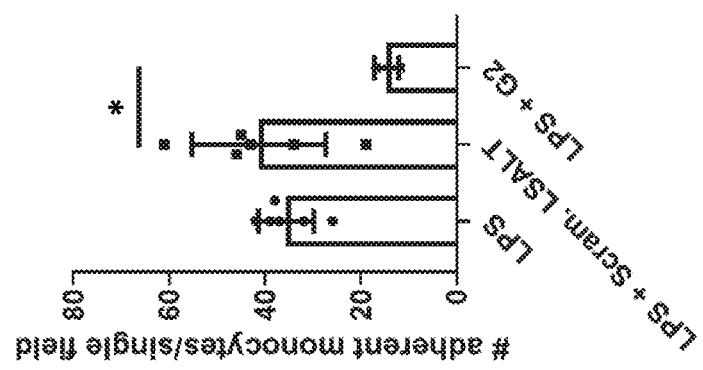

HEK293T cells were transfected with pcDNA vector containing human DPEP1 via Lipofectamine 2000 as per manufacturer protocol. Transfected cells were positively selected for using geneticin resistance and subcloned to generate stably transfected DPEP1 clones. Human renal tubular epithelial cells (hTEC) were isolated and cultured from human kidney nephrectomies. For immunocytochemistry, cells were cultured on collagen coated glass coverslips and fixed by 4% paraformaldehyde. Fixed cells were incubated with biotinylated LSALT peptides (50 µM) with various modifications (glycine linkers and/or amidation) for 1 hour at 37° C. before PBS washes. Bound biotinylated peptide was detected via secondary streptavidin fluorescent conjugate (30 min. incubation at 37° C.) and washed with PBS. FIG. 15A shows that binding of LSALT with glycine linker and amidation modifications was assessed and quantified via flow cytometry. Stably transfected DPEP1 HEK cells were resuspended and incubated with biotinylated peptide (50 µM) for 1 hour at 37° C. before PBS washes. Bound biotinylated peptide was detected via secondary streptavidin fluorescent conjugate (30 min. incubation at 37° C.) and washed with PBS. Peptide binding was analyzed via flow cytometer. Percentage of peptide binding was compared relative to the negative control. (n=3/group). FIG. 15C shows functional inhibition of inflammation by glycine-linked LSALT was tested in a model of endotoxemia induced acute kidney injury. LysM$^{(gfp)}$ mice were subjected to endotoxemia via intravenous injection of lipopolysaccharide (LPS, O111:B4) at a dose of 5 mg/kg. The kidney was imaged using multiphoton microscopy at 4 hours post-injection. Tri-glycine linked LSALT (G2) was used intravenously to pretreat mice 10 min. before LPS injection. Inflammation was quantified by manual counting of monocyte adhesion in single microscopy fields (n=3-6 fields/group; *:p=0.02).

Example 19

Alanine Substitutions in LSALT Affect Binding Affinity

Figure 16B:
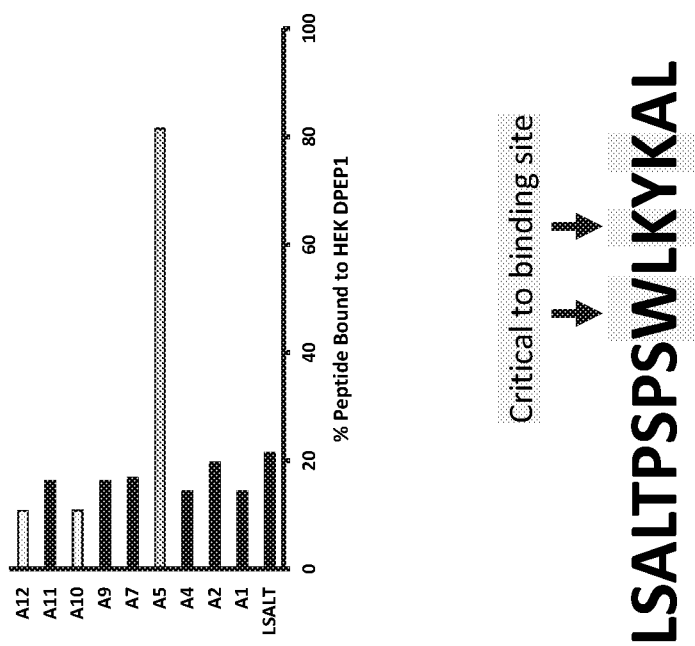
FIG. 16B quantifies binding of modified LSALT with alanine substitutions to DPEP1 expressing cells. HEK cells stably overexpressing human DPEP1 were incubated with biotinylated modified LSALT peptides (50 μM) for 1 hour. Peptide binding was assessed and quantified via flow cytometry. Percentage of peptide binding was compared relative to negative control.

FIG. 16A shows LSALT was modified at each amino acid position with an alanine substitution to determine which amino acid residues affect binding to DPEP1. FIG. 16B shows HEK293T cells were transfected with pcDNA vector containing human DPEP1 via Lipofectamine 2000 as per manufacturer protocol. Transfected cells were positively selected for using geneticin resistance and subcloned to generate stably transfected DPEP1 clones. Stably transfected DPEP1 HEK cells were resuspended and incubated with biotinylated peptide (50 µM) for 1 hour at 37° C. before PBS washes. Bound biotinylated peptide was detected via secondary streptavidin fluorescent conjugate (30 min. incubation at 37° C.) and washed with PBS. Peptide binding was analyzed via flow cytometer. Percentage of peptide binding was compared relative to negative control. Decreased peptide binding indicated a potential critical amino acid residue for LSALT-DPEP1 binding interactions.

Example 21

LSALT Fragments Metabolized in Blood can Still Bind to DPEP1

Figure 17B:
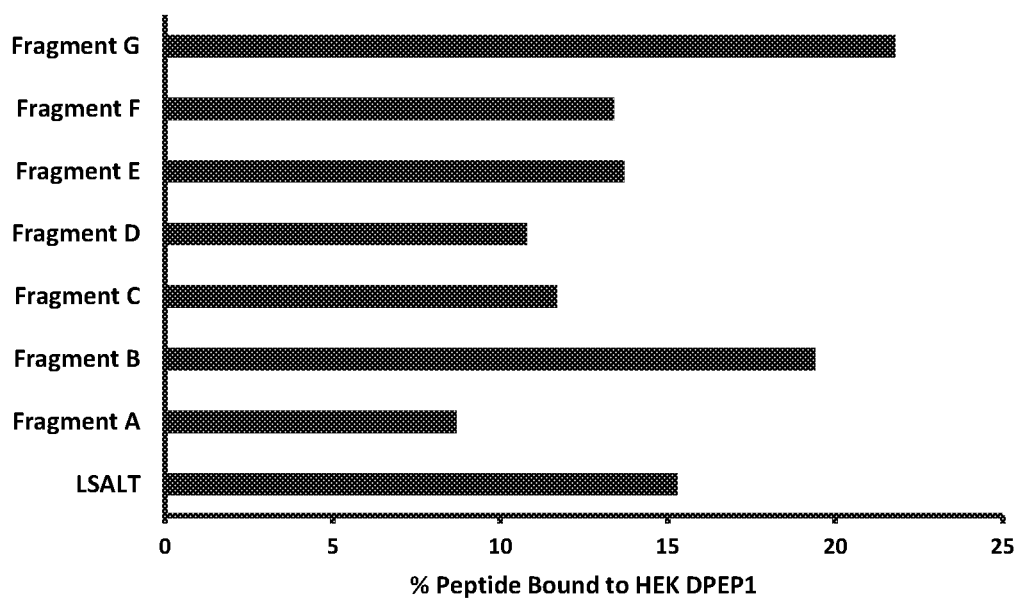
FIG. 17B quantifies binding of LSALT fragments to DPEP1 expressing cells. LSALT fragment binding was assessed and quantified via flow cytometry. Percentage of peptide binding was compared relative to the negative control.
Figure 17C:
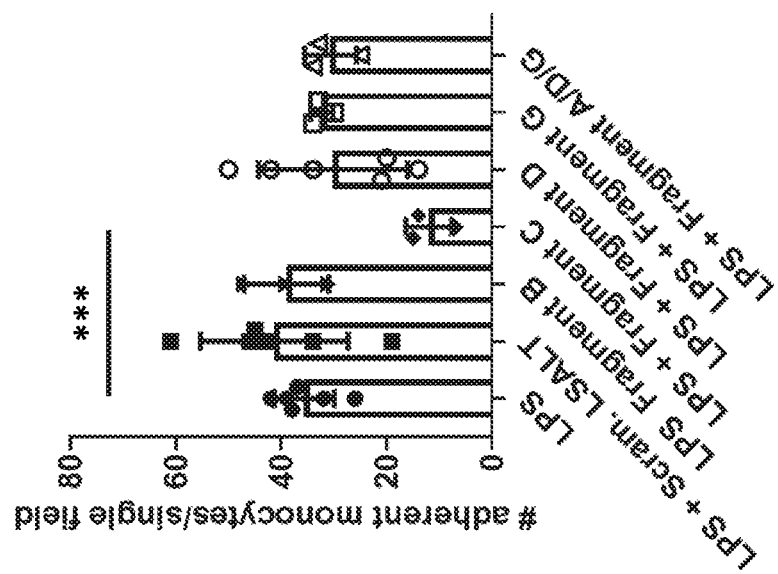
FIG. 17C provides a graph that demonstrates metabolized LSALT fragments can inhibit endotoxemia induced kidney inflammation. Inflammation in the kidney was induced by intravenous injection of LPS (O111:B4, 5 mg/kg) into volume depleted LysM$^{gfp/gfp}$ mice. Mice were pretreated with either control peptide (Scram. LSALT) or various LSALT fragments (labels correspond to FIG. 17A) 5 min. prior to LPS treatment. Kidneys were assessed for inflammation 4 hours post LPS treatment. Inflammation was quantified by manual counting of monocyte adhesion in single microscopy fields (n=3-6 fields/group; ***:p=0.004).

FIG. 17A shows LSALT peptide (50 µg/mL) was incubated in whole human blood (citrate or K2EDTA treated) for various timepoints up to 120 min. Plasma was separated for each sample and phosphoric acid added to stabilize peptide at each timepoint. Samples were assessed for LSALT and its' metabolites using LC/MS. LSALT metabolites were identified using PEAKS X and database searches against LSALT and the human proteome. FIG. 17B shows HEK293T cells were transfected with pcDNA vector containing human DPEP1 via Lipofectamine 2000 as per manufacturer protocol. Transfected cells were positively selected for using geneticin resistance and subcloned to generate stably transfected DPEP1 clones. Stably transfected DPEP1 HEK cells were resuspended and incubated with biotinylated LSALT fragment peptides (50 µM) for 1 hour at 37° C. before PBS washes. Bound biotinylated peptide was detected via secondary streptavidin fluorescent conjugate (30 min. incubation at 37° C.) and washed with PBS. Peptide binding was analyzed via flow cytometer. Percentage of peptide binding was compared relative to negative control. FIG. 17C shows functional inhibition of inflammation by LSALT fragments (refer to FIG. 17A) was tested in a model of endotoxemia induced acute kidney injury. LysM$^{(gfp)}$ mice were subjected to endotoxemia via intravenous injection of lipopolysaccharide (LPS, O111:B4) at a dose of 5 mg/kg. The kidney was imaged using multiphoton microscopy at 4 hours post-injection. Various LSALT fragments was used intravenously to pretreat mice 10 min. before LPS injection. Inflammation was quantified by manual counting of monocyte adhesion in single microscopy fields (LPS vs. Fragment C; n=3-6 fields/group; ***:p=0.004).

Figure 18A:
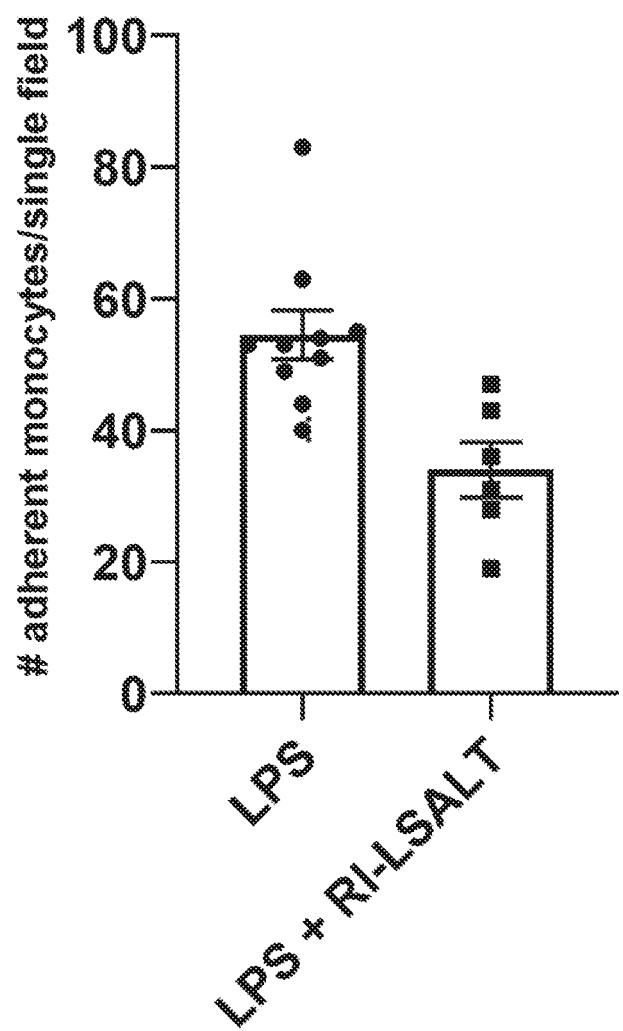
FIG. 18A shows retroinverso (RI) D-amino acid LSALT peptide can inhibit endotoxemia induced kidney inflammation. Inflammation in the kidney was induced by intravenous injection of LPS (O111:B4, 5mg/kg) into volume depleted LysM$^{(gfp/gfp)}$ mice. Mice were pretreated with retro inverso LSALT (RI LSALT) 5 min. prior to LPS treatment. Kidneys were assessed for inflammation 4 hours post LPS treatment. Inflammation was quantified by manual counting of monocyte adhesion in single microscopy fields (n=6-10 fields/group; **:p=0.0034).

FIG. 18A shows modified LSALT can inhibit endotoxemia induced kidney inflammation. Inflammation in the kidney was induced by intravenous injection of LPS (O111:B4, 5mg/kg) into volume depleted LysM$^{(gfp)}$ mice. The kidney was imaged using multiphoton microscopy at 4 hours post-injection. Mice were pre-treated with retro-inverso LSALT (RI LSALT) 10 min. prior to LPS treatment. Kidneys were assessed for inflammation 4 hours post LPS treatment. Inflammation was quantified by manual counting of monocyte adhesion in single fields (n=6 10 fields/group; **:p=0.0034).

Example 22

Novel DPEP-1 Binding Peptides

In FIG. 19A, human recombinant DPEP1 (Creative Biomart; DPEP1-77H, amino 6×His tagged) was linked to agarose beads (Thermo HisPur Ni-NTA Resin;88221— mixed 15 uL of Ni-NTA resin with 15 ug DPEP1, total volume of 30 uL of PBS, blocked for 1 hr in 5%BSA/PBS before use), and used to biopan for phage-displayed peptide sequences (New England Biolabs Ph.D.-12 Phage Display Library; E8110S). The Ph.D.-12 library was first subtracted 3× against DPEP2 (Creative Biomart; DPEP2-8611H) linked to agarose beads (10 uL of DPEP-agarose in 100 uL Luria broth and $4.5 \times 10^9$ pfu of Ph.D.-12 library), wherein the phage remaining in the supernatant was retained, and those that stuck to the subtraction beads were discarded. Second, the library was selected against DPEP1-agarose beads, wherein the phage remaining in the supernatant were discarded and those binding to DPEP1-agarose pellet were retained. The pellet was washed 3× in PBS, then transferred to phage host bacterial culture (ER 2738) to amplify the bound phage, which were then precipitated as per manufacturer's protocol. The recovered phage were then used to repeat the subtraction and selection steps. The final selected library was plated on a bacterial lawn to allow selection of individual blue plaques; each plaque is formed from the clonal amplification of an individual phage particle thus containing a single, unique displayed peptide. Each plaque was amplified separately in liquid bacterial host culture. The DNA from each clonal culture was recovered using the Omega Bio-tek E.Z.N.A. M13 DNA Mini Kit and sent for sequencing of the region containing the insert corresponding to the displayed peptide. DNA inserts were translated to the expected protein and sorted to assess the number of repeating sequences. Those appearing to be specific were searched on the NIH BLAST database to find possible matching identities, with surface proteins being preferentially selected.

Figure 19B:
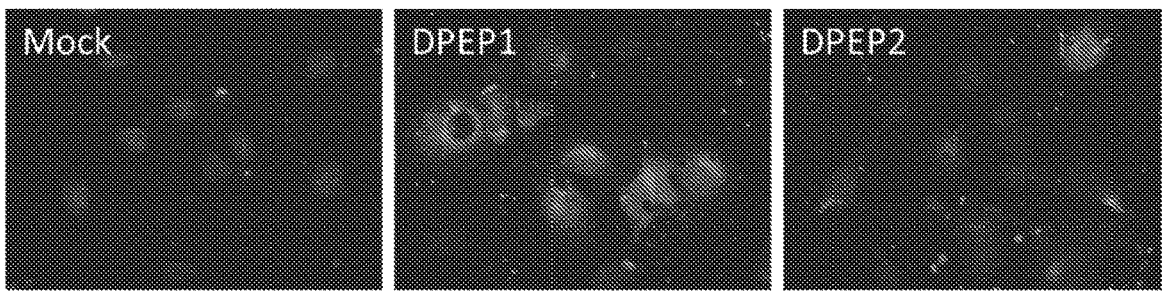
Figure 19B:
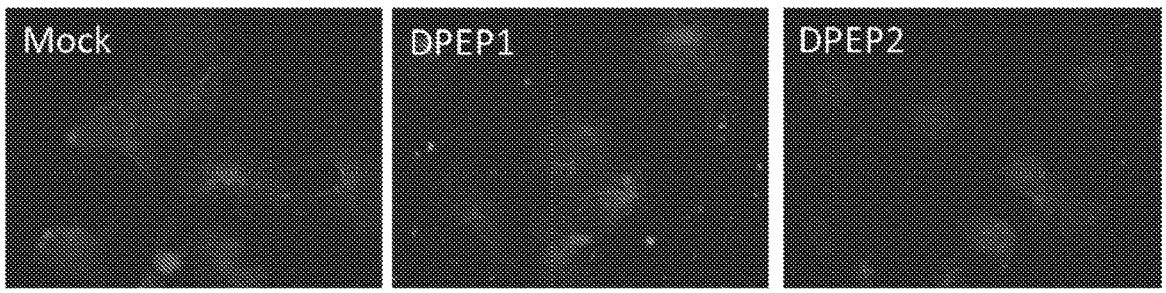
Figure 19B:
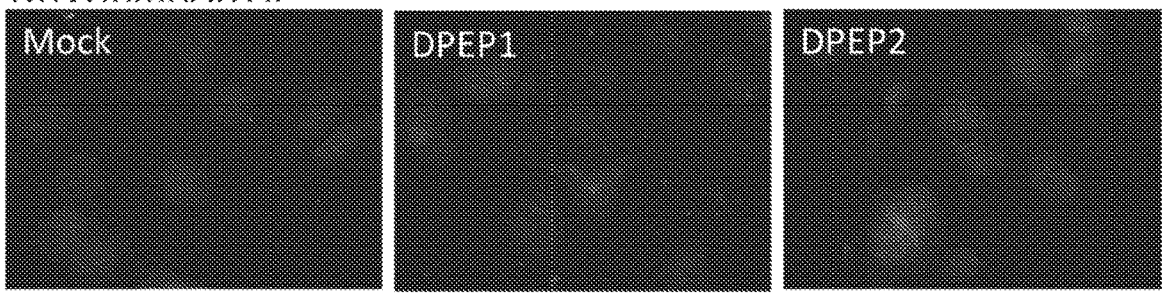
Figure 19B:
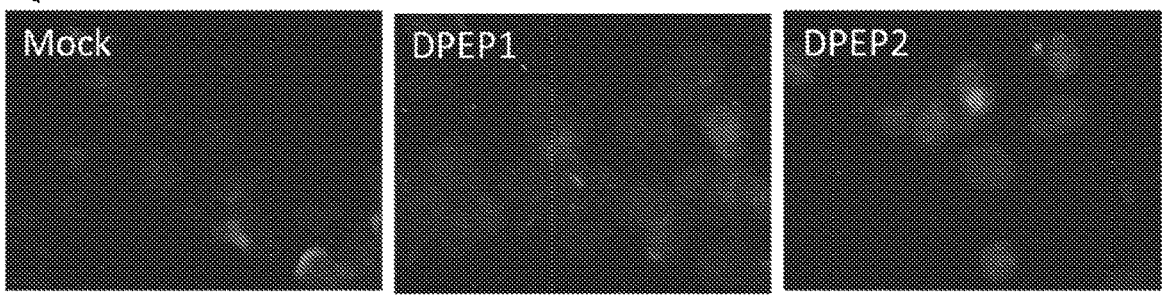
Figure 19B:

In FIG. 19B, Cos1 cells were transiently transfected with plasmids corresponding to human DPEP1 or DPEP2 (Lipofectamine 2000) 24 hrs prior to plating on collagen-coated (PureCol; Type I collagen from bovine tendon) coverslips. One day later cells were incubated with $10^8$ pfu test phage, which were then detected by anti-M13 rabbit serum (in house) with anti-rabbit Alexa 568 secondary. After fixing and counterstaining with DAPI, coverslips were fluorescently imaged. As the phage peptide tentatively identified as corresponding to Neogenin had the best binding, its corresponding peptide insert was made synthetically.

Figure 19C:
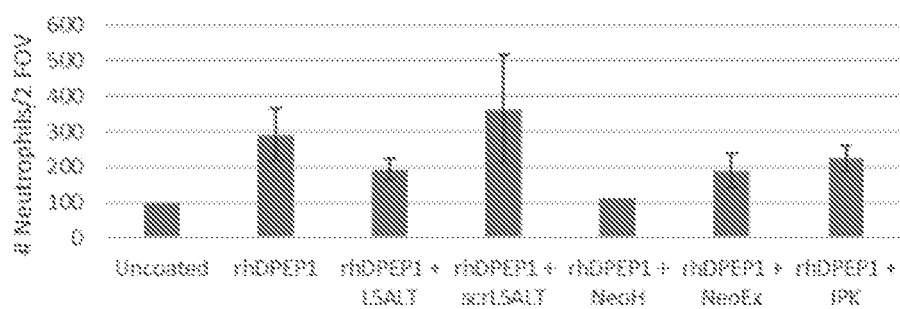
Figure 19C:
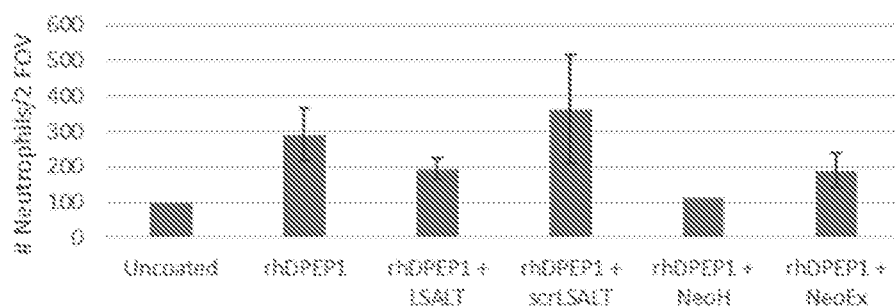
Figure 19C:
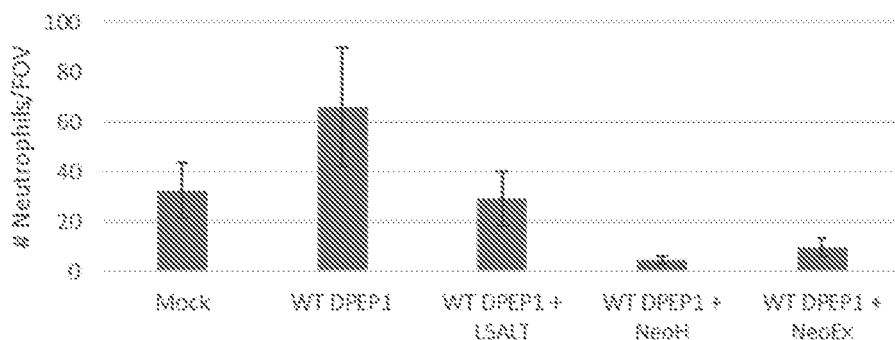

FIG. 19C demonstrates that inhibition of neogenin-mimetic peptide prevents neutrophil adhesion DPEP1. In the top panel, 96-well nickel-coated plates were coated with nothing or his-tagged recombinant human DPEP1 (9 pmol/well in PBS, incubated for 1 hr at room temp), washed out 3× with PBS +0.05% Tween 20, and blocked for 1 hr at room temp with cell culture media (Cell Applications Inc. Cat#111-500). Freshly isolated human neutrophils were added to the wells at 5×104/mL, 100 uL volume, with the indicated peptides at 0.45uM. After 30 minutes at 37° C., wells were washed out 3× with PBS, and fixed with 3.7% formaldehyde in PBS. Two fields-of-view were photographed at 4× magnification and all the cells counted were recorded for each well, done in triplicate. In the middle panel, Cos1 cells were transfected with an empty vector (Mock) or a vector encoding wild type human DPEP1, two days prior. One day prior, transfected cells were plated at near confluency in a 24-well plate. On the day of the experiment, freshly isolated human neutrophils were added to the wells at 1×105/mL, 0.5mL volume, with the indicated peptides at 100 uM. After 30 minutes at 37° C., wells were washed out 3× with culture media, then fixed in 3.7% formaldehyde in PBS. Five fields-of-view were photographed at 20× magnification and averaged for each well, done in triplicate. In the bottom panel, two days prior, 24-well plates were coated with Attachment Factor Solution (Cell Applications Inc. Cat#123-500). One day prior, Human Lung Microvascular Endothelial Cells (HLMVECs, Cell Applications Inc. Cat# 540-05a) were plated at near confluency. On the day of the experiment, HLMVECs were stimulated for 4 hrs with nothing or LPS at 1 ug/mL. Freshly isolated human neutrophils were added to the wells at $1 \times 10^5$/mL, 0.5 mL volume, with the indicated peptides at 100 uM, or neogenin blocking antibody (RnD Cat# AF1079) at 13 ug/mL. After 30 minutes at 37° C., wells were washed out 3× with culture media, then fixed in 3.7% formaldehyde in PBS. Five fields-of-view were photographed at 20× magnification and averaged for each well, done in triplicate. Each dot graphed equals the mean of three technical replicates.

Example 23

Identification of Sequences that Bind to LSALT

Figure 20E:
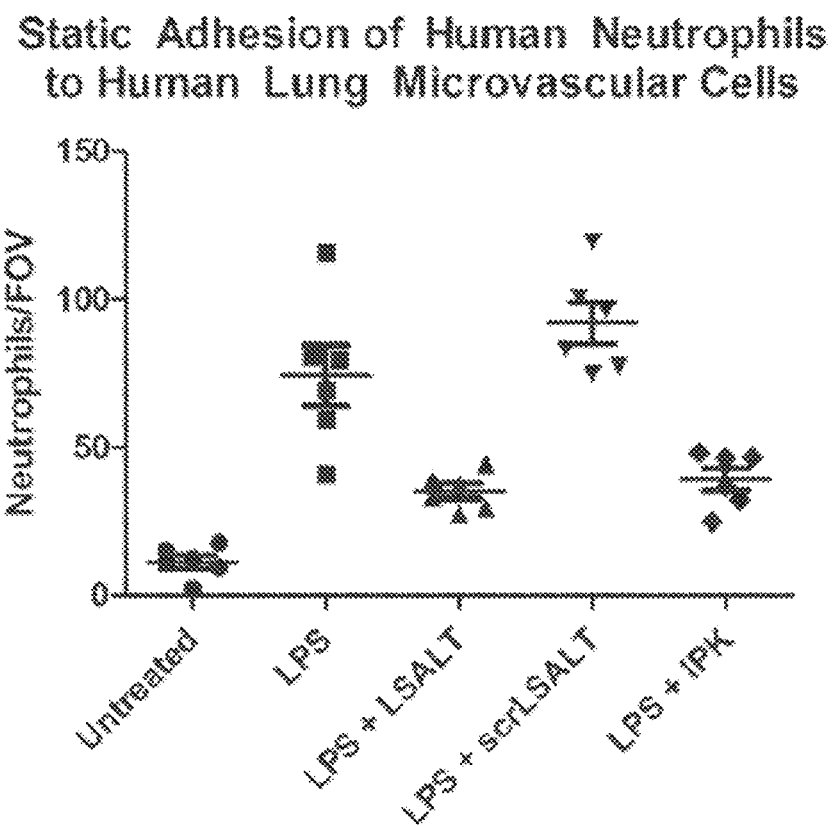

FIG. 20A shows peptide sequences from phage display biopanning against LSALT peptide. Synthetic LSALT peptide was covalently linked to NHS Activated Agarose (Thermo Cat#26196) according to manufacturer's instructions. 50 uL of LSALT-Agarose was added to 1 mL PBS with 2.25 x1010 pfu of Ph.D.-12 Phage library and incubated on a rotator for 1 hr at 4° C. Agarose beads were washed 3× with PBS and bound phage were recovered by overnight culture with bacterial host and subjected to two more rounds of selection against LSALT-Agarose. The final selected library was plated on a bacterial lawn to allow selection of individual blue plaques; each plaque is formed from the clonal amplification of an individual phage particle thus containing a single, unique displayed peptide. Each plaque was amplified separately in liquid bacterial host culture. The DNA from each clonal culture was recovered using the Omega Bio-tek E.Z.N.A. M13 DNA Mini Kit and sent for sequencing of the region containing the insert corresponding to the displayed peptide. DNA inserts were translated to the expected protein and sorted to assess the number of repeating sequences. Two peptides were identified containing the motif IPKXPXXXP. One of the IPK phage hits (HIPKSPIQIPII) was able to inhibit neutrophil adhesion in LPS-stimulated human endothelial cells (FIG. 20E). The IPK motif may represent the neutrophil-side receptor that interacts with DPEP1.

FIGS. 20B-D shows alignment comparisons of the protein sequences of human DPEP1, DPEP2, and DPEP3, as obtained from the NIH database. Coding exons are indicated, and the IPK sequence was found only in Exon 2 of DPEP1. Taking into consideration that IPK was found in the phage biopanning against the LSALT peptide, this suggests that LSALT binds at least preferentially to exon 2 of DPEP1.

FIG. 20E shows that IPK peptide inhibits neutrophil adhesion to LPS activated endothelial cells. Two days prior to the experiment, 24-well plates were coated with Attachment Factor Solution (Cell Applications Inc. Cat#123-500). One day prior, Human Lung Microvascular Endothelial Cells (HLMVECs, Cell Applications Inc. Cat# 540-05a) were plated at near confluency. On the day of the experiment, HLMVECs were stimulated for 4 hrs with nothing or LPS at 1 ug/mL. Freshly isolated human neutrophils were added to the wells at $1\times10^5$/mL, 0.5mL volume, with the indicated peptides at 100 uM. After 30 minutes at 37° C., wells were washed out 3× with culture media, then fixed in 3.7% formaldehyde in PBS. Five fields-of-view were photographed at 20× magnification and averaged for each well, done in triplicate. Each dot graphed equals the mean of three technical replicates.

Example 24

Metastatic Cancer Cells Bind to DPEP1-Expressing COS1 Monolayers in Vitro

Figure 21A:
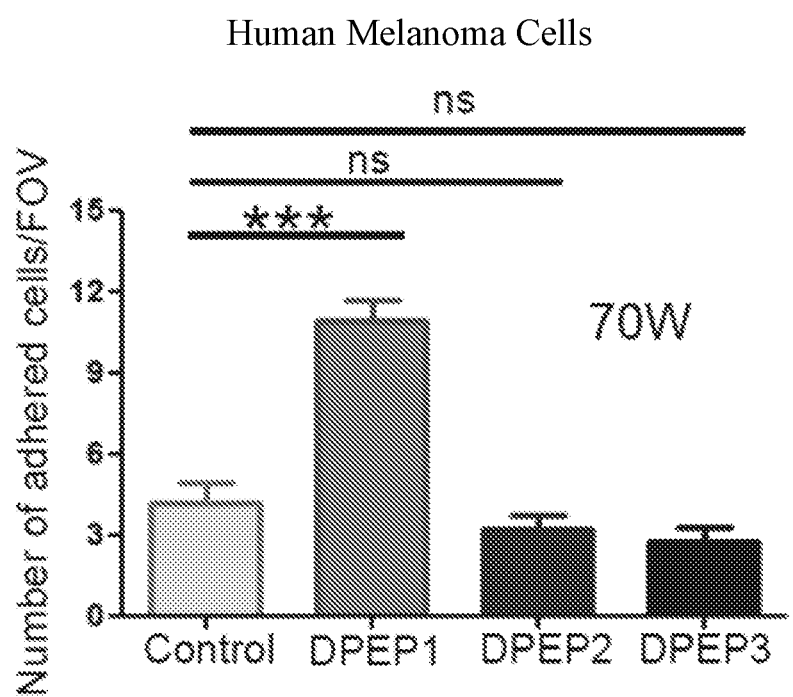
FIGS. 21A-C demonstrates that LSALT decreases binding of metastatic cancer cells to DPEP1-expressing COS1 monolayers in vitro.
Figure 21B:
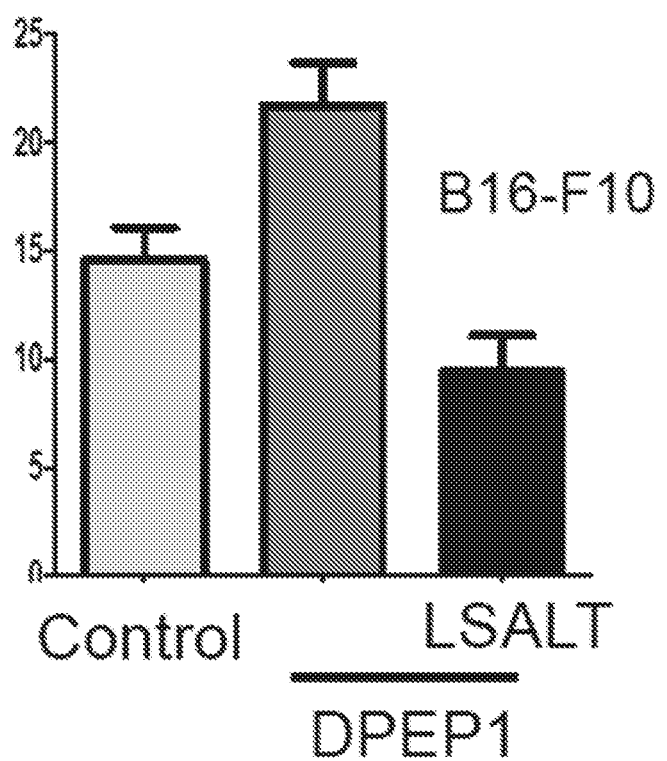
Figure 21C:
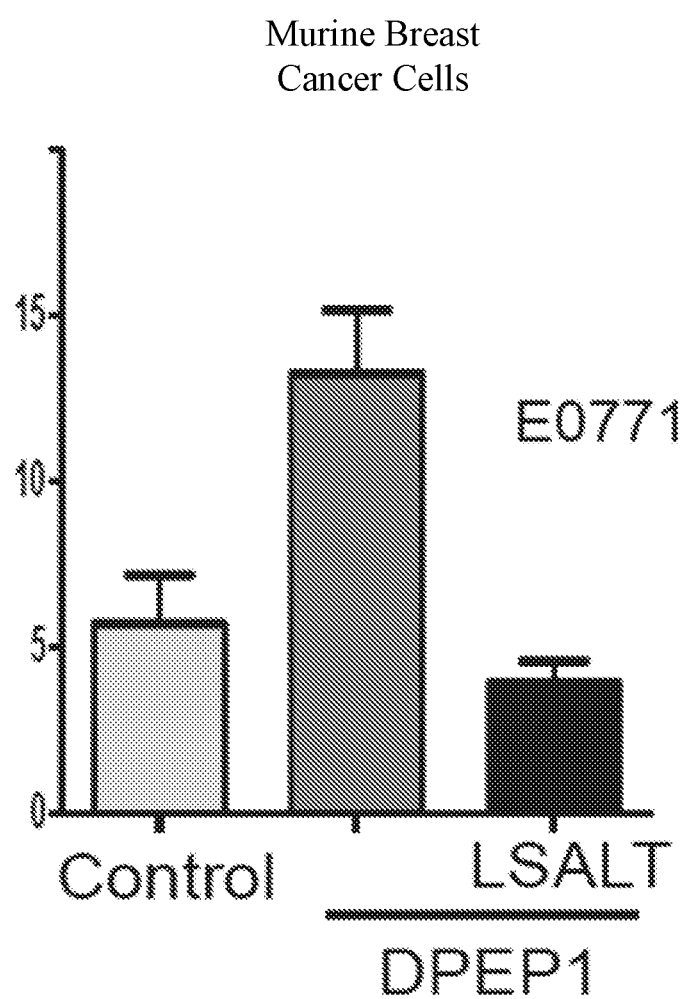

LSALT decreases binding of metastatic cancer cells to DPEP1-expressing COS1 monolayers in vitro. FIG. 21A shows quantification of human melanoma 70 W that bind to COS1 (control), DPEP1, DPEP2, or DPEP3 transfected COS1 cells. FIGS. 21B-C show quantification of murine melanoma B16-F10 (B) or murine breast cancer E0771.LMB (C) cells that bind to COS1 (control) or DPEP1 COS1 in the absence or presence of LSALT (50 µM).

Example 25

Figure 22A:
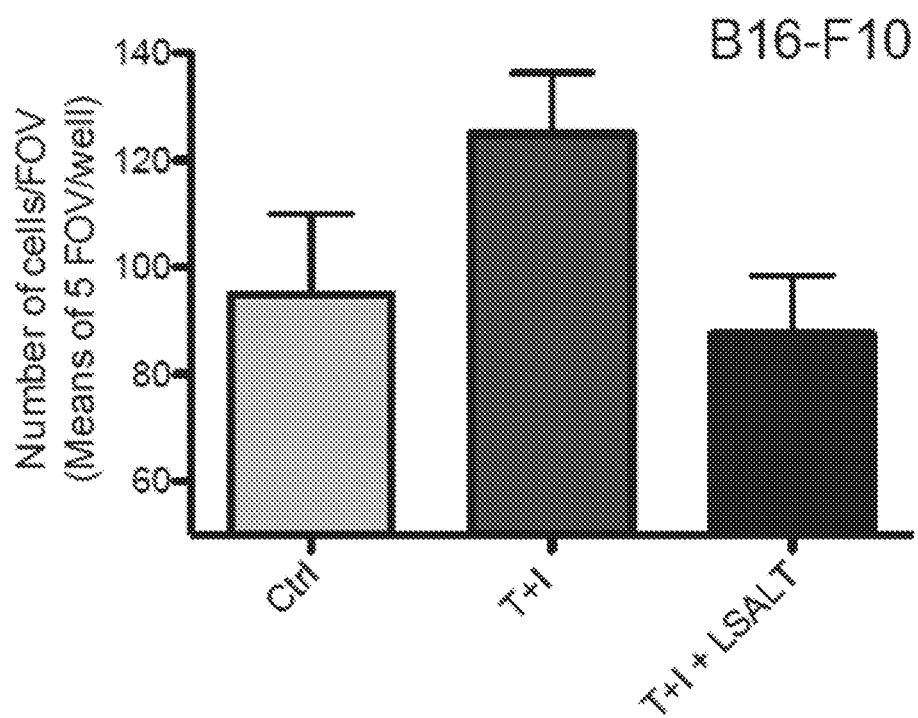
FIGS. 22 A-B provides graphs showing LSALT decreases binding of metastatic cancer cells to activated lung endothelial cells. LSALT (50 μM) decreased binding of either murine melanoma cells (B16-F10) or murine sarcoma cells (Tao-1) to activated (TNFα and IL1β treated) human lung microvascular endothelial cells (HLMVEC). Untreated HLMVEC were used as control.
Figure 22B:
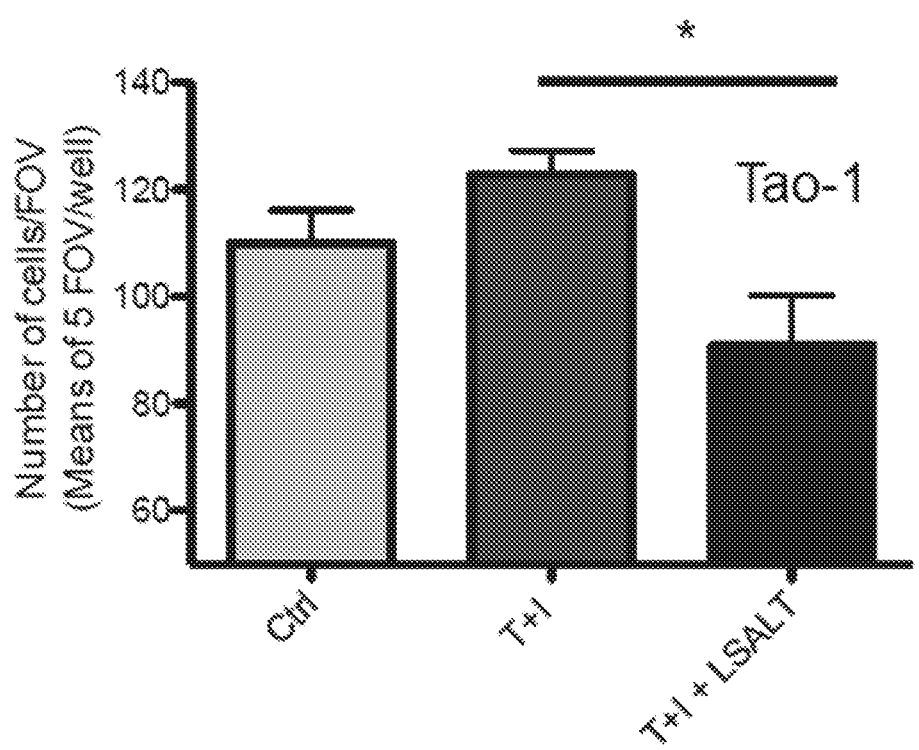

LSALT Decreases Binding of Metastatic Cancer Cells to Activated Lung Endothelial Cells LSALT decreases binding of metastatic cancer cells to human lung microvascular endothelial cells (HLMVEC) activated by TNFα and IL1β. FIG. 22A shows B16-F10 cells (murine melanoma) binding to HLMVEC in the presence and absence of LSALT or scrambled peptide. FIG. 22B shows Tao-1 cells (murine sarcoma) binding to HLMVEC in the presence and absence of LSALT or scrambled peptide (50 µM).

Example 26

Figure 23A:
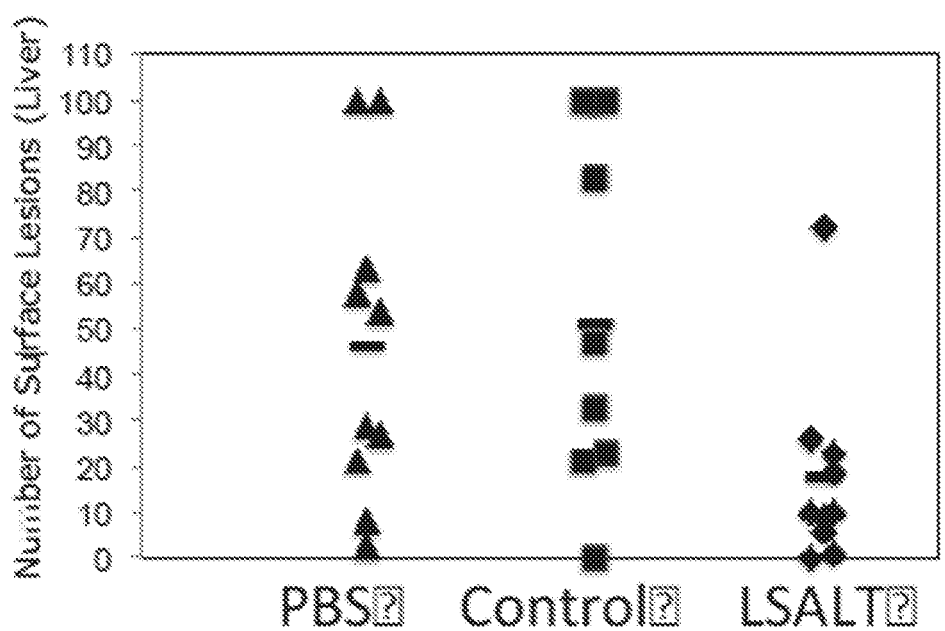
FIG. 23A provides a graph demonstrating LSALT reduces tumor burden in livers of animals injected with metastatic cancer cells. The number of liver metastatic lesions in animals injected with 4T1 murine breast cancer cells in the presence of control peptide (1 mM) or LSALT peptide (1 mM) was quantified.
Figure 23B:
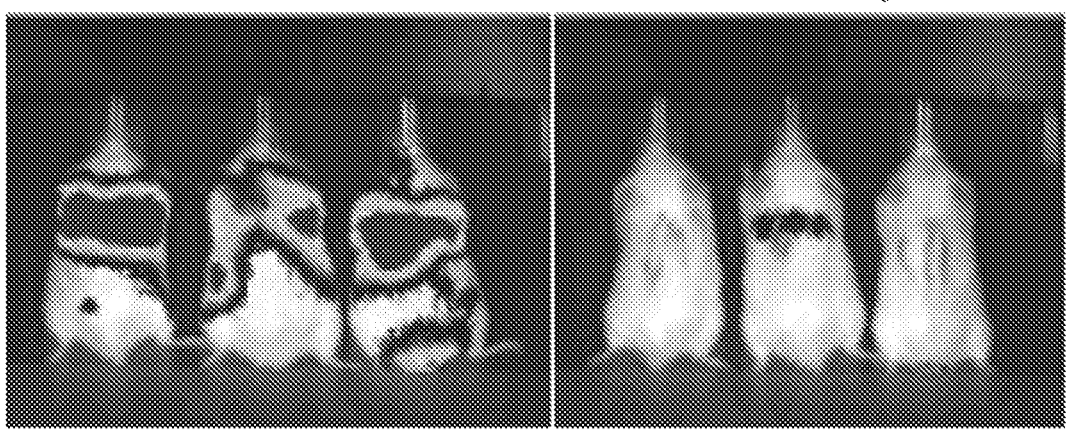
FIG. 23B provides a representative photomicrograph of tumor burden in animals injected with human melanoma cells. Tumor burden was analyzed by bioluminescent imaging of animals injected with luciferase expressing 70 W human melanoma cells in the presence of control peptide (1 mM) or LSALT peptide (1 mM).
Figure 23C:
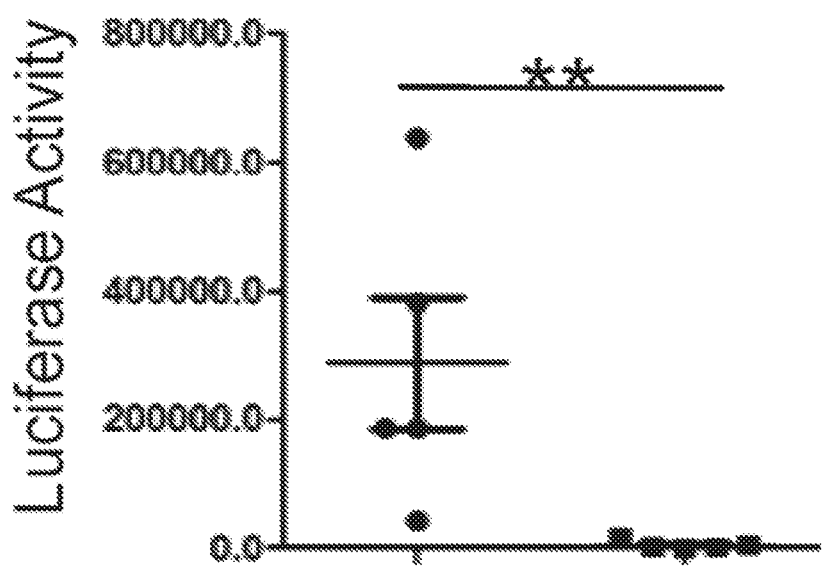
FIG. 23C provides graphical representation data of images in FIG. 23B.
Figure 23D:
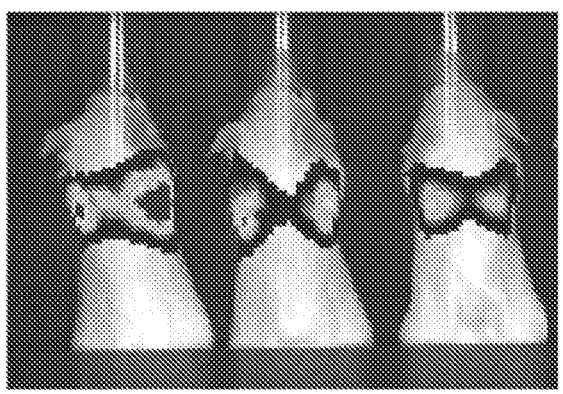
FIG. 23D provides a representative photomicrograph of tumor burden in animals injected with human osteosarcoma cells. Tumor burden was analyzed by bioluminescent imaging of animals injected with luciferase expressing 143B human osteosarcoma cells in the presence of control peptide (1 mM) or LSALT peptide (1 mM).
Figure 23D:
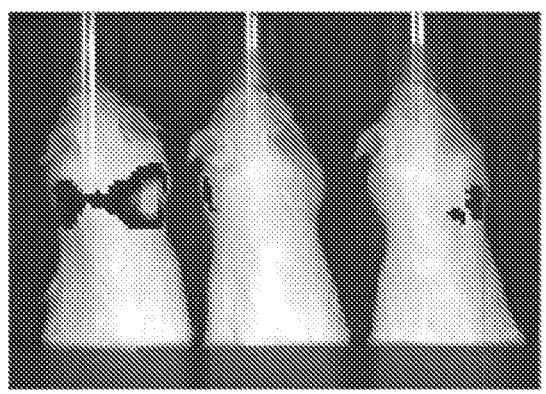
Figure 23E:
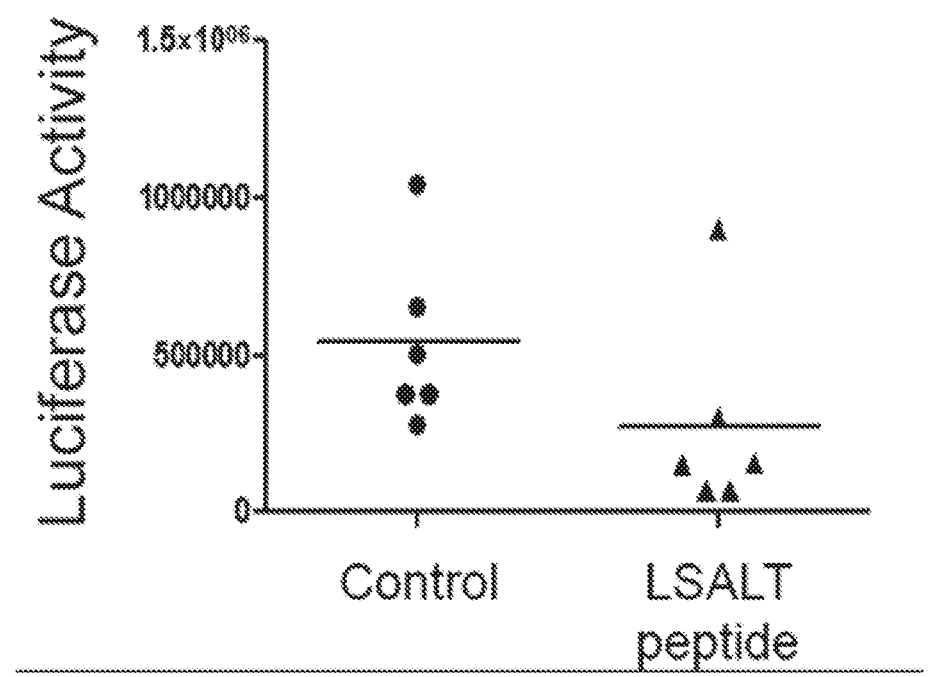
FIG. 23E provides graphical representation data of images in FIG. 23D.
Figure 23F:
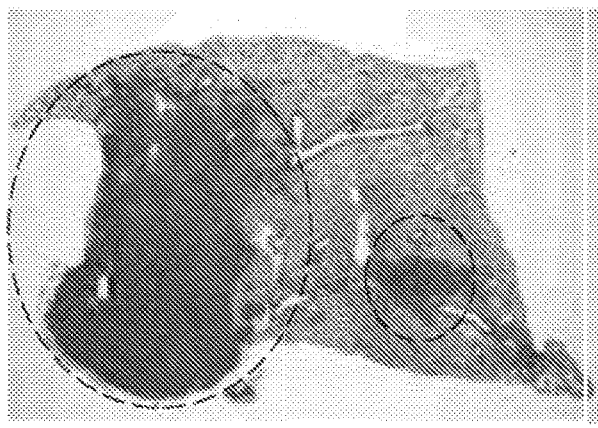
FIG. 23F provides representative H&E images of lung samples from animals injected with B16-F10 murine melanoma cells in the presence of control peptide (1 mM) or LSALT peptide (1 mM).
Figure 23F:
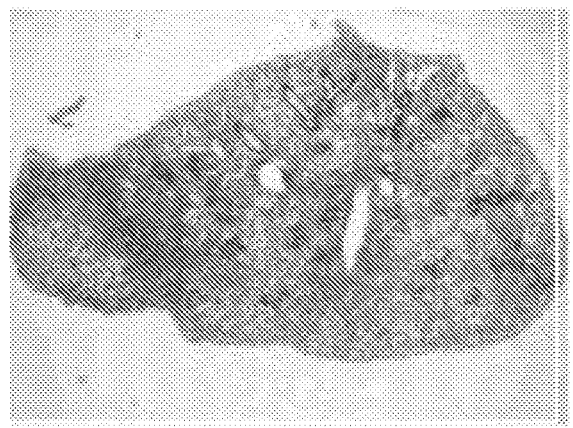
Figure 23G:
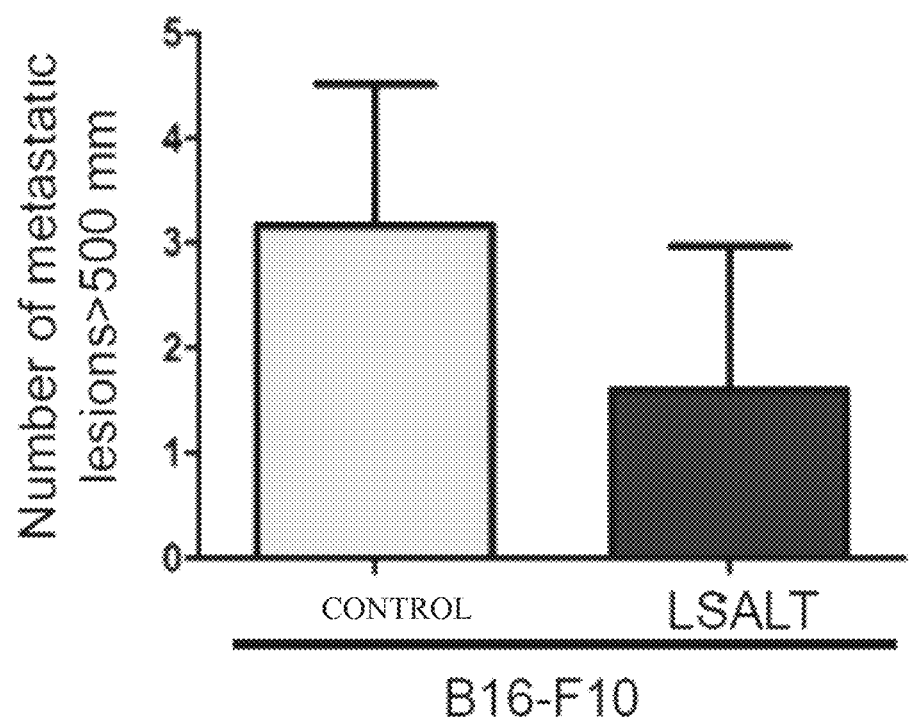
FIG. 23G provides a graph representing the quantification of metastatic lesions present in the lungs of animals injected with B16-F10 murine melanoma cells from FIG. 23F.
Figure 23H:
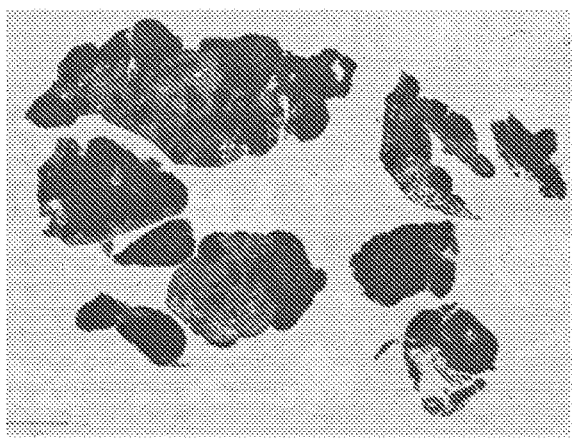
FIG. 23H provides representative H&E images of lung samples from animals injected with E0771.LMB murine breast cancer cells in the presence of control peptide (1 mM) or LSALT peptide (1 mM).
Figure 23H:
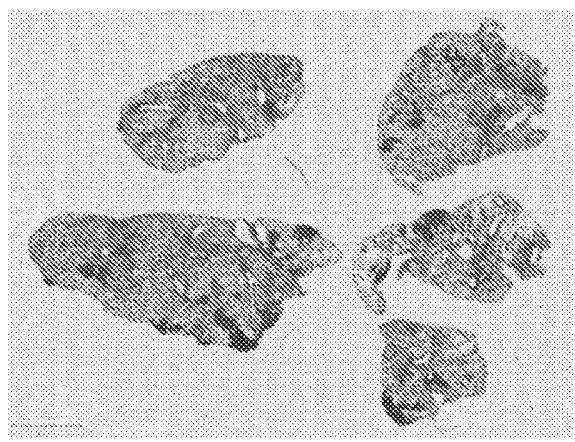
Figure 23I:
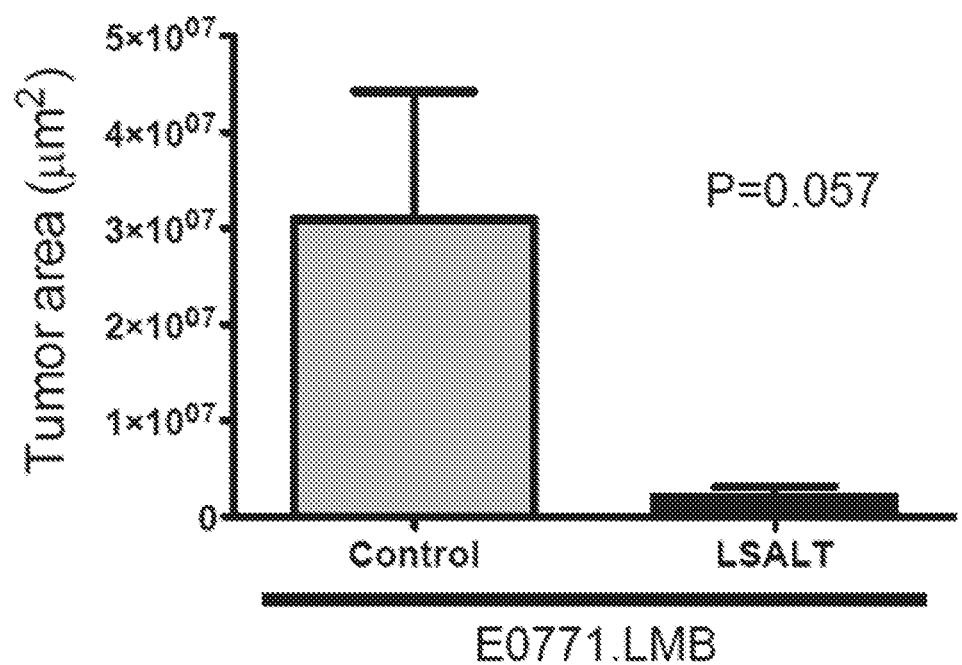
FIG. 23I provides a graph representing the quantification of metastatic lesion area present in the lungs of animals injected with E0771.LMB murine breast cancer cells from FIG. 23H.

Lsalt Reduces Tumor Burden in Livers and Lungs of Animals Injected with Metastatic Cancer Cells Metastasis model in mice was performed as described in Mohanty et al. FIG. 23A shows the number of liver metastatic lesions in animals injected with 4T1 murine breast cancer cells in the presence of control or LSALT peptide (1 mM). FIG. 23B shows bioluminescent imaging of animals injected with luciferase expressing 70 W human melanoma cells in the presence of control or LSALT peptide. FIG. 23C shows quantification of luciferase activity in 70 W treated animals. FIG. 23D shows bioluminescent imaging of animals injected with luciferase expressing 143B human osteosarcoma cells in the presence of control or LSALT peptide (1 mM) FIG. 23E shows quantification of luciferase activity in 143B treated animals. FIG. 23F shows representative H&E images of lung samples from animals injected with B16-F10 murine melanoma cells in the presence of control or LSALT peptide (1 mM). FIG. 23G shows the quantification of metastatic lesions present in the lungs of animals in FIG. 23F. FIG. 23H shows representative H&E images of lung samples from animals injected with E0771.LMB murine breast cancer cells in the presence of control or LSALT peptide (1 mM). FIG. 23I shows the quantification of tumor area in lungs of animals in FIG. 23H.

It will be appreciated how various changes and modifications may be made without departing from the invention.

SEQUENCE LISTING

<160> NUMBER OF SEQ ID NOS: 50

<210> SEQ ID NO 1
<211> LENGTH: 16
<212> TYPE: PRT
<213> ORGANISM: Artificial Sequence
<220> FEATURE:
<223> OTHER INFORMATION: synthetic peptide derived from a random phage
      peptide library (M13)

<400> SEQUENCE: 1

Leu Ser Ala Leu Thr Pro Ser Pro Ser Trp Leu Lys Tyr Lys Ala Leu
1               5                   10                  15

<210> SEQ ID NO 2
<211> LENGTH: 17
<212> TYPE: PRT
<213> ORGANISM: Artificial Sequence
<220> FEATURE:
<223> OTHER INFORMATION: synthetic peptide derived from a random phage
      peptide library (M13)

<400> SEQUENCE: 2

Gly Leu Ser Ala Leu Thr Pro Ser Pro Ser Trp Leu Lys Tyr Lys Ala
1               5                   10                  15

Leu

-continued

```
<210> SEQ ID NO 3
<211> LENGTH: 18
<212> TYPE: PRT
<213> ORGANISM: artificial sequence
<220> FEATURE:
<223> OTHER INFORMATION: synthetic peptide derived from a random phage
      peptide library (M13)

<400> SEQUENCE: 3

Gly Gly Leu Ser Ala Leu Thr Pro Ser Pro Ser Trp Leu Lys Tyr Lys
1               5                   10                  15

Ala Leu

<210> SEQ ID NO 4
<211> LENGTH: 19
<212> TYPE: PRT
<213> ORGANISM: Artificial Sequence
<220> FEATURE:
<223> OTHER INFORMATION: synthetic peptide derived from a random phage
      peptide library (M13)

<400> SEQUENCE: 4

Gly Gly Gly Leu Ser Ala Leu Thr Pro Ser Pro Ser Trp Leu Lys Tyr
1               5                   10                  15

Lys Ala Leu

<210> SEQ ID NO 5
<211> LENGTH: 13
<212> TYPE: PRT
<213> ORGANISM: Artificial Sequence
<220> FEATURE:
<223> OTHER INFORMATION: synthetic peptide derived from a random phage
      peptide library (M13)

<400> SEQUENCE: 5

Leu Thr Pro Ser Pro Ser Trp Leu Lys Tyr Lys Ala Leu
1               5                   10

<210> SEQ ID NO 6
<211> LENGTH: 12
<212> TYPE: PRT
<213> ORGANISM: Artificial Sequence
<220> FEATURE:
<223> OTHER INFORMATION: synthetic peptide derived from a random phage
      peptide library (Ph.D.-12 library)

<400> SEQUENCE: 6

Lys His Met His Trp His Pro Pro Ala Leu Asn Thr
1               5                   10

<210> SEQ ID NO 7
<211> LENGTH: 9
<212> TYPE: PRT
<213> ORGANISM: Artificial Sequence
<220> FEATURE:
<223> OTHER INFORMATION: synthetic peptide derived from a random phage
      peptide library (Ph.D.-12 library)
<220> FEATURE:
<221> NAME/KEY: MISC_FEATURE
<222> LOCATION: (4)..(4)
<223> OTHER INFORMATION: X  can be any naturally occurring aminno acid
<220> FEATURE:
<221> NAME/KEY: MISC_FEATURE
<222> LOCATION: (4)..(4)
<223> OTHER INFORMATION: Xaa  can be any naturally occurring aminno acid
<220> FEATURE:
<221> NAME/KEY: MISC_FEATURE
```

```
<222> LOCATION: (6)..(8)
<223> OTHER INFORMATION: X  can be any naturally occurring aminno acid
<220> FEATURE:
<221> NAME/KEY: MISC_FEATURE
<222> LOCATION: (6)..(8)
<223> OTHER INFORMATION: X  can be any naturally occurring aminno acid

<400> SEQUENCE: 7

Ile Pro Lys Xaa Pro Xaa Xaa Xaa Pro
1               5

<210> SEQ ID NO 8
<211> LENGTH: 12
<212> TYPE: PRT
<213> ORGANISM: Artificial Sequence
<220> FEATURE:
<223> OTHER INFORMATION: synthetic peptide derived from a random phage
      peptide library (Ph.D.-12 library)

<400> SEQUENCE: 8

His Ile Pro Lys Ser Pro Ile Gln Ile Pro Ile Ile
1               5                   10

<210> SEQ ID NO 9
<211> LENGTH: 15
<212> TYPE: PRT
<213> ORGANISM: Artificial Sequence
<220> FEATURE:
<223> OTHER INFORMATION: synthetic peptide derived from a random phage
      peptide library (M13)

<400> SEQUENCE: 9

Ser Ala Leu Thr Pro Ser Pro Ser Trp Leu Lys Tyr Lys Ala Leu
1               5                   10                  15

<210> SEQ ID NO 10
<211> LENGTH: 14
<212> TYPE: PRT
<213> ORGANISM: Artificial Sequence
<220> FEATURE:
<223> OTHER INFORMATION: synthetic peptide derived from a random phage
      peptide library (M13)

<400> SEQUENCE: 10

Ala Leu Thr Pro Ser Pro Ser Trp Leu Lys Tyr Lys Ala Leu
1               5                   10

<210> SEQ ID NO 11
<211> LENGTH: 12
<212> TYPE: PRT
<213> ORGANISM: Artificial Sequence
<220> FEATURE:
<223> OTHER INFORMATION: synthetic peptide derived from a random phage
      peptide library (M13)

<400> SEQUENCE: 11

Thr Pro Ser Pro Ser Trp Leu Lys Tyr Lys Ala Leu
1               5                   10

<210> SEQ ID NO 12
<211> LENGTH: 10
<212> TYPE: PRT
<213> ORGANISM: Artificial Sequence
<220> FEATURE:
<223> OTHER INFORMATION: synthetic peptide derived from a random phage
      peptide library (M13)

<400> SEQUENCE: 12
```

```
Ser Pro Ser Trp Leu Lys Tyr Lys Ala Leu
1               5                   10
```

<210> SEQ ID NO 13
<211> LENGTH: 10
<212> TYPE: PRT
<213> ORGANISM: Artificial Sequence
<220> FEATURE:
<223> OTHER INFORMATION: synthetic peptide derived from a random phage
      peptide library (M13)

<400> SEQUENCE: 13

```
Thr Pro Ser Pro Ser Trp Leu Lys Tyr Lys
1               5                   10
```

<210> SEQ ID NO 14
<211> LENGTH: 8
<212> TYPE: PRT
<213> ORGANISM: Artificial Sequence
<220> FEATURE:
<223> OTHER INFORMATION: synthetic peptide derived from a random phage
      peptide library (M13)

<400> SEQUENCE: 14

```
Ser Trp Leu Lys Tyr Lys Ala Leu
1               5
```

<210> SEQ ID NO 15
<211> LENGTH: 16
<212> TYPE: PRT
<213> ORGANISM: Artificial Sequence
<220> FEATURE:
<223> OTHER INFORMATION: synthetic peptide derived from a random phage
      peptide library (M13)

<400> SEQUENCE: 15

```
Ala Ser Ala Leu Thr Pro Ser Pro Ser Trp Leu Lys Tyr Lys Ala Leu
1               5                   10                  15
```

<210> SEQ ID NO 16
<211> LENGTH: 16
<212> TYPE: PRT
<213> ORGANISM: Artificial Sequence
<220> FEATURE:
<223> OTHER INFORMATION: synthetic peptide derived from a random phage
      peptide library (M13)

<400> SEQUENCE: 16

```
Leu Ala Ala Leu Thr Pro Ser Pro Ser Trp Leu Lys Tyr Lys Ala Leu
1               5                   10                  15
```

<210> SEQ ID NO 17
<211> LENGTH: 16
<212> TYPE: PRT
<213> ORGANISM: Artificial Sequence
<220> FEATURE:
<223> OTHER INFORMATION: synthetic peptide derived from a random phage
      peptide library (M13)

<400> SEQUENCE: 17

```
Leu Ser Ala Ala Thr Pro Ser Pro Ser Trp Leu Lys Tyr Lys Ala Leu
1               5                   10                  15
```

<210> SEQ ID NO 18
<211> LENGTH: 16
<212> TYPE: PRT
<213> ORGANISM: Artificial Sequence
<220> FEATURE:

<223> OTHER INFORMATION: synthetic peptide derived from a random phage
      peptide library (M13)

<400> SEQUENCE: 18

Leu Ser Ala Ala Thr Pro Ser Pro Ser Trp Leu Lys Tyr Lys Ala Leu
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: synthetic peptide derived from a random phage
      peptide library (M13)

<400> SEQUENCE: 19

Leu Ser Ala Leu Ala Pro Ser Pro Ser Trp Leu Lys Tyr Lys Ala Leu
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: synthetic peptide derived from a random phage
      peptide library (M13)

<400> SEQUENCE: 20

Leu Ser Ala Leu Thr Ala Ser Pro Ser Trp Leu Lys Tyr Lys Ala Leu
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: synthetic peptide derived from a random phage
      peptide library (M13)

<400> SEQUENCE: 21

Leu Ser Ala Leu Thr Pro Ala Pro Ser Trp Leu Lys Tyr Lys Ala Leu
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: synthetic peptide derived from a random phage
      peptide library (M13)

<400> SEQUENCE: 22

Leu Ser Ala Leu Thr Pro Ser Ala Ser Trp Leu Lys Tyr Lys Ala Leu
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: synthetic peptide derived from a random phage
      peptide library (M13)

<400> SEQUENCE: 23

Leu Ser Ala Leu Thr Pro Ser Pro Ala Trp Leu Lys Tyr Lys Ala Leu
1               5                   10                  15

```
<210> SEQ ID NO 24
<211> LENGTH: 16
<212> TYPE: PRT
<213> ORGANISM: Artificial Sequence
<220> FEATURE:
<223> OTHER INFORMATION: synthetic peptide derived from a random phage
      peptide library (M13)

<400> SEQUENCE: 24

Leu Ser Ala Leu Thr Pro Ser Pro Ser Ala Leu Lys Tyr Lys Ala Leu
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: synthetic peptide derived from a random phage
      peptide library (M13)

<400> SEQUENCE: 25

Leu Ser Ala Leu Thr Pro Ser Pro Ser Trp Ala Lys Tyr Lys Ala Leu
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: synthetic peptide derived from a random phage
      peptide library (M13)

<400> SEQUENCE: 26

Leu Ser Ala Leu Thr Pro Ser Pro Ser Trp Leu Ala Tyr Lys Ala Leu
1               5                   10                  15

<210> SEQ ID NO 27
<211> LENGTH: 16
<212> TYPE: PRT
<213> ORGANISM: Artificial Sequence
<220> FEATURE:
<223> OTHER INFORMATION: synthetic peptide derived from a random phage
      peptide library (M13)

<400> SEQUENCE: 27

Leu Ser Ala Leu Thr Pro Ser Pro Ser Trp Leu Lys Ala Lys Ala Leu
1               5                   10                  15

<210> SEQ ID NO 28
<211> LENGTH: 16
<212> TYPE: PRT
<213> ORGANISM: Artificial Sequence
<220> FEATURE:
<223> OTHER INFORMATION: synthetic peptide derived from a random phage
      peptide library (M13)

<400> SEQUENCE: 28

Leu Ser Ala Leu Thr Pro Ser Pro Ser Trp Leu Lys Tyr Ala Ala Leu
1               5                   10                  15

<210> SEQ ID NO 29
<211> LENGTH: 16
<212> TYPE: PRT
<213> ORGANISM: Artificial Sequence
<220> FEATURE:
<223> OTHER INFORMATION: synthetic peptide derived from a random phage
      peptide library (M13)

<400> SEQUENCE: 29
```

```
Leu Ser Ala Leu Thr Pro Ser Pro Ser Trp Leu Lys Tyr Lys Ala Leu
1               5                   10                  15

<210> SEQ ID NO 30
<211> LENGTH: 16
<212> TYPE: PRT
<213> ORGANISM: Artificial Sequence
<220> FEATURE:
<223> OTHER INFORMATION: synthetic peptide derived from a random phage
      peptide library (M13)

<400> SEQUENCE: 30

Leu Ser Ala Leu Thr Pro Ser Pro Ser Trp Leu Lys Tyr Lys Ala Ala
1               5                   10                  15

<210> SEQ ID NO 31
<211> LENGTH: 16
<212> TYPE: PRT
<213> ORGANISM: artificial seqience
<220> FEATURE:
<223> OTHER INFORMATION: synthetic peptide derived from a random phage
      peptide library (M13)
<220> FEATURE:
<221> NAME/KEY: MOD_RES
<222> LOCATION: (1)..(1)
<223> OTHER INFORMATION: Biotinylated

<400> SEQUENCE: 31

Leu Ser Ala Leu Thr Pro Ser Pro Ser Trp Leu Lys Tyr Lys Ala Leu
1               5                   10                  15

<210> SEQ ID NO 32
<211> LENGTH: 16
<212> TYPE: PRT
<213> ORGANISM: Artificial Sequence
<220> FEATURE:
<223> OTHER INFORMATION: synthetic peptide derived from a random phage
      peptide library (M13)
<220> FEATURE:
<221> NAME/KEY: MOD_RES
<222> LOCATION: (1)..(1)
<223> OTHER INFORMATION: Biotinylated

<400> SEQUENCE: 32

Ala Ser Ala Leu Thr Pro Ser Pro Ser Trp Leu Lys Tyr Lys Ala Leu
1               5                   10                  15

<210> SEQ ID NO 33
<211> LENGTH: 16
<212> TYPE: PRT
<213> ORGANISM: artificial sequence
<220> FEATURE:
<223> OTHER INFORMATION: synthetic peptide derived from a random phage
      peptide library (M13)
<220> FEATURE:
<221> NAME/KEY: MOD_RES
<222> LOCATION: (1)..(1)
<223> OTHER INFORMATION: biotinylated

<400> SEQUENCE: 33

Leu Ala Ala Leu Thr Pro Ser Pro Ser Trp Leu Lys Tyr Lys Ala Leu
1               5                   10                  15

<210> SEQ ID NO 34
<211> LENGTH: 16
<212> TYPE: PRT
<213> ORGANISM: Artificial Sequence
<220> FEATURE:
<223> OTHER INFORMATION: synthetic peptide derived from a random phage
```

```
        peptide library (M13)
<220> FEATURE:
<221> NAME/KEY: MOD_RES
<222> LOCATION: (1)..(1)
<223> OTHER INFORMATION: biotinylated

<400> SEQUENCE: 34

Leu Ser Gly Leu Thr Pro Ser Pro Ser Trp Leu Lys Tyr Lys Ala Leu
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: synthetic peptide derived from a random phage
      peptide library (M13)
<220> FEATURE:
<221> NAME/KEY: MOD_RES
<222> LOCATION: (1)..(1)
<223> OTHER INFORMATION: biotinylated

<400> SEQUENCE: 35

Leu Ser Ala Ala Thr Pro Ser Pro Ser Trp Leu Lys Tyr Lys Ala Leu
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: synthetic peptide derived from a random phage
      peptide library (M13)
<220> FEATURE:
<221> NAME/KEY: MOD_RES
<222> LOCATION: (1)..(1)
<223> OTHER INFORMATION: biotinylated

<400> SEQUENCE: 36

Leu Ser Ala Leu Ala Pro Ser Pro Ser Trp Leu Lys Tyr Lys Ala Leu
1               5                   10                  15

<210> SEQ ID NO 37
<211> LENGTH: 16
<212> TYPE: PRT
<213> ORGANISM: Artificial Sequence
<220> FEATURE:
<223> OTHER INFORMATION: synthetic peptide derived from a random phage
      peptide library (M13)
<220> FEATURE:
<221> NAME/KEY: MOD_RES
<222> LOCATION: (1)..(1)
<223> OTHER INFORMATION: biotinylated

<400> SEQUENCE: 37

Leu Ser Ala Leu Thr Gly Ser Pro Ser Trp Leu Lys Tyr Lys Ala Leu
1               5                   10                  15

<210> SEQ ID NO 38
<211> LENGTH: 16
<212> TYPE: PRT
<213> ORGANISM: Artificial Sequence
<220> FEATURE:
<223> OTHER INFORMATION: synthetic peptide derived from a random phage
      peptide library (M13)
<220> FEATURE:
<221> NAME/KEY: MOD_RES
<222> LOCATION: (1)..(1)
<223> OTHER INFORMATION: biotinylated

<400> SEQUENCE: 38
```

Leu Ser Ala Leu Thr Pro Ala Pro Ser Trp Leu Lys Tyr Lys Ala Leu
1               5                   10                  15

<210> SEQ ID NO 39
<211> LENGTH: 16
<212> TYPE: PRT
<213> ORGANISM: Artificial Sequence
<220> FEATURE:
<223> OTHER INFORMATION: synthetic peptide derived from a random phage
      peptide library (M13)
<220> FEATURE:
<221> NAME/KEY: MOD_RES
<222> LOCATION: (1)..(1)
<223> OTHER INFORMATION: biotinylated

<400> SEQUENCE: 39

Leu Ser Ala Leu Thr Pro Ser Ala Ser Trp Leu Lys Tyr Lys Ala Leu
1               5                   10                  15

<210> SEQ ID NO 40
<211> LENGTH: 16
<212> TYPE: PRT
<213> ORGANISM: Artificial Sequence
<220> FEATURE:
<223> OTHER INFORMATION: synthetic peptide derived from a random phage
      peptide library (M13)
<220> FEATURE:
<221> NAME/KEY: MOD_RES
<222> LOCATION: (1)..(1)
<223> OTHER INFORMATION: biotinylated

<400> SEQUENCE: 40

Leu Ser Ala Leu Thr Pro Ser Pro Ala Trp Leu Lys Tyr Lys Ala Leu
1               5                   10                  15

<210> SEQ ID NO 41
<211> LENGTH: 16
<212> TYPE: PRT
<213> ORGANISM: Artificial Sequence
<220> FEATURE:
<223> OTHER INFORMATION: synthetic peptide derived from a random phage
      peptide library (M13)
<220> FEATURE:
<221> NAME/KEY: MOD_RES
<222> LOCATION: (1)..(1)
<223> OTHER INFORMATION: biotinylated

<400> SEQUENCE: 41

Leu Ser Ala Leu Thr Pro Ser Pro Ser Ala Leu Lys Tyr Lys Ala Leu
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: synthetic peptide derived from a random phage
      peptide library (M13)
<220> FEATURE:
<221> NAME/KEY: MOD_RES
<222> LOCATION: (1)..(1)
<223> OTHER INFORMATION: biotinylated

<400> SEQUENCE: 42

Leu Ser Ala Leu Thr Pro Ser Pro Ser Trp Ala Lys Tyr Lys Ala Leu
1               5                   10                  15

<210> SEQ ID NO 43
<211> LENGTH: 16

```
<212> TYPE: PRT
<213> ORGANISM: Artificial Sequence
<220> FEATURE:
<223> OTHER INFORMATION: synthetic peptide derived from a random phage
      peptide library (M13)
<220> FEATURE:
<221> NAME/KEY: MOD_RES
<222> LOCATION: (1)..(1)
<223> OTHER INFORMATION: biotinylated

<400> SEQUENCE: 43

Leu Ser Ala Leu Thr Pro Ser Pro Ser Trp Leu Ala Tyr Lys Ala Leu
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: synthetic peptide derived from a random phage
      peptide library (M13)
<220> FEATURE:
<221> NAME/KEY: MOD_RES
<222> LOCATION: (1)..(1)
<223> OTHER INFORMATION: biotinylated

<400> SEQUENCE: 44

Leu Ser Ala Leu Thr Pro Ser Pro Ser Trp Leu Lys Ala Lys Ala Leu
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: synthetic peptide derived from a random phage
      peptide library (M13)
<220> FEATURE:
<221> NAME/KEY: MOD_RES
<222> LOCATION: (1)..(1)
<223> OTHER INFORMATION: biotinylated

<400> SEQUENCE: 45

Leu Ser Ala Leu Thr Pro Ser Pro Ser Trp Leu Lys Tyr Ala Ala Leu
1               5                   10                  15

<210> SEQ ID NO 46
<211> LENGTH: 16
<212> TYPE: PRT
<213> ORGANISM: Artificial Sequence
<220> FEATURE:
<223> OTHER INFORMATION: synthetic peptide derived from a random phage
      peptide library (M13)
<220> FEATURE:
<221> NAME/KEY: MOD_RES
<222> LOCATION: (1)..(1)
<223> OTHER INFORMATION: biotinylated

<400> SEQUENCE: 46

Leu Ser Ala Leu Thr Pro Ser Pro Ser Trp Leu Lys Tyr Lys Gly Leu
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: synthetic peptide derived from a random phage
      peptide library (M13)
<220> FEATURE:
<221> NAME/KEY: MOD_RES
```

```
<222> LOCATION: (1)..(1)
<223> OTHER INFORMATION: biotinylated

<400> SEQUENCE: 47

Leu Ser Ala Leu Thr Pro Ser Pro Ser Trp Leu Lys Tyr Lys Ala Ala
1               5                   10                  15

<210> SEQ ID NO 48
<211> LENGTH: 16
<212> TYPE: PRT
<213> ORGANISM: Artificial Sequence
<220> FEATURE:
<223> OTHER INFORMATION: synthetic peptide derived from a random phage
      peptide library (M13)
<220> FEATURE:
<221> NAME/KEY: MOD_RES
<222> LOCATION: (1)..(1)
<223> OTHER INFORMATION: ACETYLATION

<400> SEQUENCE: 48

Leu Ser Ala Leu Thr Pro Ser Pro Ser Trp Leu Lys Tyr Lys Ala Leu
1               5                   10                  15

<210> SEQ ID NO 49
<211> LENGTH: 16
<212> TYPE: PRT
<213> ORGANISM: Artificial Sequence
<220> FEATURE:
<223> OTHER INFORMATION: synthetic peptide derived from a random phage
      peptide library (M13)
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (16)..(16)
<223> OTHER INFORMATION: AMIDATION

<400> SEQUENCE: 49

Leu Ser Ala Leu Thr Pro Ser Pro Ser Trp Leu Lys Tyr Lys Ala Leu
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: synthetic peptide derived from a random phage
      peptide library (M13)
<220> FEATURE:
<221> NAME/KEY: MOD_RES
<222> LOCATION: (1)..(1)
<223> OTHER INFORMATION: biotinylated
<220> FEATURE:
<221> NAME/KEY: MOD_RES
<222> LOCATION: (16)..(16)
<223> OTHER INFORMATION: AMIDATION

<400> SEQUENCE: 50

Leu Ser Ala Leu Thr Pro Ser Pro Ser Trp Leu Lys Tyr Lys Ala Leu
1               5                   10                  15
```

We claim:

1. An isolated peptide comprising SEQ. ID. NO: 8.

2. The isolated peptide of claim 1, wherein the peptide inhibits binding to DPEP-1.

3. The isolated peptide of claim 1, wherein the peptide further comprises at least 1, 2, 3, 4, or 5 amino acid residues at the N-terminus.

4. The isolated peptide of claim 1, wherein the peptide comprises one or more amino acids selected from the group consisting of D-amino acids, modified amino acids, amino acid analogs or combinations thereof.

5. The isolated peptide of claim 4, wherein the modified amino acids comprise a modification selected from the group consisting of methylation, amidation, and acetylation.

6. A pharmaceutical composition comprising an isolated peptide comprising SEQ. ID. NO: 8 and a pharmaceutically acceptable carrier.

7. A method of treating a disease or disorder in a subject in need thereof, comprising administering to the subject an effective amount of an isolated peptide comprising SEQ ID NO: 8, wherein the disease or disorder is selected from the group consisting of acute kidney injury, sepsis, tumor metastasis, inflammation and ischemia-reperfusion injury.

8. The method of claim 7, wherein the ischemia-reperfusion injury is associated with harvesting donor organs for transplantation.

9. The pharmaceutical composition of claim 6, wherein the carrier is selected from the group consisting of water, saline, phosphate buffered saline, alcohols, glycerol, ethanol, gum Arabic, vegetable oil, benzyl alcohols, polyethylene glycols, gelatin, carbohydrates, dextrose, magnesium stearate, talc, silicic acid, viscous paraffine, perfume oil, fatty acid esters, hydroxymethylcellulose, polyvinyl pyrrolidone and combinations thereof.

10. The pharmaceutical composition of claim 6, wherein the carrier is a liquid carrier selected from the group consisting of Ringer's solution, dextrose solution, serum-containing solutions, Hank's solution, oils, esters and glycols.

11. The pharmaceutical composition of claim 6, in the form of unit-dose or multi-dose sealed containers.

12. The pharmaceutical composition of claim 11, wherein the sealed container is an ampule or vial.

* * * * *